(12) United States Patent
Larsen et al.

(10) Patent No.: US 11,944,626 B2
(45) Date of Patent: Apr. 2, 2024

(54) SMALL MOLECULE INHIBITORS OF ALDH AND USES THEREOF

(71) Applicants: The Regents of the University of Michigan, Ann Arbor, MI (US); Indiana University Research and Technology Corporation, Indianapolis, IN (US)

(72) Inventors: Scott D. Larsen, South Lyon, MI (US); Brandt C. Huddle, Ann Arbor, MI (US); Kun Yang, Ann Arbor, MI (US); Ronald Buckanovich, Ann Arbor, MI (US); Thomas Hurley, Indianapolis, IN (US)

(73) Assignees: The Regents of the University of Michigan, Ann Arbor, MI (US); Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/311,533

(22) PCT Filed: Jun. 20, 2017

(86) PCT No.: PCT/US2017/038334
§ 371 (c)(1),
(2) Date: Dec. 19, 2018

(87) PCT Pub. No.: WO2017/223086
PCT Pub. Date: Dec. 28, 2017

(65) Prior Publication Data
US 2019/0255055 A1 Aug. 22, 2019

Related U.S. Application Data

(60) Provisional application No. 62/352,179, filed on Jun. 20, 2016.

(51) Int. Cl.
| | | |
|---|---|---|
| A61K 31/519 | (2006.01) |
| A61K 31/337 | (2006.01) |
| A61K 31/4745 | (2006.01) |
| A61K 31/522 | (2006.01) |
| A61K 31/555 | (2006.01) |
| A61K 31/7068 | (2006.01) |
| A61K 39/395 | (2006.01) |
| A61K 45/06 | (2006.01) |
| A61P 31/00 | (2006.01) |
| A61P 35/00 | (2006.01) |
| C07D 487/04 | (2006.01) |

(52) U.S. Cl.
CPC .......... *A61K 31/519* (2013.01); *A61K 31/337* (2013.01); *A61K 31/4745* (2013.01); *A61K 31/522* (2013.01); *A61K 31/555* (2013.01); *A61K 31/7068* (2013.01); *A61K 39/395* (2013.01); *A61K 45/06* (2013.01); *A61P 31/00* (2018.01); *A61P 35/00* (2018.01); *C07D 487/04* (2013.01)

(58) Field of Classification Search
CPC ................ C07D 487/04; A61K 31/337; A61K 31/4745; A61K 31/522; A61K 31/555; A61K 31/7068; A61K 31/519; A61K 39/395; A61K 45/06; A61P 31/00; A61P 35/00

See application file for complete search history.

(56) References Cited

U.S. PATENT DOCUMENTS

| 8,158,634 B2 * | 4/2012 | Liu | C07D 498/04 514/262.1 |
| 2004/0242596 A1 * | 12/2004 | Kim | A61K 31/519 514/260.1 |
| 2015/0306108 A1 | 10/2015 | Hurley et al. | |

FOREIGN PATENT DOCUMENTS

| DE | 290 656 A5 * | 6/1991 | |
| EP | 0733633 | 9/1996 | |
| IN | 2013MU01918 A * | 7/2015 | |
| WO | WO-2007000655 A2 * | 1/2007 | C07D 487/04 |
| WO | WO 2012/097196 | 7/2012 | |
| WO | WO-2014009891 A1 * | 1/2014 | C07D 215/26 |

OTHER PUBLICATIONS

Agarwal, RP, et al., Serum albumin and the metabolism of disulfiram. Biochem Pharmacol. Oct. 1, 1986;35(19):3341-7.
Balmer, JE, et al., Gene expression regulation by retinoic acid. J Lipid Res. Nov. 2002;43(11):1773-808.
Banh, A, et al., A novel aldehyde dehydrogenase-3 activator leads to adult salivary stem cell enrichment in vivo. Clin Cancer Res. Dec. 1, 2011;17(23):7265-72.
Berghe, TV, et al., Regulated necrosis: the expanding network of non-apoptotic cell death pathways. Nat Rev Mol Cell Biol. Feb. 2014;15(2):135-47.
Burgos-Ojeda, D, et al., CD24+ Ovarian Cancer Cells Are Enriched for Cancer-Initiating Cells and Dependent on JAK2 Signaling for Growth and Metastasis. Mol Cancer Ther. Jul. 2015;14(7):1717-27.
Canavan, HE, et al., Cell sheet detachment affects the extracellular matrix: a surface science study comparing thermal liftoff, enzymatic, and mechanical methods. J Biomed Mater Res A. Oct. 1, 2005;75(1):1-13.
Canter, RJ, et al., Anti-proliferative but not anti-angiogenic tyrosine kinase inhibitors enrich for cancer stem cells in soft tissue sarcoma. BMC Cancer. Oct. 10, 2014;14:756.
Carpentino, JE, et al., Aldehyde dehydrogenase-expressing colon stem cells contribute to tumorigenesis in the transition from colitis to cancer. Cancer Res. Oct. 15, 2009;69(20):8208-15.

(Continued)

Primary Examiner — Kara R Mcmillian
(74) Attorney, Agent, or Firm — Casimir Jones, S.C.; Robert A. Goetz

(57) ABSTRACT

This invention is in the field of medicinal chemistry. In particular, the invention relates to a new class of small-molecules having a thiopyrimidinone structure which function as inhibitors of ALDH protein, and their use as therapeutics for the treatment of cancer and other diseases.

1 Claim, 5 Drawing Sheets

(56) References Cited

OTHER PUBLICATIONS

Morgan, CA et al., Development of a high-throughput in vitro assay to identify selective inhibitors for human ALDH1A1. Chem Biol Interact. Jun. 5, 2015;234:29-37.
Chen, Y-C, et al., Aldehyde dehydrogenase 1 is a putative marker for cancer stem cells in head and neck squamous cancer. Biochemical & Biophysical Research Communications. 2009;385(3):307-13.
Choi, SA, et al., Disulfiram modulates stemness and metabolism of brain tumor initiating cells in atypical teratoid/rhabdoid tumors. Neuro Oncol. Jun. 2015;17(6):810-21.
Clarke, MF, et al., Cancer stem cells—perspectives on current status and future directions: AACR Workshop on cancer stem cells. Cancer Res. Oct. 1, 2006;66(19):9339-44.
Cojoc, M, et al., Aldehyde Dehydrogenase Is Regulated by β-Catenin/TCF and Promotes Radioresistance in Prostate Cancer Progenitor Cells. Cancer Res. Apr. 1, 2015;75(7):1482-94.
Connolly, DC, et al., Female mice chimeric for expression of the simian virus 40 TAg under control of the MISIIR promoter develop epithelial ovarian cancer. Cancer Res. Mar. 15, 2003;63(6):1389-97.
Croker, AK, et al., Inhibition of aldehyde dehydrogenase (ALDH) activity reduces chemotherapy and radiation resistance of stem-like ALDHhiCD44+ human breast cancer cells. Breast Cancer Res Treat. May 2012;133(1):75-87.
Deng, S, et al., Distinct expression levels and patterns of stem cell marker, aldehyde dehydrogenase isoform 1 (ALDH1), in human epithelial cancers. PLoS One. Apr. 21, 2010;5(4):e10277.
Dufour, P, et al., Sodium dithiocarb as adjuvant immunotherapy for high risk breast cancer: a randomized study. Biotherapy. 1993;6(1):9-12.
Duong, HQ, et al., Aldehyde dehydrogenase 1A1 confers intrinsic and acquired resistance to gemcitabine in human pancreatic adenocarcinoma MIA PaCa-2 cells. Int J Oncol. Sep. 2012;41(3):855-61.
Dylla, SJ, et al., Colorectal cancer stem cells are enriched in xenogeneic tumors following chemotherapy. PLoS One. Jun. 18, 2008;3(6):e2428.
Edwards, BK, et al., Annual report to the nation on the status of cancer, 1975-2002, featuring population-based trends in cancer treatment. J Natl Cancer Inst. Oct. 5, 2005;97(19):1407-27.
Eneanya, DI, et al., The actions of metabolic fate of disulfiram. Annu Rev Pharmacol Toxicol. 1981;21:575-96.
Extended European Search Report for PCT/US2017/038334, dated Jan. 16, 2020, 8 pages.
Flesken-Nikitin, A, et al., Ovarian surface epithelium at the junction area contains a cancer-prone stem cell niche. Nature. Mar. 14, 2013;495(7440):241-5.
Gasparetto, M, et al., Aldehyde dehydrogenases are regulators of hematopoietic stem cell numbers and B-cell development. Exp Hematol. Apr. 2012;40(4):318-29.e2.
Ginestier, C, et al., ALDH1 is a marker of normal and malignant human mammary stem cells and a predictor of poor clinical outcome. Cell Stem Cell. Nov. 2007;1(5):555-67.
Ginestier, C, et al., CXCR1 blockade selectively targets human breast cancer stem cells in vitro and in xenografts. J Clin Invest. Feb. 2010;120(2):485-97.
Gupta, PB, et al., Identification of selective inhibitors of cancer stem cells by high-throughput screening. Cell. Aug. 21, 2009;138(4):645-659.
Hedelin, M, et al., Dietary phytoestrogens and the risk of ovarian cancer in the women's lifestyle and health cohort study. Cancer Epidemiol Biomarkers Prev. Feb. 2011;20(2):308-17.
Hu X, et al., Bypassing cancer drug resistance by activating multiple death pathways—a proposal from the study of circumventing cancer drug resistance by induction of necroptosis. Cancer Lett. Feb. 8, 2008;259(2):127-37.
Huang, CP, et al., ALDH-positive lung cancer stem cells confer resistance to epidermal growth factor receptor tyrosine kinase inhibitors. Cancer Lett. Jan. 1, 2013;328(1):144-51.

Irving, CC, et al., Influence of disulfiram on the metabolism of the urinary bladder carcinogen N-butyl-N-(4-hydroxybutyl)nitrosamine in the rat. Carcinogenesis. Sep. 1987;8(9):1309-15.
Jiang, F, et al., Aldehyde dehydrogenase 1 is a tumor stem cell-associated marker in lung cancer. Mol Cancer Res. Mar. 2009;7(3):330-8.
Kast, RE, et al. Suppressing glioblastoma stem cell function by aldehyde dehydrogenase inhibition with chloramphenicol or disulfiram as a new treatment adjunct: an hypothesis. Curr Stem Cell Res Ther. Dec. 2009;4(4):314-7.
Kim RJ, et al., High aldehyde dehydrogenase activity enhances stem cell features in breast cancer cells by activating hypoxia-inducible factor-2α. Cancer Lett. Jun. 1, 2013;333(1):18-31.
Koppaka, V, et al., Aldehyde dehydrogenase inhibitors: a comprehensive review of the pharmacology, mechanism of action, substrate specificity, and clinical application. Pharmacol Rev. Jul. 2012;64(3):520-39.
Kryczek, I, et al., Expression of aldehyde dehydrogenase and CD133 defines ovarian cancer stem cells. Int J Cancer. Jan. 1, 2012;130(1):29-39.
Landen, CN, Jr., et al., Targeting aldehyde dehydrogenase cancer stem cells in ovarian cancer. Mol Cancer Ther. Dec. 2010;9(12):3186-99.
Levi, BP, et al., Aldehyde dehydrogenase 1a1 is dispensable for stem cell function in the mouse hematopoietic and nervous systems. Blood. Feb. 19, 2009;113(8):1670-80.
Li, Z, et al., ALDH maintains the stemness of lung adenoma stem cells by suppressing the Notch/CDK2/CCNE pathway. PLoS One. Mar. 26, 2014;9(3):e92669.
Lin, J, et al., Disulfiram is a DNA demethylating agent and inhibits prostate cancer cell growth. Prostate. Mar. 1, 2011;71(4):333-43.
Luo, Y, et al., ALDH1A isozymes are markers of human melanoma stem cells and potential therapeutic targets. Stem Cells. Oct. 2012;30(10):2100-13.
Ma, S, et al., Aldehyde dehydrogenase discriminates the CD133 liver cancer stem cell populations. Mol Cancer Res. Jul. 2008;6(7):1146-53.
Malcolm, R, et al., The safety of disulfiram for the treatment of alcohol and cocaine dependence in randomized clinical trials: guidance for clinical practice. Expert Opin Drug Saf. Jul. 2008;7(4):459-72.
Malki et al. Novel 1,5-diphenyl-6-substituted 1H-pyrazolo[3,4-d]pyrimidin-4(5H)-ones induced apoptosis in RKO colon cancer cells. J Enzyme Inhib Med Chem. Dec. 2016;31(6):1286-99.
Marchitti, SA, et al., Aldehyde dehydrogenase 3B1 (ALDH3B1): immunohistochemical tissue distribution and cellular-specific localization in normal and cancerous human tissues. J Histochem Cytochem. Sep. 2010;58(9):765-83.
Meacham, CE, et al. Tumour heterogeneity and cancer cell plasticity. Nature. Sep. 19, 2013;501(7467):328-37.
Moreb, JS, et al., The enzymatic activity of human aldehyde dehydrogenases 1A2 and 2 (ALDH1A2 and ALDH2) is detected by Aldefluor, inhibited by diethylaminobenzaldehyde and has significant effects on cell proliferation and drug resistance. Chem Biol Interact. Jan. 5, 2012;195(1):52-60.
Moreb, JS, et al., ALDH isozymes downregulation affects cell growth, cell motility and gene expression in lung cancer cells. Mol Cancer. Nov. 24, 2008;7:87.
Moreb, JS., Aldehyde dehydrogenase as a marker for stem cells. Curr Stem Cell Res Ther. Dec. 2008;3(4):237-46. Abstract Only.
Morrison, BW, et al., Disulfiram induces copper-dependent stimulation of reactive oxygen species and activation of the extrinsic apoptotic pathway in melanoma. Melanoma Res. Feb. 2010;20(1):11-20.
Muzio, G, et al., Aldehyde dehydrogenases and cell proliferation. Free Radic Biol Med. Feb. 15, 2012;52(4):735-46.
Napoli, JL, et al., Enzymes and binding proteins affecting retinoic acid concentrations. J Steroid Biochem Mol Biol. Jun. 1995;53(1-6):497-502.
Nechushtan, H, et al., A phase IIb trial assessing the addition of disulfiram to chemotherapy for the treatment of metastatic non-small cell lung cancer. Oncologist. Apr. 2015;20(4):366-7.

(56) References Cited

OTHER PUBLICATIONS

Ohman, AW, et al., Advances in tumor screening, imaging, and avatar technologies for high-grade serous ovarian cancer. Front Oncol. Nov. 18, 2014;4:322.
Perets, R, et al., Transformation of the fallopian tube secretory epithelium leads to high-grade serous ovarian cancer in Brca;Tp53;Pten models. Cancer Cell. Dec. 9, 2013;24(6):751-65.
Petersen, EN. The pharmacology and toxicology of disulfiram and its metabolites. Acta Psychiatr Scand Suppl. 1992;369:7-13.
Raha, D, et al., The cancer stem cell marker aldehyde dehydrogenase is required to maintain a drug-tolerant tumor cell subpopulation. Cancer Res. Jul. 1, 2014;74(13):3579-90.
Saw, YT, et al., Characterization of aldehyde dehydrogenase isozymes in ovarian cancer tissues and sphere cultures. BMC Cancer. Aug. 1, 2012;12:329.
Schafer, A, et al., Aldehyde dehydrogenase 1A1—a new mediator of resistance to temozolomide in glioblastoma. Neuro Oncol. Dec. 2012;14(12):1452-64.
Shank, JJ, et al., Metformin targets ovarian cancer stem cells in vitro and in vivo. Gynecol Oncol. Nov. 2012;127(2):390-7.
Silva, IA, et al., Aldehyde dehydrogenase in combination with CD133 defines angiogenic ovarian cancer stem cells that portend poor patient survival. Cancer Res. Jun. 1, 2011;71(11):3991-4001.
Steg, AD, et al., Stem cell pathways contribute to clinical chemoresistance in ovarian cancer. Clin Cancer Res. Feb. 1, 2012;18(3):869-81.
Wang, Y, et al., Blocking the formation of radiation-induced breast cancer stem cells. Oncotarget. Jun. 15, 2014;5(11):3743-55.
Wei, X, et al., Mullerian inhibiting substance preferentially inhibits stem/progenitors in human ovarian cancer cell lines compared with chemotherapeutics. Proc Natl Acad Sci U S A. Nov. 2, 2010;107(44):18874-9.
Yamanaka, S. A fresh look at iPS cells. Cell. Apr. 3, 2009;137(1):13-7.
Yip, NC, et al., Disulfiram modulated ROS-MAPK and NFκB pathways and targeted breast cancer cells with cancer stem cell-like properties. Br J Cancer. May 10, 2011;104(10):1564-74.
EP Search Report, EP Patent Application No. 17816061.0, dated Jan. 16, 2020, 8 pages.

* cited by examiner and 263119

SMALL MOLECULE INHIBITORS OF ALDH AND USES THEREOF

STATEMENT REGARDING FEDERALLY SPONSORED RESEARCH OR DEVELOPMENT

This invention was made with government support under AA018123, CA214567 and CA198409 awarded by the National Institutes of Health. The government has certain rights in the invention.

FIELD OF THE INVENTION

This invention is in the field of medicinal chemistry. In particular, the invention relates to a new class of small-molecules having a thiopyrimidinone structure which function as inhibitors of ALDH protein, and their use as therapeutics for the treatment of cancer and other diseases.

INTRODUCTION

Ovarian cancers are highly lethal tumors which account for approximately four percent of all women's cancers and are the fifth leading cause of cancer-related death among women.

Ovarian cancer is defined as cancer that forms in the tissues of the ovary. Most ovarian cancers start in either the cells on the surface of the ovary (epithelial carcinoma) or in the egg cells themselves (germ cell tumors). According to the Centers for Disease Control and Prevention, ovarian cancer is responsible for more deaths among women than any other cancer of the reproductive system (Centers for Disease Control and Prevention. (2014, March) Ovarian Cancer). One of every 68 women will develop ovarian cancer in their lifetime (see, Tung, C. et al., (2014) Quant Imaging Med Surg, 4(3):156-162). Early diagnosis of ovarian cancer increases the chances of survival but only 14.7% of ovarian cancers are diagnosed in the local stage where the cancer has not spread outside the ovary.

The difficulty in catching ovarian cancers early lies in the fact that there may be no symptoms or the symptoms may be very common such as bloating and abdominal pain. Women with a family history of ovarian cancer or between the ages of 55 and 64 are most frequently diagnosed with ovarian cancer. Treatments for ovarian cancer include cytoreductive surgery and chemotherapy (see, Khabele, D (2014) Front Oncol, 4; 4: 111). Cytoreductive surgery aims to debulk the tumor while platinum-based chemotherapy serves as a systemic therapy. Despite the treatment options available, women with advanced stages of ovarian cancer have low chances of survival.

Ovarian cancer patients often initially respond well to the platinum-based chemotherapy but eventually experience lower survival outcomes due to chemotherapy-induced resistance which can often occur rapidly and become fatal (see, Echevarria-Vargas I M, et al (2014) PLoS ONE 9 (5)). At diagnosis the majority of patients have metastatic disease and the long-term survival remains low. Certain ovarian cancers are highly lethal tumors due to the emergence of therapy-resistant ovarian cancer cells.

Improved methods for treating ovarian cancer and, in particular, therapy-resistant ovarian cancer cells are needed.

The present invention addresses such needs.

SUMMARY OF THE INVENTION

There has been no improvement in the cure rate for epithelial ovarian cancer (EOC) patients for the past 30 years. Approximately 22,000 women in the U.S. are diagnosed with ovarian cancer annually, and, despite high rates of initial clinical remission, ~15,000 will relapse and die of their disease (see, Edwards B K, et al., J Natl Cancer Inst. 2005; 97(19):1407-27). Clearly there is a significant need for new therapies. The primary agents for ovarian cancer therapy, platinum and taxanes, have been the same for decades. Furthermore, with the exception of p53, large scale 'omics' studies have not identified any predominant, targetable driver mutations. Thus novel hypothesis-driven therapeutic targets are necessary.

One possible new target for ovarian cancer is a subpopulation of cells knows as cancer stem-like cells (CSC). CSC are defined by "the capacity to self-renew and to cause the heterogeneous lineages of cancer cells that comprise the tumor" (see, Clarke M F, et al., Cancer research. 2006; 66(19):9339-44). Experimentally, agents specifically targeting CSC can increase chemotherapeutic efficacy by 100-fold (see, Gupta P B, et al., Cell. 2009; 138(4):645-59), reverse chemotherapy resistance (see, Wei X, et al., Proc Natl Acad Sci USA. 2010; 107(44):18874-9), and prevent cancer recurrences (see, Ginestier C, et al., J Clin Invest. 2010; 120(2): 485-97). These experimental data strongly suggest that targeting CSC will improve patient outcomes.

CSC from numerous malignancies, including ovarian cancer, can be identified by elevated aldehyde dehydrogenase (ALDH) enzymatic activity (see, Ginestier C, et al., Cell Stem Cell. 2007; 1(5):555-67; Carpentino J E, et al., Cancer research. 2009; 69(20):8208-15; Chen Y-C, et al., Biochemical & Biophysical Research Communications. 2009; 385(3):307-13; Deng S, et al., PLoS ONE [Electronic Resource].e10277; Dylla S J, et al., PLoS ONE. 2008; 3(6):e2428; Jiang F, et al., Molecular Cancer Research: MCR. 2009; 7(3):330-8; Ma S, et al., Molecular Cancer Research: MCR. 2008; 6(7):1146-53; Silva I A, et al., Cancer research. 2011; 71(11):3991-4001). Primary ALDH$^+$ EOC cells are chemotherapy-resistant, can both initiate and propagate tumors in mice, and can create the heterogeneous lineages of ovarian cancer cells (see, Silva I A, et al., Cancer research. 2011; 71(11):3991-4001). Based on the preferential activity of ALDH in chemotherapy-resistant tumor-propagating cells, ALDH has been implicated as a therapeutic target. Unfortunately, there are 19 human ALDH superfamily members, and the isozymes that contribute to CSC-specific ALDH activity remain unclear. Of the 19 human ALDH family members (see, Koppaka V, et al., Pharmacological reviews. 2012; 64(3):520-39; Muzio G, et al., Free radical biology & medicine. 2012; 52(4):735-46), ALDH1A1 is currently the most supported marker of EOC CSC based on the following: (i) the presence of ALDH1A1$^+$ CD133$^+$ cells in patients' primary tumor specimens correlates with poor outcome (see, Silva I A, et al., Cancer research. 2011; 71(11):3991-4001), (ii) ALDH1A1 is 100-fold upregulated in chemotherapy-resistant ovarian cancer cells and (iii) siRNA knockdown of ALDH1A1 restores chemosensitivity (see, Landen C N, Jr., et al., Mol Cancer Ther. 2010; 9(12):3186-99). However, ALDH1A2, ALDH1A3, and ALDH3B1 have also been implicated as contributing to EOC ALDH activity (see, Marchitti S A, et al., J Histochem Cytochem. 2010; 58(9):765-83; Saw Y T, et al., BMC Cancer. 2012; 12(1):329; Moreb J S, et al., Chemico-biological interactions. 2012; 195(1):52-60).

Studies from other tumors support ALDH as a therapeutic target (see, Landen C N, Jr., et al., Mol Cancer Ther. 2010; 9(12):3186-99; Yip N C, et al., British journal of cancer. 2011; 104(10):1564-74; Luo Y, et al., Stem cells. 2012; 30(10):2100-13; Moreb J S. Current stem cell research & therapy. 2008; 3(4):237-46). Broad spectrum ALDH inhibitors such as p-diethylaminobenzaldehyde (DEAB) and disulfiram have been reported to reverse chemotherapy resistance and reduce colony-forming units in vitro, and suppress tumor growth and metastasis in vivo (see, Croker A K, and Allan A L. et al., Breast cancer research and treatment. 2012; 133(1):75-87; Schafer A, et al., Neuro-oncology. 2012; 14(12):1452-64; Kim R J, et al., Cancer letters. 2013; 333(1): 18-31). Unfortunately neither DEAB, disulfiram, nor other currently available ALDH inhibitors (see, Morgan C A, and Hurley T D et al., Chemico-biological interactions. 2015; 234(29-37) are ideal candidates to target CSC in patients. Disulfiram has numerous active metabolites and off-target effects. In addition, disulfiram, DEAB and most others lack specificity for ALDH1 isozymes vs ALDH2, and loss of ALDH2 activity has been associated with liver inflammation and fibrosis (see, Kwon H J, et al., Hepatology. 2014; 60(1):146-57).

As such, improved ALDH inhibitors with improved selectivity are needed for the treatment of cancers having a chemotherapy resistance phenotype associated with CSC and/or ALDH activity (e.g., epithelial ovarian cancer). The present invention addresses this need.

Indeed, experiments conducted during the course of developing embodiments for the present invention synthesized new class of small-molecules having a thiopyrimidinone structure which function as inhibitors of ALDH protein. Such small-molecules were demonstrated to have optimal $IC_{50}$ values against ALDH (e.g., ALDH1A1, ALDH1A2, ALDH1A3, ALDH2). Such small-molecules were demonstrated to decrease CSC activity in ovarian cancer tumors and ALDH activity (e.g., ALDH1A1, ALDH1A2, ALDH1A3, ALDH2). Such small-molecules were demonstrated to decrease CSC activity in ovarian cancer tumors through a necroptosis mechanism.

As such, the present invention provides a new class of small-molecules having a thiopyrimidinone structure which function as inhibitors of ALDH protein, and their use as therapeutics for the treatment of cancer and other diseases.

More specifically, the present invention contemplates that exposure of animals (e.g., humans) suffering from cancer (e.g., and/or cancer related disorders) (e.g., cancers having CSC activity) (e.g., cancers having elevated ALDH activity) to therapeutically effective amounts of drug(s) having a thiopyrimidinone structure (e.g., small molecules having a thiopyrimidinone structure) that inhibit the activity of ALDH (e.g., ALDH1A1, ALDH1A2, ALDH1A3, ALDH2) will inhibit the growth of cancer cells (e.g., via a necroptosis based mechanism) or supporting cells outright and/or render such cells as a population more susceptible to the cell death-inducing activity of cancer therapeutic drugs or radiation therapies.

The present invention contemplates that inhibitors of ALDH (e.g., ALDH1A1, ALDH1A2, ALDH1A3, ALDH2) activity satisfy an unmet need for the treatment of multiple cancer types (e.g., cancers characterized with CSC activity and/or elevated ALDH activity), either when administered as monotherapy to induce cell growth inhibition, necroptosis and/or cell cycle arrest in cancer cells, or when administered in a temporal relationship with additional agent(s), such as other cell death-inducing or cell cycle disrupting cancer therapeutic drugs or radiation therapies (combination therapies), so as to render a greater proportion of the cancer cells or supportive cells susceptible to executing the apoptosis program compared to the corresponding proportion of cells in an animal treated only with the cancer therapeutic drug or radiation therapy alone.

In certain embodiments of the invention, combination treatment of animals with a therapeutically effective amount of a compound of the present invention and a course of an anticancer agent produces a greater tumor response and clinical benefit in such animals compared to those treated with the compound or anticancer drugs/radiation alone. Since the doses for all approved anticancer drugs and radiation treatments are known, the present invention contemplates the various combinations of them with the present compounds.

The Applicants have found that certain thiopyrimidinone compounds function as inhibitors of ALDH protein (e.g., ALDH1A1, ALDH1A2, ALDH1A3, ALDH2) and serve as therapeutics for the treatment of cancer and other diseases (e.g., diseases characterized with elevated ALDH activity). Thus, the present invention relates to thiopyrimidinone compounds useful for inhibiting ALDH activity (e.g., thereby facilitating CSC necroptosis), and increasing the sensitivity of cells to inducers of apoptosis and/or cell cycle arrest. Certain thiopyrimidinone compounds of the present invention may exist as stereoisomers including optical isomers. The invention includes all stereoisomers, both as pure individual stereoisomer preparations and enriched preparations of each, and both the racemic mixtures of such stereoisomers as well as the individual diastereomers and enantiomers that may be separated according to methods that are well known to those of skill in the art.

In a particular embodiment, thiopyrimidinone compounds encompassed within Formulas I and II are provided:

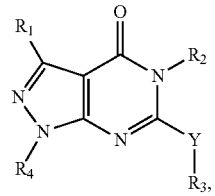

(Formula I)

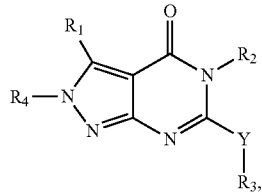

(Formula II)

including pharmaceutically acceptable salts, solvates, and/or prodrugs thereof.

Formulas I and II are not limited to a particular chemical moiety for R1, R2, R3, R4, or Y. In some embodiments, the particular chemical moiety for R1, R2, R3, R4, or Y independently include any chemical moiety that permits the resulting compound to inhibit ALDH activity (e.g., one or more of ALDH1A1, ALDH1A2, ALDH1A3, ALDH2 activity). In some embodiments, the particular chemical moiety for R1, R2, R3, R4, or Y independently include any chemical moiety that permits the resulting compound to inhibit CSC activity. In some embodiments, the particular chemical moiety for R1, R2, R3, R4, or Y independently include any chemical moiety that permits the resulting compound to induce necroptosis (e.g., CSC necroptosis).

In some embodiments, R1 is H or C1-C3 alkyl (substituted or non-substituted). In some embodiments, R1 is H, $CH_3$, $CH_2CH_3$, or $CH_2CH_2CH_3$.

In some embodiments, R2 is H, C0-C3-alkyl-Ar or C0-C3-alkyl-Heteroaryl, wherein the alkyls are independently substituted or non-substituted. In some embodiments, R2 is phenyl (substituted or non-substituted). In some embodiments, R2 is $CH_3$,

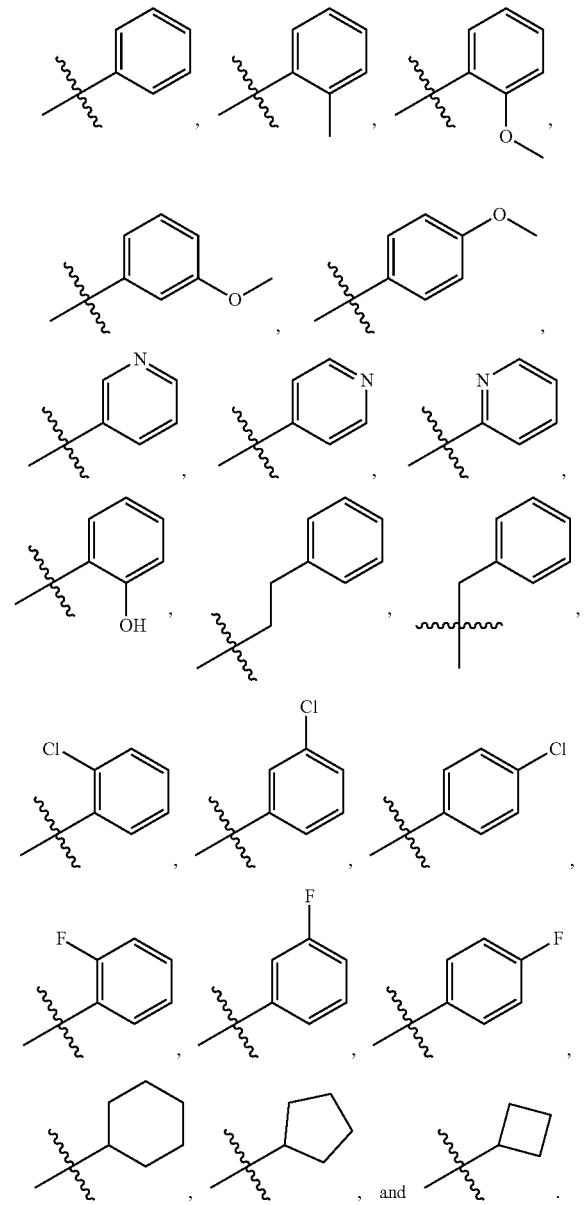

In some embodiments, Y is a linker that is present or absent. In some embodiments wherein Y is present, Y is selected from

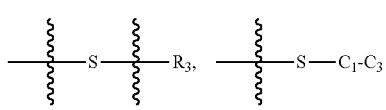

alkyl or alkenyl (substituted or unsubstituted) (branched or unbranched)

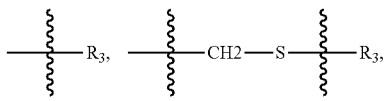

alkyl or alkenyl (substituted or unsubstituted) (branched or unbranched)

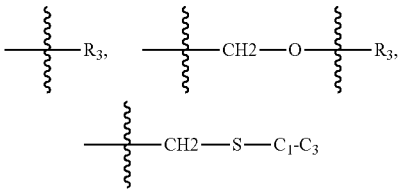

alkyl or alkenyl (substituted or unsubstituted) (branched or unbranched)

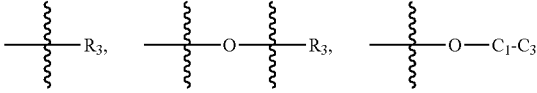

alkyl or alkenyl (substituted or unsubstituted) (branched or unbranched)

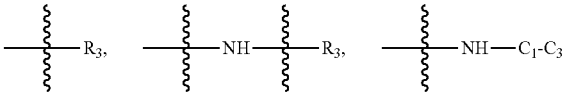

alkyl or alkenyl (substituted or unsubstituted) (branched or unbranched)

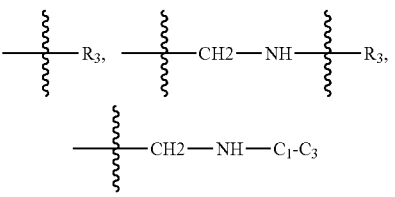

alkyl or alkenyl (substituted or unsubstituted) (branched or unbranched)

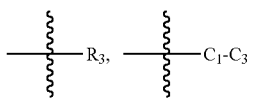

alkyl or alkenyl (substituted or unsubstituted) (branched or unbranched)

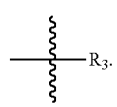

In some embodiments wherein Y is present, Y is selected from

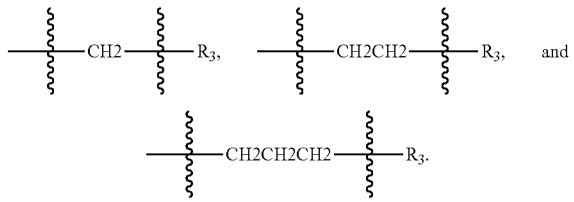

In some embodiments, R3 is H, C0-C8 alkyl, C0-C2-alkyl-Ar or C0-C2-alkyl-heteroaryl, wherein the alkyls are independently substituted or non-substituted. In some embodiments, R3 is C1-alkyl-Aryl or C1-alkyl-heteroaryl. In some embodiments, R3 is CH₃,

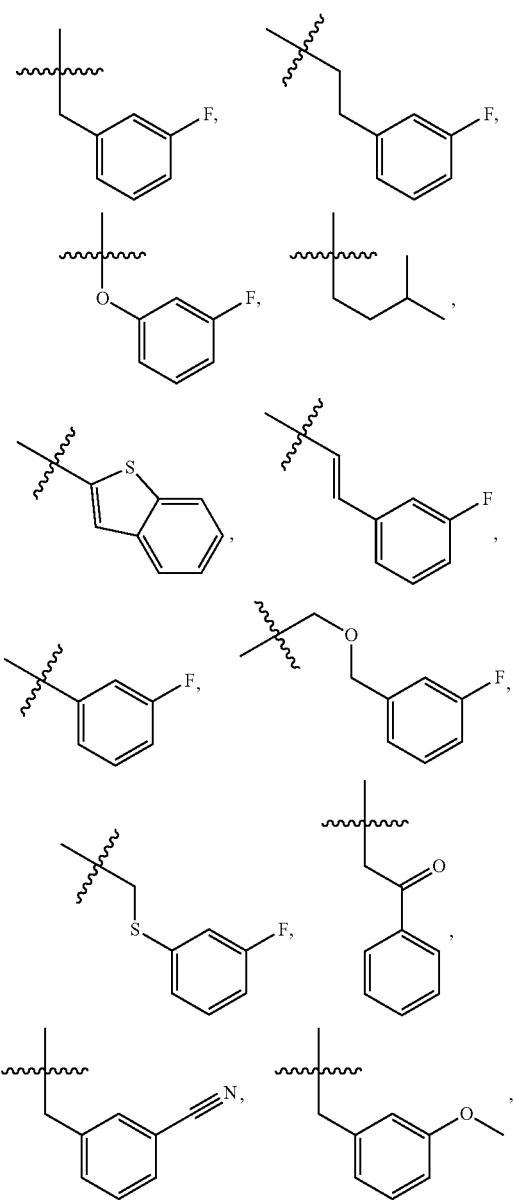

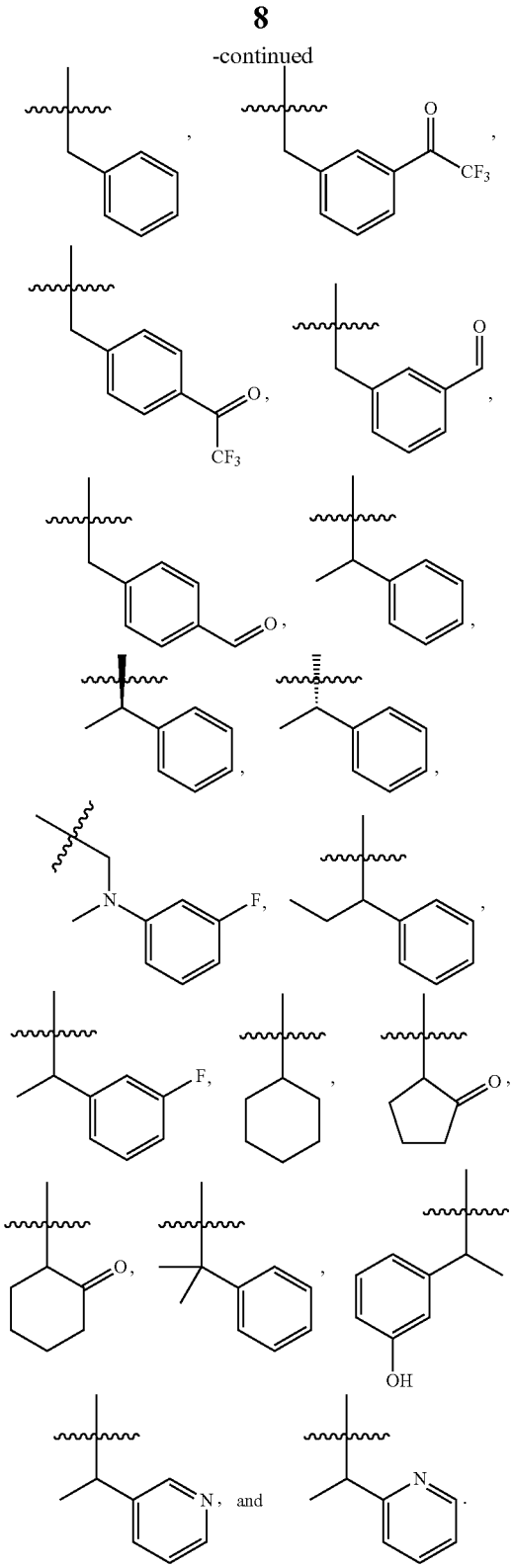

In some embodiments, R4 is H, C1-C6 alkyl or cycloalkyl, optionally substituted and wherein one or more carbons may be replaced by oxygen, wherein the alkyls are independently substituted or non-substituted. In some embodiments, R4 is C1-C4 alkyl or cycloalkyl, wherein one or more carbons may be replaced by O. In some embodiments, R4 is H, $CH_3$, $CH_2CH_3$,

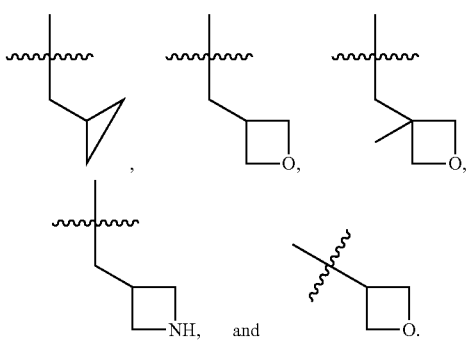

In a particular embodiment, thiopyrimidinone compounds encompassed within Formulas I and II are provided:

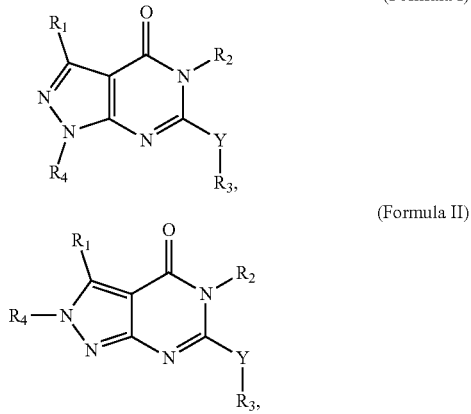

including pharmaceutically acceptable salts, solvates, and/or prodrugs thereof; wherein R1, R2, R3, and Y are defined as above; wherein R4 is H, C1-C6 alkyl or cycloalkyl (optionally substituted or unsubstituted) (wherein one or more carbons may be replaced by oxygen or nitrogen). In some embodiments, R4 is selected from H, $CH_3$, $CH_2CH_3$,

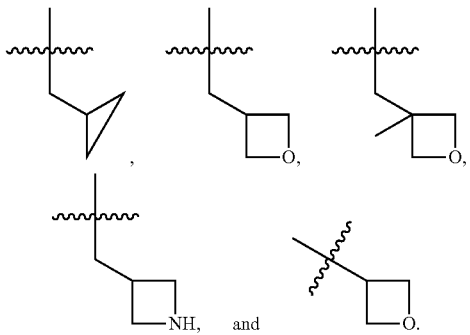

In some embodiments, the following compounds are contemplated for Formulas I and II:
6-((3-fluorobenzyl)thio)-5-(o-tolyl)-1H-pyrazolo[3,4-d]pyrimidin-4(5H)-one,
6-((3-fluorobenzyl)thio)-5-phenyl-1H-pyrazolo[3,4-d]pyrimidin-4(5H)-one,
6-((3-fluorobenzyl)thio)-1-methyl-5-(o-tolyl)-1H-pyrazolo[3,4-d]pyrimidin-4(5H)-one,
6-((3-fluorobenzyl)thio)-2-methyl-5-(o-tolyl)-2H-pyrazolo[3,4-d]pyrimidin-4(5H)-one,
1-ethyl-6-((3-fluorobenzyl)thio)-5-(o-tolyl)-1H-pyrazolo[3,4-d]pyrimidin-4(5H)-one,
2-ethyl-6-((3-fluorobenzyl)thio)-5-(o-tolyl)-2H-pyrazolo[3,4-d]pyrimidin-4(5H)-one,
1-(cyclopropylmethyl)-6-((3-fluorobenzyl)thio)-5-(o-tolyl)-1H-pyrazolo[3,4-d]pyrimidin-4(5H)-one,
2-(cyclopropylmethyl)-6-((3-fluorobenzyl)thio)-5-(o-tolyl)-2H-pyrazolo[3,4-d]pyrimidin-4(5H)-one,
6-((3-fluorobenzyl)thio)-1-(oxetan-3-yl)-5-(o-tolyl)-1H-pyrazolo[3,4-d]pyrimidin-4(5H)-one,
6-((3-fluorobenzyl)thio)-2-(oxetan-3-yl)-5-(o-tolyl)-2H-pyrazolo[3,4-d]pyrimidin-4(5H)-one,
6-((3-fluorobenzyl)thio)-1-(oxetan-3-ylmethyl)-5-(o-tolyl)-1H-pyrazolol[3,4-d]pyrimidin-4(5H)-one,
6-((3-fluorobenzyl)thio)-2-(oxetan-3-ylmethyl)-5-(o-tolyl)-2H-pyrazolo[3,4-d]pyrimidin-4(5H)-one,
6-((3-fluorobenzyl)thio)-2-methyl-5-phenyl-2H-pyrazolo[3,4-d]pyrimidin-4(5H)-one,
1-ethyl-6-((3-fluorobenzyl)thio)-5-phenyl-1H-pyrazolo[3,4-d]pyrimidin-4(5H)-one,
2-ethyl-6-((3-fluorobenzyl)thio)-5-phenyl-2H-pyrazolo[3,4-d]pyrimidin-4(5H)-one,
1-(cyclopropylmethyl)-6-((3-fluorobenzyl)thio)-5-phenyl-1H-pyrazolo[3,4-d]pyrimidin-4(5H)-one,
2-(cyclopropylmethyl)-6-((3-fluorobenzyl)thio)-5-phenyl-2H-pyrazolo[3,4-d]pyrimidin-4(5H)-one,
6-((3-fluorobenzyl)thio)-1-(oxetan-3-yl)-5-phenyl-1H-pyrazolo[3,4-d]pyrimidin-4(5H)-one,
6-((3-fluorobenzyl)thio)-2-(oxetan-3-yl)-5-phenyl-2H-pyrazolo[3,4-d]pyrimidin-4(5H)-one,
6-((3-fluorobenzyl)thio)-1-(oxetan-3-ylmethyl)-5-phenyl-1H-pyrazolo[3,4-d]pyrimidin-4(5H)-one,
6-((3-fluorobenzyl)thio)-2-(oxetan-3-ylmethyl)-5-phenyl-2H-pyrazolo[3,4-d]pyrimidin-4(5H)-one,
6-((3-fluorobenzyl)amino)-5-(o-tolyl)-1H-pyrazolo[3,4-d]pyrimidin-4(5H)-one,
6-((3-fluorophenethyl)amino)-1-methyl-5-(o-tolyl)-1H-pyrazolo[3,4-d]pyrimidin-4(5H)-one,
6-((3-fluorobenzyl)oxy)-1-methyl-5-(o-tolyl)-1H-pyrazolo[3,4-d]pyrimidin-4(5H)-one,
6-((3-fluorophenoxy)methyl)-1-methyl-5-phenyl-1H-pyrazolo[3,4-d]pyrimidin-4(5H)-one,
6-(((3-fluorobenzyl)amino)methyl)-1-methyl-5-phenyl-1H-pyrazolo[3,4-d]pyrimidin-4(5H)-one,
6-((3-fluorobenzyl)thio)-1-methyl-5-phenyl-1H-pyrazolo[3,4-d]pyrimidin-4(5H)-one,
6-((3-fluorobenzyl)thio)-5-(2-methoxyphenyl)-1-methyl-1H-pyrazolo[3,4-d]pyrimidin-4(5H)-one,
6-((3-fluorobenzyl)thio)-5-(3-methoxyphenyl)-1-methyl-1H-pyrazolo[3,4-d]pyrimidin-4(5H)-one,
6-((3-fluorobenzyl)thio)-5-(4-methoxyphenyl)-1-methyl-1H-pyrazolo[3,4-d]pyrimidin-4(5H)-one
6-((3-fluorobenzyl)thio)-1-methyl-5-(pyridin-3-yl)-1H-pyrazolo[3,4-d]pyrimidin-4(5H)-one,
6-((3-fluorobenzyl)thio)-1-methyl-5-(pyridin-4-yl)-1H-pyrazolo[3,4-d]pyrimidin-4(5H)-one,
6-((3-fluorobenzyl)thio)-5-(2-hydroxyphenyl)-1-methyl-1H-pyrazolo[3,4-d]pyrimidin-4(5H)-one,
6-((3-fluorobenzyl)thio)-1-methyl-5-(pyridin-2-yl)-1H-pyrazolo[3,4-d]pyrimidin-4(5H)-one,
6-((3-fluorobenzyl)thio)-1-methyl-5-phenethyl-1H-pyrazolo[3,4-d]pyrimidin-4(5H)-one,
5-benzyl-6-((3-fluorobenzyl)thio)-1-methyl-1H-pyrazolo[3,4-d]pyrimidin-4(5H)-one, 6-((3-fluorobenzyl)thio)-1,5-dimethyl-1H-pyrazolo[3,4-d]pyrimidin-4(5H)-one,
6-(isopentylthio)-1-methyl-5-phenyl-1H-pyrazolo[3,4-d]pyrimidin-4(5H)-one,
6-((3-fluorobenzyl)thio)-3-methyl-5-(o-tolyl)-2H-pyrazolo[3,4-d]pyrimidin-4(5H)-one,
6-(benzo[b]thiophen-2-ylmethoxy)-1-methyl-5-(o-tolyl)-1H-pyrazolo[3,4-d]pyrimidin-4(5H)-one,
5-(2-chlorophenyl)-6-(3-fluorobenzylthio)-1-methyl-1H-pyrazolo[3,4-d]pyrimidin-4(5H)-one, 5-(2-chlorophenyl)-6-((3-fluorobenzyl)thio)-1-methyl-1H-pyrazolo[3,4-d]pyrimidin-4(5H)-one,
5-(3-chlorophenyl)-6-((3-fluorobenzyl)thio)-1-methyl-1H-pyrazolo[3,4-d]pyrimidin-4(5H)-one,
5-(4-chlorophenyl)-6-((3-fluorobenzyl)thio)-1-methyl-1H-pyrazolo[3,4-d]pyrimidin-4(5H)-one,
6-((3-fluorobenzyl)thio)-5-(2-fluorophenyl)-1-methyl-1H-pyrazolo[3,4-d]pyrimidin-4(5H)-one,
5-cyclohexyl-6-((3-fluorobenzyl)thio)-1-methyl-1H-pyrazolo[3,4-d]pyrimidin-4(5H)-one,
5-cyclopentyl-6-((3-fluorobenzyl)thio)-1-methyl-1H-pyrazolo[3,4-d]pyrimidin-4(5H)-one,
5-cyclobutyl-6-((3-fluorobenzyl)thio)-1-methyl-1H-pyrazolo[3,4-d]pyrimidin-4(5H)-one,
(E)-6-(3-fluorostyryl)-1-methyl-5-phenyl-1H-pyrazolo[3,4-d]pyrimidin-4(5H)-one,
6-(3-fluorophenethyl)-1-methyl-5-phenyl-1H-pyrazolo[3,4-d]pyrimidin-4(5H)-one,
6-(((3-fluorophenyl)amino)methyl)-1-methyl-5-phenyl-1H-pyrazolo[3,4-d]pyrimidin-4(5H)-one,
6-(((3-fluorobenzyl)oxy)methyl)-1-methyl-5-phenyl-1H-pyrazolo[3,4-d]pyrimidin-4(5H)-one,
6-(((3-fluorophenyl)thio)methyl)-1-methyl-5-phenyl-1H-pyrazolo[3,4-d]pyrimidin-4(5H)-one,
1-methyl-6-((2-oxo-2-phenylethyl)thio)-5-phenyl-1H-pyrazolo[3,4-d]pyrimidin-4(5H)-one,
3-(((1-methyl-4-oxo-5-phenyl-4,5-dihydro-1H-pyrazolo[3,4-d]pyrimidin-6-yl)thio)methyl)benzonitrile,
6-((3-methoxybenzyl)thio)-1-methyl-5-phenyl-1H-pyrazolo[3,4-d]pyrimidin-4(5H)-one,
6-(benzylthio)-1-methyl-5-phenyl-1H-pyrazolo[3,4-d]pyrimidin-4(5H)-one,
1-methyl-5-phenyl-6-((3-(2,2,2-trifluoroacetyl)benzyl)thio)-1H-pyrazolo[3,4-d]pyrimidin-4(5H)-one,
3-(((1-methyl-4-oxo-5-phenyl-4,5-dihydro-1H-pyrazolo[3,4-d]pyrimidin-6-yl)thio)methyl)benzaldehyde,
4-(((1-methyl-4-oxo-5-phenyl-4,5-dihydro-1H-pyrazolo[3,4-d]pyrimidin-6-yl)thio)methyl)benzaldehyde,
6-((3-fluorobenzyl)oxy)-1-methyl-5-phenyl-1H-pyrazolo[3,4-d]pyrimidin-4(5H)-one,
1-methyl-5-phenyl-6-((1-phenylethyl)thio)-1H-pyrazolo[3,4-d]pyrimidin-4(5H)-one,
6-(((3-fluorophenyl)(methyl)amino)methyl)-1-methyl-5-phenyl-1H-pyrazolo[3,4-d]pyrimidin-4(5H)-one,
6-((3-fluorobenzyl)oxy)-2-(oxetan-3-ylmethyl)-5-phenyl-2H-pyrazolo[3,4-d]pyrimidin-4(5H)-one,
2-(oxetan-3-ylmethyl)-5-phenyl-6-((1-phenylethyl)thio)-2H-pyrazolo[3,4-d]pyrimidin-4(5H)-one,
(R)-1-methyl-5-phenyl-6-((1-phenylethyl)thio)-1H-pyrazolo[3,4-d]pyrimidin-4(5H)-one,
(S)-1-methyl-5-phenyl-6-((1-phenylethyl)thio)-1H-pyrazolo[3,4-d]pyrimidin-4(5H)-one,
1-methyl-5-phenyl-6-(1-phenylethoxy)-1H-pyrazolo[3,4-d]pyrimidin-4(5H)-one,
6-((3-fluorobenzyl)thio)-2-((3-methyloxetan-3-yl)methyl)-5-phenyl-2H-pyrazolo[3,4-d]pyrimidin-4(5H)-one,
3-((6-((3-fluorobenzyl)thio)-4-oxo-5-phenyl-4,5-dihydro-2H-pyrazolo[3,4-d]pyrimidin-2-yl)methyl)azetidin-1-ium sulfate,
1-methyl-5-phenyl-6-((1-phenylpropyl)thio)-1H-pyrazolo[3,4-d]pyrimidin-4(5H)-one,
6-((1-(3-fluorophenyl)ethyl)thio)-1-methyl-5-phenyl-1H-pyrazolo[3,4-d]pyrimidin-4(5H)-one,
6-(cyclohexylthio)-1-methyl-5-phenyl-1H-pyrazolo[3,4-d]pyrimidin-4(5H)-one,
1-(oxetan-3-yl)-5-phenyl-6-((1-phenylethyl)thio)-1H-pyrazolo[3,4-d]pyrimidin-4(5H)-one,
2-(oxetan-3-yl)-5-phenyl-6-((1-phenylethyl)thio)-2H-pyrazolo[3,4-d]pyrimidin-4(5H)-one,
1-methyl-6-((2-oxocyclopentyl)thio)-5-phenyl-1H-pyrazolo[3,4-d]pyrimidin-4(5H)-one,
1-methyl-6-((2-oxocyclohexyl)thio)-5-phenyl-1H-pyrazolo[3,4-d]pyrimidin-4(5H)-one,
1-methyl-5-phenyl-6-((2-phenylpropan-2-yl)thio)-1H-pyrazolo[3,4-d]pyrimidin-4(5H)-one,
6-((1-(3-hydroxyphenyl)ethyl)thio)-1-methyl-5-phenyl-1H-pyrazolo[3,4-d]pyrimidin-4(5H)-one,
1-methyl-5-phenyl-6-((1-(pyridin-2-yl)ethyl)thio)-1H-pyrazolo[3,4-d]pyrimidin-4(5H)-one, and
1-methyl-5-phenyl-6-((1-(pyridin-3-yl)ethyl)thio)-1H-pyrazolo[3,4-d]pyrimidin-4(5H)-one.

Accordingly, the present invention further provides methods for treating cancer and/or conditions characterized with elevated ALDH activity through administration of therapeutic amounts of one or more the thiopyrimidinone compounds of the invention to a subject suffering from such cancer and/or condition. The methods are not limited to a particular type of cancer. In some embodiments, the cancer is any cancer having elevated ALDH activity (e.g., ALDH1A1, ALDH1A2, ALDH1A3, ALDH2). In some embodiments, the cancer is any cancer having elevated CSC activity related to ALDH activity (e.g., ALDH1A1, ALDH1A2, ALDH1A3, ALDH2). In some embodiments, the cancer is ovarian cancer. In some embodiments, the cancer epithelial ovarian cancer. In some embodiments, administration of the compound results in inhibition of ALDH activity within the cancer cells. In some embodiments, administration of the compound results in inhibition of CSC activity. In some embodiments, administration of the compound results in CSC necroptosis. In some embodiments, administration of the compound results in reduced resistance of the CSC cells to chemotherapies.

In some embodiments, the compound is co-administered with one or more anticancer agents. For example, in some embodiment, the compound is co-administered with one or more of the following chemotherapy drugs: bevacizumab, carboplatin, paclitaxel, cisplatin, topotecan, doxorubicin, epirubicin, and gemcitabine.

Moreover, the present invention provides methods for inhibiting CSC activity in cells through exposing such cells to one or more of the thiopyrimidinone compounds of the present invention. In some embodiments, the thiopyrimidinone compound renders the CSC cells susceptible to necroptosis. In some embodiments, the thiopyrimidinone compound renders the CSC cells less resistant to chemotherapies. In some embodiments, the thiopyrimidinone compound inhibits ALDH activity (e.g., ALDH1A1, ALDH1A2, ALDH1A3, ALDH2) within the CSC cells.

Moreover, the present invention provides methods for inhibiting ALDH activity in cells through exposing such cells to one or more of the thiopyrimidinone compounds of the present invention. In some embodiments, the thiopyrimidinone compound inhibits one or more of ALDH1A1, ALDH1A2, ALDH1A3, and ALDH2 activity.

DEFINITIONS

Figure 1:
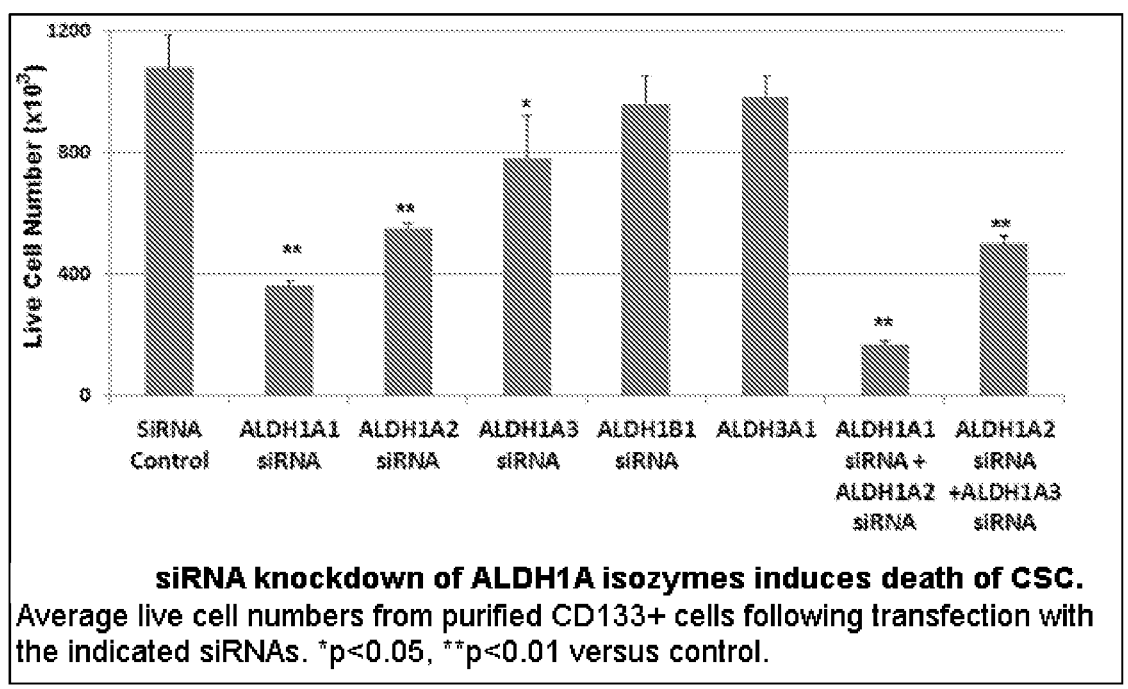
FIG. 1: siRNA knockdown of ALDH1A isozymes induces death of CSC.
Figure 2:
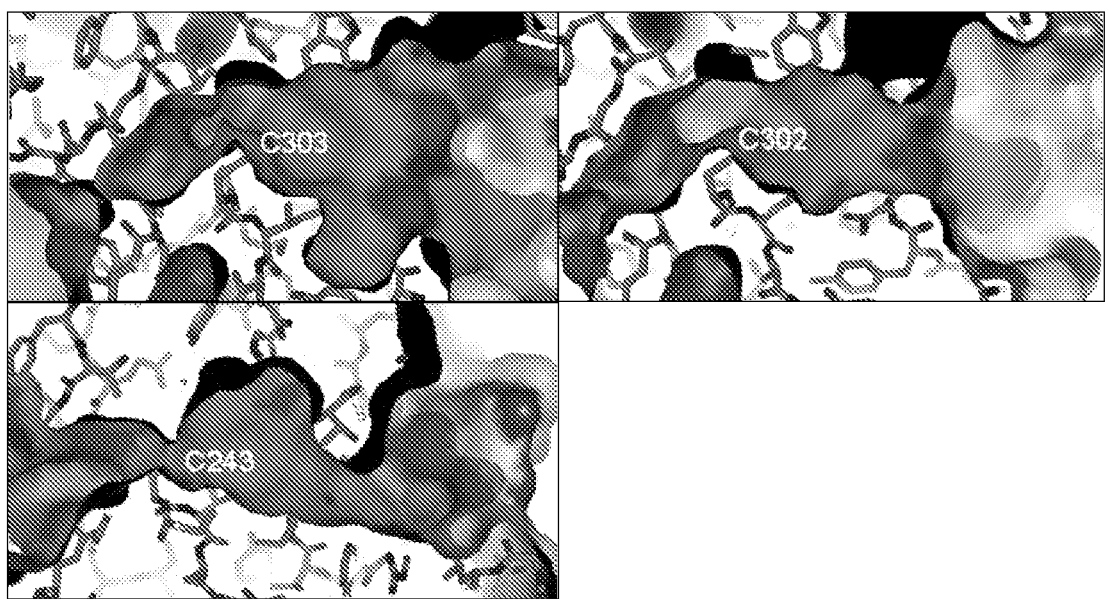
FIG. 2: Comparison of the binding sites of (left to right) ALDH1A1, ALDH2, and ALDH3A1.
Figure 3:
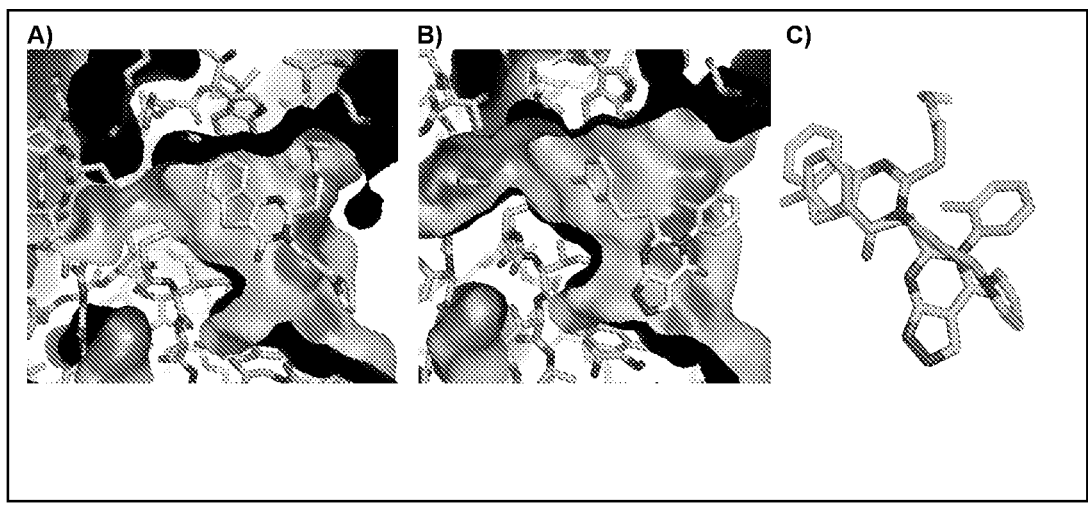
FIG. 3: Structures of CM37 (A) and CM39 (B) complexed with ALDH1A1 at 1.9 and 2.1 angstrom resolution, respectively; (C) overlay of bound structures of CM37 (green) and CM39 (blue).
Figure 4A:
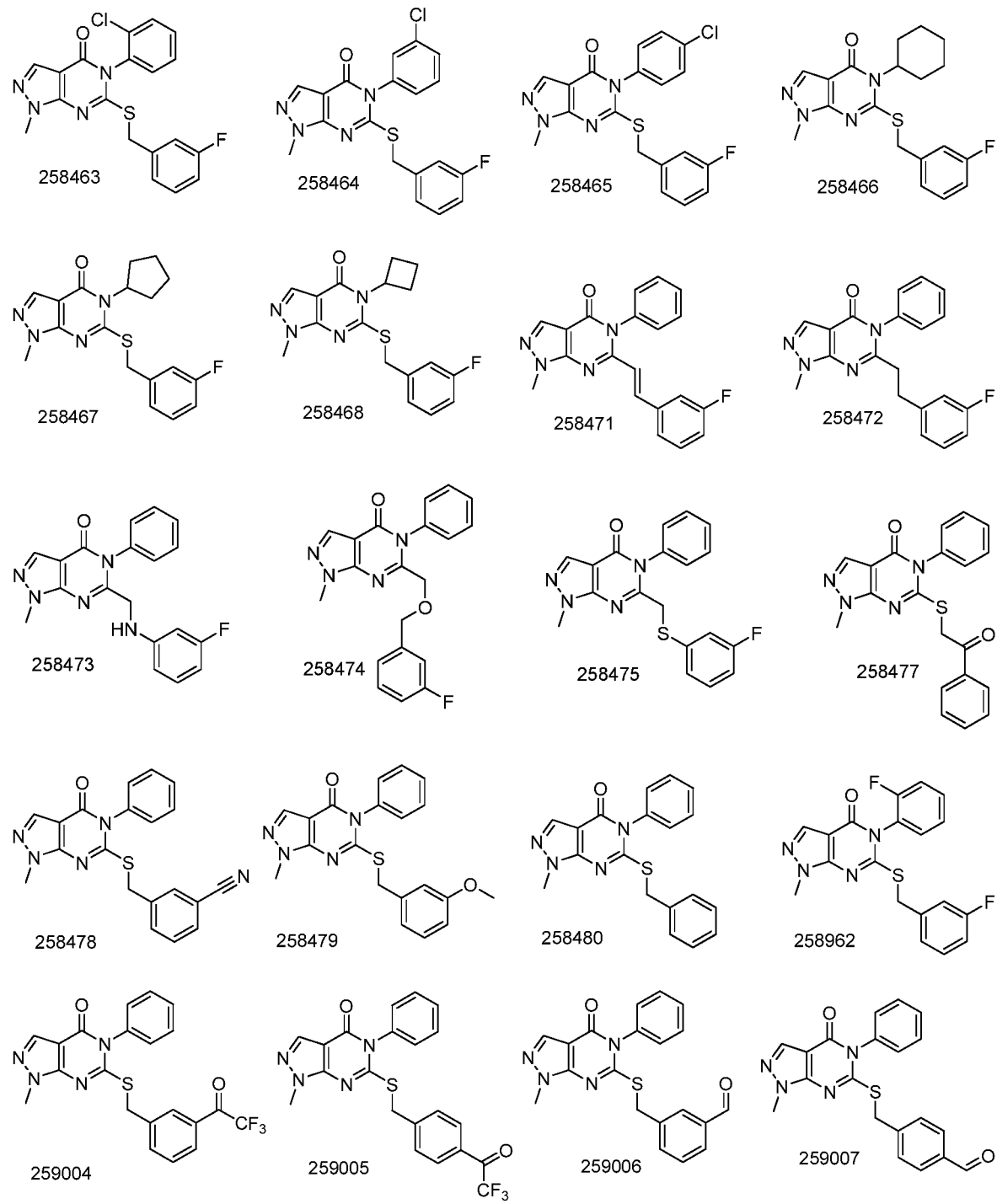
FIGS. 4A and 4B: Compounds encompassed within Formulas I and II.
Figure 4B:
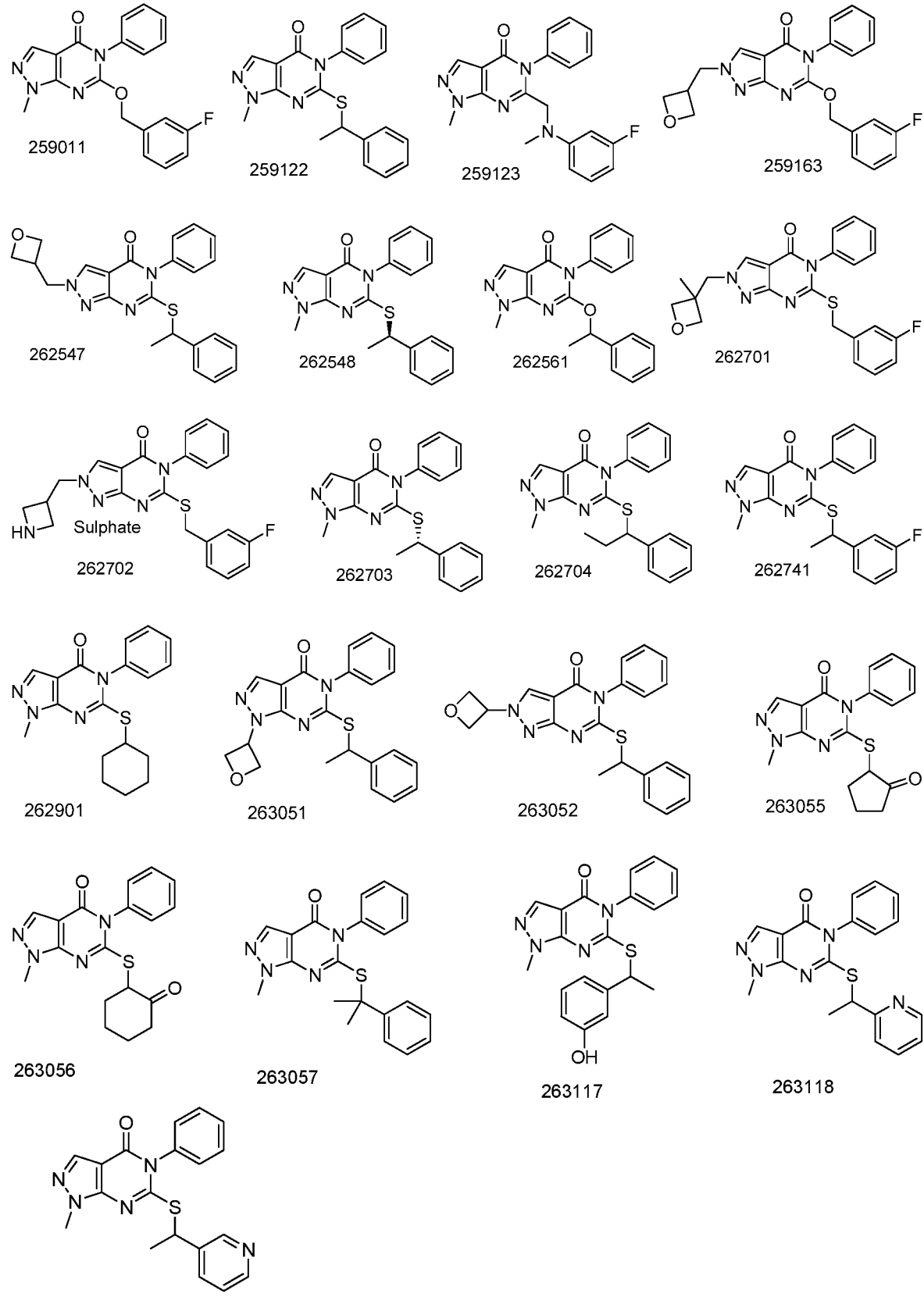

The term "anticancer agent" as used herein, refer to any therapeutic agents (e.g., chemotherapeutic compounds and/or molecular therapeutic compounds), antisense therapies, radiation therapies, or surgical interventions, used in the treatment of hyperproliferative diseases such as cancer (e.g., in mammals, e.g., in humans).

The term "prodrug" as used herein, refers to a pharmacologically inactive derivative of a parent "drug" molecule that requires biotransformation (e.g., either spontaneous or enzymatic) within the target physiological system to release, or to convert (e.g., enzymatically, physiologically, mechanically, electromagnetically) the prodrug into the active drug. Prodrugs are designed to overcome problems associated with stability, water solubility, toxicity, lack of specificity, or limited bioavailability. Exemplary prodrugs comprise an active drug molecule itself and a chemical masking group (e.g., a group that reversibly suppresses the activity of the drug). Some prodrugs are variations or derivatives of compounds that have groups cleavable under metabolic conditions. Prodrugs can be readily prepared from the parent compounds using methods known in the art, such as those described in A Textbook of Drug Design and Development, Krogsgaard-Larsen and H. Bundgaard (eds.), Gordon & Breach, 1991, particularly Chapter 5: "Design and Applications of Prodrugs"; Design of Prodrugs, H. Bundgaard (ed.), Elsevier, 1985; Prodrugs: Topical and Ocular Drug Delivery, K. B. Sloan (ed.), Marcel Dekker, 1998; Methods in Enzymology, K. Widder et al. (eds.), Vol. 42, Academic Press, 1985, particularly pp. 309-396; Burger's Medicinal Chemistry and Drug Discovery, 5th Ed., M. Wolff (ed.), John Wiley & Sons, 1995, particularly Vol. 1 and pp. 172-178 and pp. 949-982; Pro-Drugs as Novel Delivery Systems, T. Higuchi and V. Stella (eds.), Am. Chem. Soc., 1975; and Bioreversible Carriers in Drug Design, E. B. Roche (ed.), Elsevier, 1987.

Exemplary prodrugs become pharmaceutically active in vivo or in vitro when they undergo solvolysis under physiological conditions or undergo enzymatic degradation or other biochemical transformation (e.g., phosphorylation, hydrogenation, dehydrogenation, glycosylation). Prodrugs often offer advantages of water solubility, tissue compatibility, or delayed release in the mammalian organism. (See e.g., Bundgard, Design of Prodrugs, pp. 7-9, 21-24, Elsevier, Amsterdam (1985); and Silverman, The Organic Chemistry of Drug Design and Drug Action, pp. 352-401, Academic Press, San Diego, CA (1992)). Common prodrugs include acid derivatives such as esters prepared by reaction of parent acids with a suitable alcohol (e.g., a lower alkanol) or esters prepared by reaction of parent alcohol with a suitable carboxylic acid, (e.g., an amino acid), amides prepared by reaction of the parent acid compound with an amine, basic groups reacted to form an acylated base derivative (e.g., a lower alkylamide), or phosphorus-containing derivatives, e.g., phosphate, phosphonate, and phosphoramidate esters, including cyclic phosphate, phosphonate, and phosphoramidate (see, e.g., US Patent Application Publication No. US 2007/0249564 A1; herein incorporated by reference in its entirety).

The term "pharmaceutically acceptable salt" as used herein, refers to any salt (e.g., obtained by reaction with an acid or a base) of a compound of the present invention that is physiologically tolerated in the target animal (e.g., a mammal). Salts of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, sulfonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metal (e.g., sodium) hydroxides, alkaline earth metal (e.g., magnesium) hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, chloride, bromide, iodide, 2-hydroxyethanesulfonate, lactate, maleate, mesylate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like. For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

The term "solvate" as used herein, refers to the physical association of a compound of the invention with one or more solvent molecules, whether organic or inorganic. This physical association often includes hydrogen bonding. In certain instances, the solvate is capable of isolation, for example, when one or more solvate molecules are incorporated in the crystal lattice of the crystalline solid. "Solvate" encompasses both solution-phase and isolable solvates. Exemplary solvates include hydrates, ethanolates, and methanolates.

The term "therapeutically effective amount," as used herein, refers to that amount of the therapeutic agent sufficient to result in amelioration of one or more symptoms of a disorder, or prevent advancement of a disorder, or cause regression of the disorder. For example, with respect to the treatment of cancer, in one embodiment, a therapeutically effective amount will refer to the amount of a therapeutic agent that decreases the rate of tumor growth, decreases tumor mass, decreases the number of metastases, increases time to tumor progression, or increases survival time by at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

The terms "sensitize" and "sensitizing," as used herein, refer to making, through the administration of a first agent (e.g., a thiopyrimidinone compound of the invention), an animal or a cell within an animal more susceptible, or more responsive, to the biological effects (e.g., promotion or retardation of an aspect of cellular function including, but not limited to, cell division, cell growth, proliferation, invasion, angiogenesis, necrosis, or apoptosis) of a second agent. The sensitizing effect of a first agent on a target cell can be measured as the difference in the intended biological effect (e.g., promotion or retardation of an aspect of cellular function including, but not limited to, cell growth, proliferation, invasion, angiogenesis, or apoptosis) observed upon the administration of a second agent with and without administration of the first agent. The response of the sensitized cell can be increased by at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 450%, or at least about 500% over the response in the absence of the first agent.

The term "hyperproliferative disease," as used herein, refers to any condition in which a localized population of proliferating cells in an animal is not governed by the usual limitations of normal growth. Examples of hyperproliferative disorders include tumors, neoplasms, lymphomas and the like. A neoplasm is said to be benign if it does not undergo invasion or metastasis and malignant if it does either of these. A "metastatic" cell means that the cell can invade and destroy neighboring body structures. Hyperplasia is a form of cell proliferation involving an increase in cell number in a tissue or organ without significant alteration in structure or function. Metaplasia is a form of controlled cell growth in which one type of fully differentiated cell substitutes for another type of differentiated cell.

The term "neoplastic disease," as used herein, refers to any abnormal growth of cells being either benign (non-cancerous) or malignant (cancerous).

The term "normal cell," as used herein, refers to a cell that is not undergoing abnormal growth or division. Normal cells are non-cancerous and are not part of any hyperproliferative disease or disorder.

The term "anti-neoplastic agent," as used herein, refers to any compound that retards the proliferation, growth, or spread of a targeted (e.g., malignant) neoplasm.

The terms "prevent," "preventing," and "prevention," as used herein, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention.

The term "pharmaceutically acceptable carrier" or "pharmaceutically acceptable vehicle" encompasses any of the standard pharmaceutical carriers, solvents, surfactants, or vehicles. Suitable pharmaceutically acceptable vehicles include aqueous vehicles and nonaqueous vehicles. Standard pharmaceutical carriers and their formulations are described in Remington's Pharmaceutical Sciences, Mack Publishing Co., Easton, PA, 19th ed. 1995.

DETAILED DESCRIPTION OF THE INVENTION

Recurrent ovarian cancer may arise from a chemoresistant subpopulation of cancer cells with stem-like features. The high relapse rate of ovarian cancer after complete clinical remission is consistent with a cancer stem cell model which proposes that rare cancer cells with stem cell-like characteristics (CSC) initiate disease relapse. Agents specifically targeting CSC are reported to have up to 100-fold increase in relative therapeutic efficacy (see, Gupta P B, et al., Cell. 2009; 138(4):645-59). Furthermore, CSC-targeting therapies can reverse resistance to traditional chemotherapeutics (see, Wei X, et al., Proc Natl Acad Sci USA. 2010; 107(44): 18874-9; Shank J J, et al., Gynecol Oncol. 2012; 127(2): 390-7; Burgos-Ojeda D, et al., Mol Cancer Ther. 2015). Importantly, therapy with CSC-targeting agents can prevent cancer recurrence (see, Ginestier C, et al., J Clin Invest. 2010; 120(2):485-97). Taken together, these data strongly suggest that targeting CSC will improve patient outcomes.

Aldehyde dehydrogenase and CD133 are markers of CSC. Aldehyde dehydrogenase (ALDH) enzymatic activity is the most well-supported CSC marker, identifying CSC in many cancers including breast, colon, prostate, pancreatic, liver, and lung cancer (see, Ginestier C, et al., Cell Stem Cell. 2007; 1(5):555-67; Carpentino J E, et al., Cancer research. 2009; 69(20):8208-15; Chen Y-C, et al., Biochemical & Biophysical Research Communications. 2009; 385(3): 307-13; Deng S, et al., PLoS ONE [Electronic Resource] .e10277; Dylla S J, et al., PLoS ONE. 2008; 3(6):e2428; Jiang F, et al., Molecular Cancer Research: MCR. 2009; 7(3):330-8; Ma S, et al., Molecular Cancer Research: MCR. 2008; 6(7):1146-53; Silva I A, et al., Cancer research. 2011; 71(11):3991-4001. Cancer cells which express high levels of ALDH (ALDH$^+$) are resistant to not only chemotherapy but also tyrosine kinase inhibitors (see, Huang C P, et al., Cancer Lett. 2013; 328(1):144-51; Canter R J, et al., BMC Cancer. 2014; 14(756)). ALDH alone, or used in combination with CD133, can be used to identify distinct chemoresistant ovarian CSC (OvCSC) (see, Silva I A, et al., Cancer research. 2011; 71(11):3991-4001; Kryczek I, et al., Int J Cancer. 2012; 130(1):29-39). ALDH$^+$ primary human cells initiate and propagate tumors in mice while cells that do not highly express ALDH (ALDH$^-$) cells do not. Taken together these data support a role for ALDH in serous ovarian CSC.

The exact ALDH isozymes associated with CSC remain unclear. Isolation of ALDH$^+$ OvCSC is based on an enzymatic assay and is not isozyme-specific. There are at least 19 members of the ALDH superfamily in the human genome (see, Koppaka V, et al., Pharmacological reviews. 2012; 64(3):520-39; Muzio G, et al., Free radical biology & medicine. 2012; 52(4):735-46). However, not all isozymes are expressed in cancer, while others, such as ALDH2, are ubiquitously expressed. Three ALDH subfamilies (ALDH1, ALDH2, and ALDH3) are believed to be responsible for the vast majority of measurable ALDH activity. Of these, the ALDH1 and ALDH3 subfamilies have primarily been indicated as markers of CSC. In ovarian cancer, ALDH1A1 is the most highly supported as a CSC marker based on the following: (i) the presence of ALDH1A1$^+$CD133$^+$ cells in patients' primary tumor specimens correlates with poor outcome (see, Flesken-Nikitin A, et al., Nature. 2013; 495 (7440):241-5), (ii) ALDH1A1 is 100-fold upregulated in ovarian cancer cells selected for resistance to either cisplatin or paclitaxel, (iii) siRNA knockdown of ALDH1A1 restores chemosensitivity (see, Landen C N, Jr., et al., Mol Cancer Ther. 2010; 9(12):3186-99), and (iv) ALDH1A1 (and CD133) expressing cells are enriched in residual human tumors and in patient-derived xenografts after chemotherapy (see, Steg A D, et al., Clin Cancer Res. 2012; 18(3):869-81; Meacham C E, and Morrison S J. Nature. 2013; 501(7467): 328-37). Furthermore, ALDH1A1 expression in ovarian cancer and others is regulated by the stem cell regulatory Wnt/β-catenin pathway (see, Cojoc M, et al., Cancer Research. 2015; Yamanaka S. Cell. 2009; 137(1):13-7). The biology of ALDH1 isozymes also argues in favor of a potential role in CSC. ALDH1A isozymes (1A1, 1A2, and 1A3) all metabolize vitamin-A to retinoic acid (RA), thereby indirectly regulating RA-mediated gene transcription (see, Napoli J L, et al., J Steroid Biochem Mol Biol. 1995; 53(1-6):497-502). RA-mediated transcription regulates the expression of hundreds of genes including the core stem cell genes NANOG, SOX2 and OCT4 (see, Balmer J E, and Blomhoff R. J Lipid Res. 2002; 43(11):1773-808).

Inhibition of ALDH represents a potential means for targeting CSC. Based on its CSC-specific expression and important functions, ALDH has been supported as a stem cell-specific therapeutic target (see, Kast R E, and Belda-Iniesta C. Current stem cell research & therapy. 2009; 4(4):314-7). Indeed ALDH1A1 knockdown reduces CSC viability and tumorigenesis and increases chemosensitivity in numerous cancers including melanoma, breast, lung and ovarian cancer (see, Landen C N, Jr., et al., Mol Cancer Ther. 2010; 9(12):3186-99; Yip N C, et al., British journal of cancer. 2011; 104(10):1564-74; Luo Y, et al., Stem cells. 2012; 30(10):2100-13; Duong H Q, et al., International journal of oncology. 2012; 41(3):855-61; Li Z, et al., PLoS One. 2014; 9(3):e92669; Moreb J S, et al., Molecular cancer. 2008; 7(87)). Disulfiram, a potent ALDH2 and ALDH1 inhibitor, has anti-cancer activity in vitro and in animal tumor models (see, Yip N C, et al., British journal of cancer. 2011; 104(10):1564-74; Kast R E, and Belda-Iniesta C. Current stem cell research & therapy. 2009; 4(4):314-7; Irving C C, and Daniel D S. Carcinogenesis. 1987; 8(9): 1309-15; Morrison B W, et al., Melanoma Res. 2010; 20(1): 11-20; Lin J, et al., Prostate. 2011; 71(4):333-43). ALDH activity is required to maintain chemotherapy resistance in CSC in numerous cancers, and disulfiram can reverse this chemotherapy resistance (see, Raha D, et al., Cancer research. 2014). Disulfiram has also been reported to specifically target CSC in breast and brain cancers (see, Yip N C, et al., British journal of cancer. 2011; 104(10):1564-74; Choi S A, et al., Neuro-oncology. 2015; 17(6):810-21) and reverse CSC-linked chemotherapy and radiation resistance (see, Croker A K, and Allan A L. Breast cancer research and treatment. 2012; 133(1):75-87; Wang Y, et al., Oncotarget. 2014; 5(11):3743-55). In contrast, ALDH activators can enhance stem cell activity in normal tissue (see, Banh A, et al., Clin Cancer Res. 2011; 17(23):7265-72).

Significantly, despite its importance in CSC, ALDH1A1 does not appear essential for normal stem cells. ALDH1A1$^{-/-}$ mice are viable with no clear defects (see, Levi B P, et al., Blood. 2009; 113(8):1670-80). ALDH1A1$^{-/-}$ALDH3A1$^{-/-}$ mice are also viable with only modest defects (see, Gasparetto M, et al., Experimental hematology. 2012; 40(4):318-29 e2). Thus, selective ALDH isozyme inhibition is unlikely to impact normal stem cells.

Intriguingly, there is preliminary clinical data to support that ALDH inhibition, even combined with chemotherapy, is both safe and can enhance the survival of cancer patients. A recent Phase IIb trial in patients with advanced lung cancer demonstrated that the addition of disulfiram to chemotherapy improved overall survival with ~10% of patients being disease-free at 3 years (see, Nechushtan H, et al., The Oncologist. 2015; 20(4):366-7). Similarly, in a small study of high-risk breast cancer patients receiving adjuvant chemotherapy and sodium diethyl dithiocarbamic acid (the primary active metabolite of disulfiram (see, Eneanya D I, et al., Annual review of pharmacology and toxicology. 1981; 21(575-96); Agarwal R P, et al., Biochemical pharmacology. 1986; 35(19):3341-7)), there was a trend toward increased overall and disease-free survival (see, Dufour P, et al., Biotherapy. 1993; 6(1):9-12).

Unfortunately disulfiram is not an ideal ALDH inhibitor for the targeting of CSC for several reasons: (i) Disulfiram is not ALDH1-specific, with high affinity for ALDH2 which is not cancer cell specific, (ii) Disulfiram has a very short half-life in vivo and numerous active metabolites (see, Agarwal R P, et al., Biochemical pharmacology. 1986; 35(19):3341-7), and (iii) the multiple metabolites of disulfiram are associated with off-target effects, increasing toxicity and dose-limiting specificity (see, Malcolm R, et al., Expert opinion on drug safety. 2008; 7(4):459-72; Petersen E N. Acta psychiatrica Scandinavica Supplementum. 1992; 369(7-13)). In addition, while such studies with disulfiram confirm that it can partially reverse chemotherapy resistance in ovarian cancer cells, it is not CSC-specific and is less effective than more selective ALDH inhibitors.

Preclinical studies strongly support ALDH inhibition as a means to reverse resistance to not only chemotherapy, but also radiation therapy and tyrosine kinase-targeted therapies. However most studies have used older, nonspecific ALDH inhibitors such as disulfiram and DEAB. Isozyme-specific inhibitors of ALDH are still very rare (see, Koppaka V, et al., Pharmacological reviews. 2012; 64(3):520-39; Canavan H E, et al., J Biomed Mater Res A. 2005; 75(1):1-13). In particular compounds specifically targeting ALDH1A subfamily members, those felt to be critical for CSC function, are lacking.

Experiments conducted during the course of developing embodiments for the present have developed new, isozyme-selective ALDH inhibitors—small-molecule compounds having a thiopyrimidinone structure. Such inhibitors havbe been confirmed as selectively CSC-depleting and co-crystallized with ALDH1A1. Importantly, these compounds are unique in targeting CSC via the induction of necroptosis. Necroptosis is a newly identified form of programmed cell death that can occur when a cell is unable to undergo apoptosis (see, Berghe T V, et al., Nat Rev Mol Cell Biol. 2014; 15(2):135-47). While few compounds are known to induce necroptosis, the activation of necroptosis is a powerful means to overcome cancer cell resistance to apoptosis and chemotherapy resistance (see, Hu X, and Xuan Y, et al., Cancer Lett. 2008; 259(2): 127-37; Perets R, et al., Cancer Cell. 2013; 24(6):751-65; Ohman A W, et al., Front Oncol. 2014; 4(322); Connolly D C, et al., Cancer Res. 2003; 63(6):1389-97; Hedelin M, et al., Cancer epidemiology, biomarkers & prevention: a publication of the American Association for Cancer Research, cosponsored by the American Society of Preventive Oncology. 2011; 20(2):308-17).

Experiments conducted during the course of developing embodiments for the present invention synthesized new class of small-molecules having a thiopyrimidinone structure which function as inhibitors of ALDH protein. Such small-molecules were demonstrated to have optimal IC$_{50}$ values against ALDH (e.g., ALDH1A1, ALDH1A2, ALDH1A3, ALDH2). Such small-molecules were demonstrated to decrease CSC activity in ovarian cancer tumors and ALDH activity (e.g., ALDH1A1, ALDH1A2, ALDH1A3, ALDH2). Such small-molecules were demonstrated to decrease CSC activity in ovarian cancer tumors through a necroptosis mechanism.

As such, the present invention provides novel ALDH inhibitors (small-molecule compounds having a thiopyrimidinone structure) with improved selectivity for the treatment of cancers having a chemotherapy resistance phenotype associated with CSC and/or ALDH activity (e.g., epithelial ovarian cancer).

Accordingly, the present invention relates to compounds which function as inhibitors of ALDH proteins (e.g., ALDH1A1, ALDH1A2, ALDH1A3, ALDH2). By inhibiting the activity of ALDH, these compounds sensitize cells to inducers of CSC necroptosis, apoptosis and/or cell cycle arrest and, in some instances, themselves induce necroptosis, apoptosis and/or cell cycle arrest. Therefore, the invention relates to methods of sensitizing cells to inducers of necroptosis, apoptosis and/or cell cycle arrest and to methods of inducing necroptosis, apoptosis and/or cell cycle arrest in cells, comprising contacting the cells with a compound of the invention alone or in combination with additional agent(s), e.g., an inducer of apoptosis or a cell cycle disrupter.

The invention further relates to methods of treating, ameliorating, or preventing disorders in a patient, such as those that are responsive to induction of necroptosis and/or apoptosis, comprising administering to the patient a compound of the invention and additional agent(s), e.g., an inducer of apoptosis. Such disorders include those characterized by CSC activity, CSC activity related to elevated ALDH activity (e.g., ALDH1A1, ALDH1A2, ALDH1A3, ALDH2), and/or elevated ALDH activity (e.g., ALDH1A1, ALDH1A2, ALDH1A3, ALDH2).

In a particular embodiment, thiopyrimidinone compounds encompassed within Formulas I and II are provided:

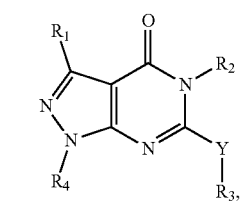

(Formula I)

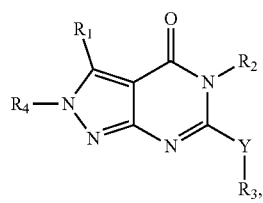

(Formula II)

including pharmaceutically acceptable salts, solvates, and/or prodrugs thereof.

Formulas I and II are not limited to a particular chemical moiety for R1, R2, R3, R4, or Y. In some embodiments, the particular chemical moiety for R1, R2, R3, R4, or Y independently include any chemical moiety that permits the resulting compound to inhibit ALDH activity (e.g., one or more of ALDH1A1, ALDH1A2, ALDH1A3, ALDH2 activity). In some embodiments, the particular chemical moiety for R1, R2, R3, R4, or Y independently include any chemical moiety that permits the resulting compound to inhibit CSC activity. In some embodiments, the particular chemical moiety for R1, R2, R3, R4, or Y independently include any chemical moiety that permits the resulting compound to induce necroptosis (e.g., CSC necroptosis).

In some embodiments, R1 is H or C1-C3 alkyl (substituted or non-substituted). R1 is H, $CH_3$, $CH_2CH_3$, or $CH_2CH_2CH_3$ In some embodiments, R2 is H, C0-C3-alkyl-Ar or C0-C3-alkyl-Heteroaryl, wherein the alkyls are independently substituted or non-substituted. In some embodiments, R2 is phenyl (substituted or non-substituted). In some embodiments, R2 is $CH_3$,

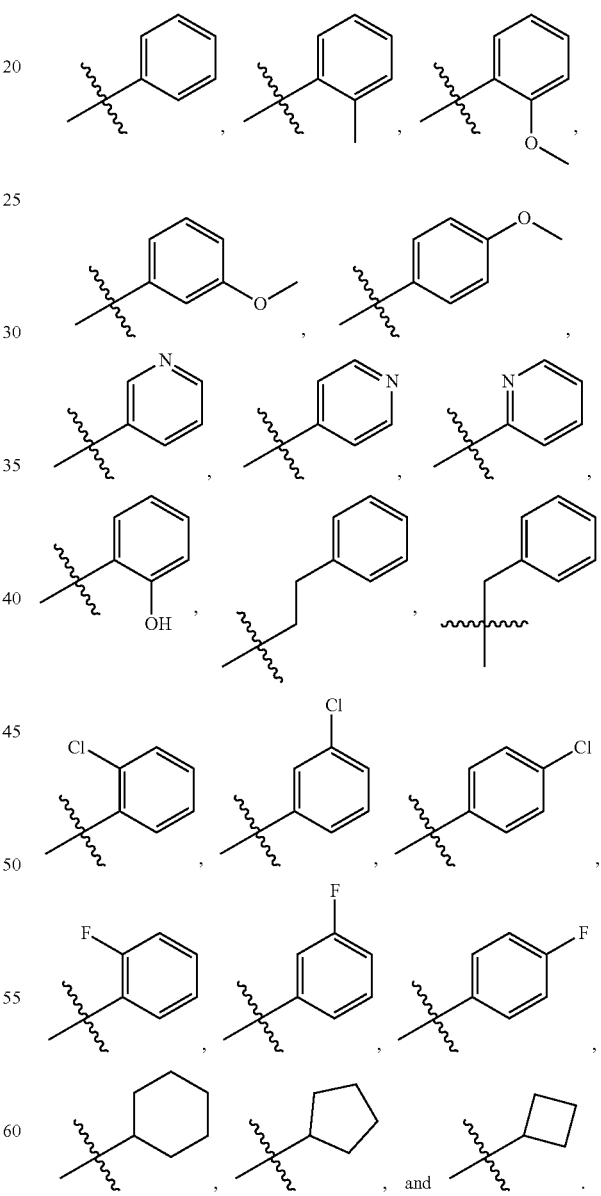

In some embodiments, Y is a linker that is present or absent. In some embodiments wherein Y is present, Y is selected from

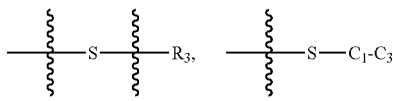

alkyl or alkenyl (substituted or unsubstituted) (branched or unbranched)

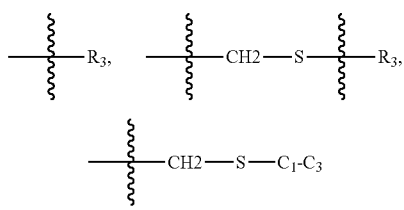

alkyl or alkenyl (substituted or unsubstituted) (branched or unbranched)

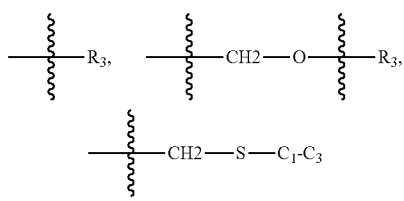

alkyl or alkenyl (substituted or unsubstituted) (branched or unbranched)

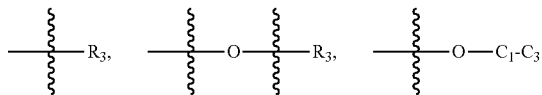

alkyl or alkenyl (substituted or unsubstituted) (branched or unbranched)

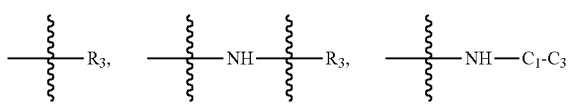

alkyl or alkenyl (substituted or unsubstituted) (branched or unbranched)

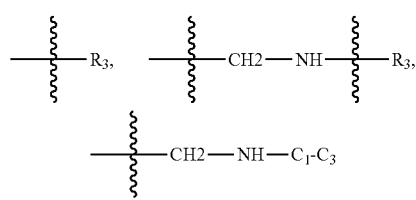

alkyl or alkenyl (substituted or unsubstituted) (branched or unbranched)

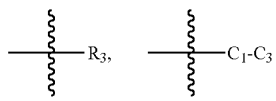

alkyl or alkenyl (substituted or unsubstituted) (branched or unbranched)

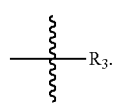

In some embodiments wherein Y is present, Y is selected from

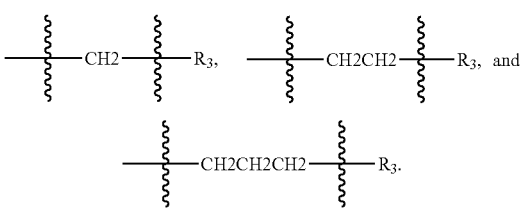

In some embodiments, R3 is H, C0-C8 alkyl, C0-C2-alkyl-Ar or C0-C2-alkyl-heteroaryl, wherein the alkyls are independently substituted or non-substituted. In some embodiments, R3 is C1-alkyl-Aryl or C1-alkyl-heteroaryl. In some embodiments, R3 is $CH_3$,

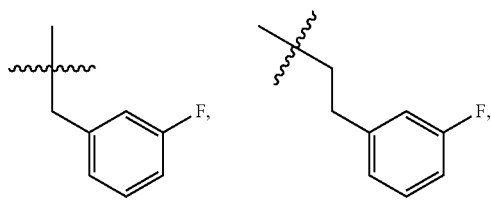

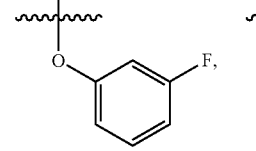

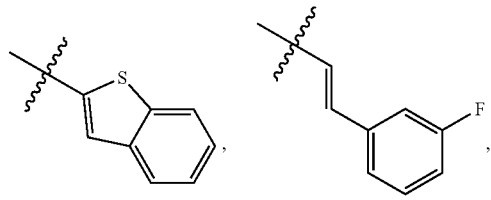

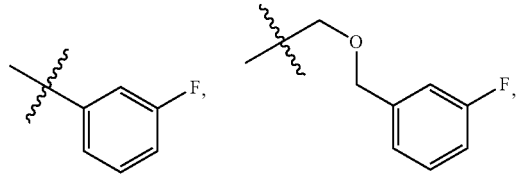

-continued

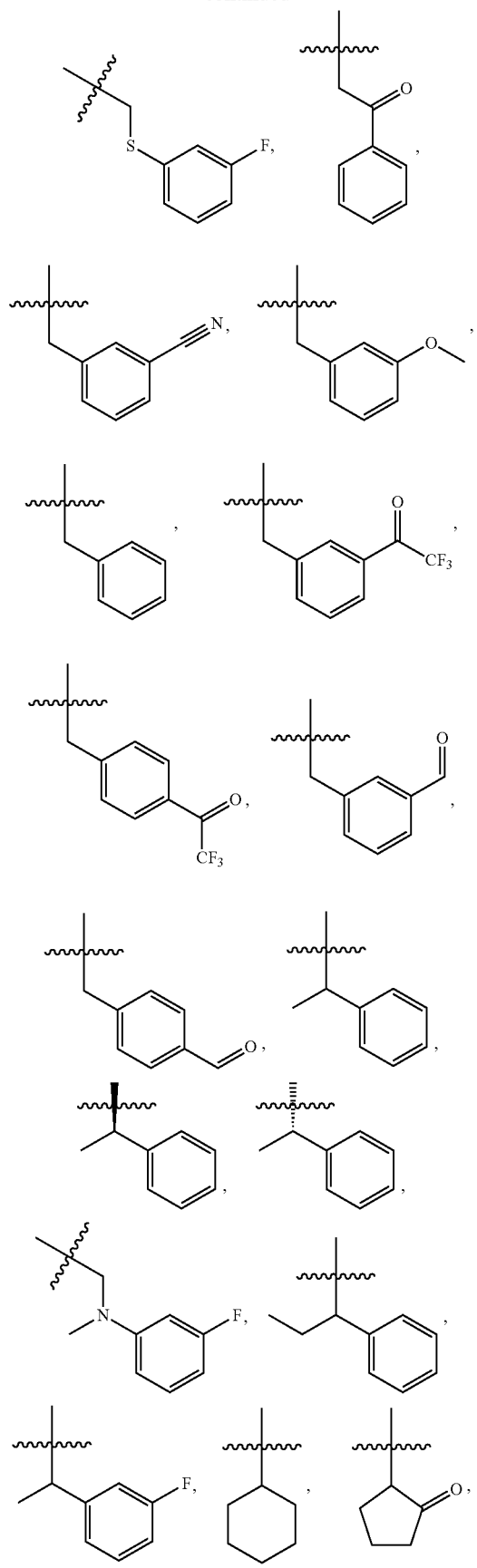

-continued

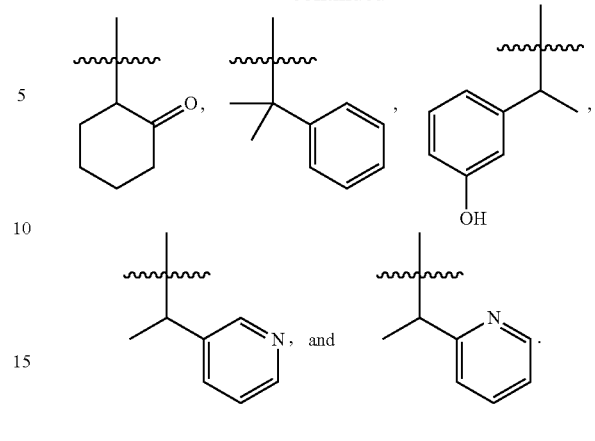

In some embodiments, R4 is H, C1-C6 alkyl or cycloalkyl, optionally substituted and wherein one or more carbons may be replaced by oxygen, wherein the alkyls are independently substituted or non-substituted. In some embodiments, R4H, is C1-C4 alkyl or cycloalkyl, wherein one or more carbons may be replaced by O. In some embodiments, R4 is H, $CH_3$, $CH_2CH_3$,

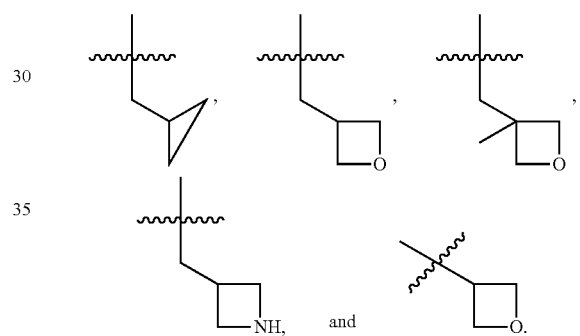

In a particular embodiment, thiopyrimidinone compounds encompassed within Formulas I and II are provided:

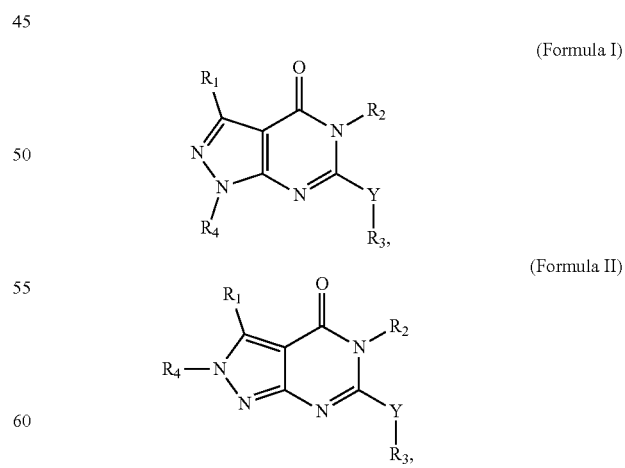

including pharmaceutically acceptable salts, solvates, and/or prodrugs thereof; wherein R1, R2, R3, and Y are defined as above; wherein R4 is H, C1-C6 alkyl or cycloalkyl (optionally substituted or unsubstituted) (wherein one or more carbons may be replaced by oxygen or nitrogen). In some embodiments, R4 is selected from H, CH₃, CH₂CH₃,

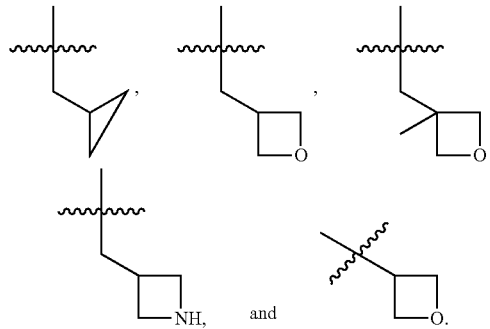

In some embodiments, the following compounds are contemplated for Formulas I and II:
6-((3-fluorobenzyl)thio)-5-(o-tolyl)-1H-pyrazolo[3,4-d]pyrimidin-4(5H)-one,
6-((3-fluorobenzyl)thio)-5-phenyl-1H-pyrazolo[3,4-d]pyrimidin-4(5H)-one,
6-((3-fluorobenzyl)thio)-1-methyl-5-(o-tolyl)-1H-pyrazolo[3,4-d]pyrimidin-4(5H)-one,
6-((3-fluorobenzyl)thio)-2-methyl-5-(o-tolyl)-2H-pyrazolo[3,4-d]pyrimidin-4(5H)-one,
1-ethyl-6-((3-fluorobenzyl)thio)-5-(o-tolyl)-1H-pyrazolo[3,4-d]pyrimidin-4(5H)-one,
2-ethyl-6-((3-fluorobenzyl)thio)-5-(o-tolyl)-2H-pyrazolo[3,4-d]pyrimidin-4(5H)-one,
1-(cyclopropylmethyl)-6-((3-fluorobenzyl)thio)-5-(o-tolyl)-1H-pyrazolo[3,4-d]pyrimidin-4(5H)-one,
2-(cyclopropylmethyl)-6-((3-fluorobenzyl)thio)-5-(o-tolyl)-2H-pyrazolo[3,4-d]pyrimidin-4(5H)-one,
6-((3-fluorobenzyl)thio)-1-(oxetan-3-yl)-5-(o-tolyl)-1H-pyrazolo[3,4-d]pyrimidin-4(5H)-one,
6-((3-fluorobenzyl)thio)-2-(oxetan-3-yl)-5-(o-tolyl)-2H-pyrazolo[3,4-d]pyrimidin-4(5H)-one,
6-((3-fluorobenzyl)thio)-1-(oxetan-3-ylmethyl)-5-(o-tolyl)-1H-pyrazolol[3,4-d]pyrimidin-4(5H)-one,
6-((3-fluorobenzyl)thio)-2-(oxetan-3-ylmethyl)-5-(o-tolyl)-2H-pyrazolo[3,4-d]pyrimidin-4(5H)-one,
6-((3-fluorobenzyl)thio)-2-methyl-5-phenyl-2H-pyrazolo[3,4-d]pyrimidin-4(5H)-one,
1-ethyl-6-((3-fluorobenzyl)thio)-5-phenyl-1H-pyrazolo[3,4-d]pyrimidin-4(5H)-one,
2-ethyl-6-((3-fluorobenzyl)thio)-5-phenyl-2H-pyrazolo[3,4-d]pyrimidin-4(5H)-one,
1-(cyclopropylmethyl)-6-((3-fluorobenzyl)thio)-5-phenyl-1H-pyrazolo[3,4-d]pyrimidin-4(5H)-one,
2-(cyclopropylmethyl)-6-((3-fluorobenzyl)thio)-5-phenyl-2H-pyrazolo[3,4-d]pyrimidin-4(5H)-one,
6-((3-fluorobenzyl)thio)-1-(oxetan-3-yl)-5-phenyl-1H-pyrazolo[3,4-d]pyrimidin-4(5H)-one,
6-((3-fluorobenzyl)thio)-2-(oxetan-3-yl)-5-phenyl-2H-pyrazolo[3,4-d]pyrimidin-4(5H)-one,
6-((3-fluorobenzyl)thio)-1-(oxetan-3-ylmethyl)-5-phenyl-1H-pyrazolo[3,4-d]pyrimidin-4(5H)-one,
6-((3-fluorobenzyl)thio)-2-(oxetan-3-ylmethyl)-5-phenyl-2H-pyrazolo[3,4-d]pyrimidin-4(5H)-one,
6-((3-fluorobenzyl)amino)-5-(o-tolyl)-1H-pyrazolo[3,4-d]pyrimidin-4(5H)-one,
6-((3-fluorophenethyl)amino)-1-methyl-5-(o-tolyl)-1H-pyrazolo[3,4-d]pyrimidin-4(5H)-one,
6-((3-fluorobenzyl)oxy)-1-methyl-5-(o-tolyl)-1H-pyrazolo[3,4-d]pyrimidin-4(5H)-one,
6-((3-fluorophenoxy)methyl)-1-methyl-5-phenyl-1H-pyrazolo[3,4-d]pyrimidin-4(5H)-one,
6-(((3-fluorobenzyl)amino)methyl)-1-methyl-5-phenyl-1H-pyrazolo[3,4-d]pyrimidin-4(5H)-one,
6-((3-fluorobenzyl)thio)-1-methyl-5-phenyl-1H-pyrazolo[3,4-d]pyrimidin-4(5H)-one,
6-((3-fluorobenzyl)thio)-5-(2-methoxyphenyl)-1-methyl-1H-pyrazolo[3,4-d]pyrimidin-4(5H)-one,
6-((3-fluorobenzyl)thio)-5-(3-methoxyphenyl)-1-methyl-1H-pyrazolo[3,4-d]pyrimidin-4(5H)-one,
6-((3-fluorobenzyl)thio)-5-(4-methoxyphenyl)-1-methyl-1H-pyrazolo[3,4-d]pyrimidin-4(5H)-one
6-((3-fluorobenzyl)thio)-1-methyl-5-(pyridin-3-yl)-1H-pyrazolo[3,4-d]pyrimidin-4(5H)-one,
6-((3-fluorobenzyl)thio)-1-methyl-5-(pyridin-4-yl)-1H-pyrazolo[3,4-d]pyrimidin-4(5H)-one,
6-((3-fluorobenzyl)thio)-5-(2-hydroxyphenyl)-1-methyl-1H-pyrazolo[3,4-d]pyrimidin-4(5H)-one,
6-((3-fluorobenzyl)thio)-1-methyl-5-(pyridin-2-yl)-1H-pyrazolo[3,4-d]pyrimidin-4(5H)-one,
6-((3-fluorobenzyl)thio)-1-methyl-5-phenethyl-1H-pyrazolo[3,4-d]pyrimidin-4(5H)-one,
5-benzyl-6-((3-fluorobenzyl)thio)-1-methyl-1H-pyrazolo[3,4-d]pyrimidin-4(5H)-one,
6-((3-fluorobenzyl)thio)-1,5-dimethyl-1H-pyrazolo[3,4-d]pyrimidin-4(5H)-one,
6-(isopentylthio)-1-methyl-5-phenyl-1H-pyrazolo[3,4-d]pyrimidin-4(5H)-one,
6-((3-fluorobenzyl)thio)-3-methyl-5-(o-tolyl)-2H-pyrazolo[3,4-d]pyrimidin-4(5H)-one,
6-(benzo[b]thiophen-2-ylmethoxy)-1-methyl-5-(o-tolyl)-1H-pyrazolo[3,4-d]pyrimidin-4(5H)-one,
5-(2-chlorophenyl)-6-(3-fluorobenzylthio)-1-methyl-1H-pyrazolo[3,4-d]pyrimidin-4(5H)-one,
5-(2-chlorophenyl)-6-((3-fluorobenzyl)thio)-1-methyl-1H-pyrazolo[3,4-d]pyrimidin-4(5H)-one,
5-(3-chlorophenyl)-6-((3-fluorobenzyl)thio)-1-methyl-1H-pyrazolo[3,4-d]pyrimidin-4(5H)-one,
5-(4-chlorophenyl)-6-((3-fluorobenzyl)thio)-1-methyl-1H-pyrazolo[3,4-d]pyrimidin-4(5H)-one,
6-((3-fluorobenzyl)thio)-5-(2-fluorophenyl)-1-methyl-1H-pyrazolo[3,4-d]pyrimidin-4(5H)-one,
5-cyclohexyl-6-((3-fluorobenzyl)thio)-1-methyl-1H-pyrazolo[3,4-d]pyrimidin-4(5H)-one,
5-cyclopentyl-6-((3-fluorobenzyl)thio)-1-methyl-1H-pyrazolo[3,4-d]pyrimidin-4(5H)-one,
5-cyclobutyl-6-((3-fluorobenzyl)thio)-1-methyl-1H-pyrazolo[3,4-d]pyrimidin-4(5H)-one,
(E)-6-(3-fluorostyryl)-1-methyl-5-phenyl-1H-pyrazolo[3,4-d]pyrimidin-4(5H)-one,
6-(3-fluorophenethyl)-1-methyl-5-phenyl-1H-pyrazolo[3,4-d]pyrimidin-4(5H)-one,
6-(((3-fluorophenyl)amino)methyl)-1-methyl-5-phenyl-1H-pyrazolo[3,4-d]pyrimidin-4(5H)-one,
6-(((3-fluorobenzyl)oxy)methyl)-1-methyl-5-phenyl-1H-pyrazolo[3,4-d]pyrimidin-4(5H)-one,
6-(((3-fluorophenyl)thio)methyl)-1-methyl-5-phenyl-1H-pyrazolo[3,4-d]pyrimidin-4(5H)-one,
1-methyl-6-((2-oxo-2-phenylethyl)thio)-5-phenyl-1H-pyrazolo[3,4-d]pyrimidin-4(5H)-one,
3-(((1-methyl-4-oxo-5-phenyl-4,5-dihydro-1H-pyrazolo[3,4-d]pyrimidin-6-yl)thio)methyl)benzonitrile,
6-((3-methoxybenzyl)thio)-1-methyl-5-phenyl-1H-pyrazolo[3,4-d]pyrimidin-4(5H)-one, 6-(benzylthio)-1-methyl-5-phenyl-1H-pyrazolo[3,4-d]pyrimidin-4(5H)-one, 1-methyl-5-phenyl-6-((3-(2,2,2-trifluoroacetyl)benzyl)thio)-1H-pyrazolo[3,4-d]pyrimidin-4(5H)-one, 3-(((1-methyl-4-oxo-5-phenyl-4,5-dihydro-1H-pyrazolo[3,4-d]pyrimidin-6-yl)thio)methyl)benzaldehyde, 4-(((1-methyl-4-oxo-5-phenyl-4,5-dihydro-1H-pyrazolo[3,4-d]pyrimidin-6-yl)thio)methyl)benzaldehyde, 6-((3-fluorobenzyl)oxy)-1-methyl-5-phenyl-1H-pyrazolo[3,4-d]pyrimidin-4(5H)-one, 1-methyl-5-phenyl-6-((1-phenylethyl)thio)-1H-pyrazolo[3,4-d]pyrimidin-4(5H)-one, 6-(((3-fluorophenyl)(methyl)amino)methyl)-1-methyl-5-phenyl-1H-pyrazolo[3,4-d]pyrimidin-4(5H)-one, 6-((3-fluorobenzyl)oxy)-2-(oxetan-3-ylmethyl)-5-phenyl-2H-pyrazolo[3,4-d]pyrimidin-4(5H)-one, 2-(oxetan-3-ylmethyl)-5-phenyl-6-((1-phenylethyl)thio)-2H-pyrazolo[3,4-d]pyrimidin-4(5H)-one, (R)-1-methyl-5-phenyl-6-((1-phenylethyl)thio)-1H-pyrazolo[3,4-d]pyrimidin-4(5H)-one, (S)-1-methyl-5-phenyl-6-((1-phenylethyl)thio)-1H-pyrazolo[3,4-d]pyrimidin-4(5H)-one, 1-methyl-5-phenyl-6-(1-phenylethoxy)-1H-pyrazolo[3,4-d]pyrimidin-4(5H)-one, 6-((3-fluorobenzyl)thio)-2-((3-methyloxetan-3-yl)methyl)-5-phenyl-2H-pyrazolo[3,4-d]pyrimidin-4(5H)-one, 3-((6-((3-fluorobenzyl)thio)-4-oxo-5-phenyl-4,5-dihydro-2H-pyrazolo[3,4-d]pyrimidin-2-yl)methyl)azetidin-1-ium sulfate, 1-methyl-5-phenyl-6-((1-phenylpropyl)thio)-1H-pyrazolo[3,4-d]pyrimidin-4(5H)-one, 6-((1-(3-fluorophenyl)ethyl)thio)-1-methyl-5-phenyl-1H-pyrazolo[3,4-d]pyrimidin-4(5H)-one, 6-(cyclohexylthio)-1-methyl-5-phenyl-1H-pyrazolo[3,4-d]pyrimidin-4(5H)-one, 1-(oxetan-3-yl)-5-phenyl-6-((1-phenylethyl)thio)-1H-pyrazolo[3,4-d]pyrimidin-4(5H)-one, 2-(oxetan-3-yl)-5-phenyl-6-((1-phenylethyl)thio)-2H-pyrazolo[3,4-d]pyrimidin-4(5H)-one, 1-methyl-6-((2-oxocyclopentyl)thio)-5-phenyl-1H-pyrazolo[3,4-d]pyrimidin-4(5H)-one, 1-methyl-6-((2-oxocyclohexyl)thio)-5-phenyl-1H-pyrazolo[3,4-d]pyrimidin-4(5H)-one, 1-methyl-5-phenyl-6-((2-phenylpropan-2-yl)thio)-1H-pyrazolo[3,4-d]pyrimidin-4(5H)-one, 6-((1-(3-hydroxyphenyl)ethyl)thio)-1-methyl-5-phenyl-1H-pyrazolo[3,4-d]pyrimidin-4(5H)-one, 1-methyl-5-phenyl-6-((1-(pyridin-2-yl)ethyl)thio)-1H-pyrazolo[3,4-d]pyrimidin-4(5H)-one, and 1-methyl-5-phenyl-6-((1-(pyridin-3-yl)ethyl)thio)-1H-pyrazolo[3,4-d]pyrimidin-4(5H)-one.

An important aspect of the present invention is that compounds of the invention induce necroptosis, cell cycle arrest and/or apoptosis and also potentiate the induction of cell cycle arrest and/or apoptosis either alone or in response to additional apoptosis induction signals. Therefore, it is contemplated that these compounds sensitize cells to induction of cell cycle arrest and/or apoptosis, including cells that are resistant to such inducing stimuli. The ALDH inhibitors of the present invention (e.g., thiopyrimidinone compounds) can be used to induce CSC necroptosis and/or apoptosis in any disorder that can be treated, ameliorated, or prevented by the inhibition of ALDH activity within such cells. The ALDH inhibitors of the present invention (e.g., thiopyrimidinone compounds) can be used to induce CSC necroptosis and/or apoptosis in any disorder that can be treated, ameliorated, or prevented by the induction of CSC necroptosis and/or apoptosis.

In some embodiments, the compositions and methods of the present invention are used to treat diseased cells, tissues, organs, or pathological conditions and/or disease states in an animal (e.g., a mammalian patient including, but not limited to, humans and veterinary animals). In this regard, various diseases and pathologies are amenable to treatment or prophylaxis using the present methods and compositions. A non-limiting exemplary list of these diseases and conditions includes, but is not limited to, ovarian cancer, ovarian carcinoma, epithelial ovarian cancer, pancreatic cancer, breast cancer, prostate cancer, lymphoma, skin cancer, colon cancer, melanoma, malignant melanoma, brain cancer, primary brain carcinoma, head and neck cancer, glioma, glioblastoma, liver cancer, bladder cancer, non-small cell lung cancer, head or neck carcinoma, breast carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, acute myelogenous leukemia, chronic myelogenous leukemia, chronic granulocytic leukemia, acute granulocytic leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma, and the like, T and B cell mediated autoimmune diseases; inflammatory diseases; infections; hyperproliferative diseases; AIDS; degenerative conditions, vascular diseases, and the like. In some embodiments, the cancer cells being treated are metastatic. In other embodiments, the cancer cells being treated are resistant to anticancer agents. In other embodiments, the disorder is any disorder having cells having elevated ALDH activity. In other embodiments, the disorder is any disorder having cells having CSC activity.

Some embodiments of the present invention provide methods for administering an effective amount of a compound of the invention and at least one additional therapeutic agent (including, but not limited to, chemotherapeutic antineoplastics, apoptosis-modulating agents, antimicrobials, antivirals, antifungals, and anti-inflammatory agents) and/or therapeutic technique (e.g., surgical intervention, and/or radiotherapies). In a particular embodiment, the additional therapeutic agent(s) is an anticancer agent.

A number of suitable anticancer agents are contemplated for use in the methods of the present invention. Indeed, the present invention contemplates, but is not limited to, administration of numerous anticancer agents such as: agents that induce apoptosis; polynucleotides (e.g., anti-sense, ribozymes, siRNA); polypeptides (e.g., enzymes and antibodies); biological mimetics; alkaloids; alkylating agents; antitumor antibiotics; antimetabolites; hormones; platinum compounds; monoclonal or polyclonal antibodies (e.g., antibodies conjugated with anticancer drugs, toxins, defensins), toxins; radionuclides; biological response modifiers (e.g., interferons (e.g., IFN-α) and interleukins (e.g., IL-2)); adoptive immunotherapy agents; hematopoietic growth factors;

agents that induce tumor cell differentiation (e.g., all-trans-retinoic acid); gene therapy reagents (e.g., antisense therapy reagents and nucleotides); tumor vaccines; angiogenesis inhibitors; proteosome inhibitors: NF-KB modulators; anti-CDK compounds; HDAC inhibitors; and the like. Numerous other examples of chemotherapeutic compounds and anticancer therapies suitable for co-administration with the disclosed compounds are known to those skilled in the art.

In certain embodiments, anticancer agents comprise agents that induce or stimulate apoptosis. Agents that induce apoptosis include, but are not limited to, radiation (e.g., X-rays, gamma rays, UV); tumor necrosis factor (TNF)-related factors (e.g., TNF family receptor proteins, TNF family ligands, TRAIL, antibodies to TRAIL-R1 or TRAIL-R2); kinase inhibitors (e.g., epidermal growth factor receptor (EGFR) kinase inhibitor, vascular growth factor receptor (VGFR) kinase inhibitor, fibroblast growth factor receptor (FGFR) kinase inhibitor, platelet-derived growth factor receptor (PDGFR) kinase inhibitor, and Bcr-Abl kinase inhibitors (such as GLEEVEC)); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; staurosporine, and the like.

In still other embodiments, the compositions and methods of the present invention provide a compound of the invention and at least one anti-hyperproliferative or antineoplastic agent selected from alkylating agents, antimetabolites, and natural products (e.g., herbs and other plant and/or animal derived compounds).

Alkylating agents suitable for use in the present compositions and methods include, but are not limited to: 1) nitrogen mustards (e.g., mechlorethamine, cyclophosphamide, ifosfamide, melphalan (L-sarcolysin); and chlorambucil); 2) ethylenimines and methylmelamines (e.g., hexamethylmelamine and thiotepa); 3) alkyl sulfonates (e.g., busulfan); 4) nitrosoureas (e.g., carmustine (BCNU); lomustine (CCNU); semustine (methyl-CCNU); and streptozocin (streptozotocin)); and 5) triazenes (e.g., dacarbazine (DTIC; dimethyltriazenoimid-azolecarboxamide).

In some embodiments, antimetabolites suitable for use in the present compositions and methods include, but are not limited to: 1) folic acid analogs (e.g., methotrexate (amethopterin)); 2) pyrimidine analogs (e.g., fluorouracil (5-fluorouracil; 5-FU), floxuridine (fluorode-oxyuridine; FudR), and cytarabine (cytosine arabinoside)); and 3) purine analogs (e.g., mercaptopurine (6-mercaptopurine; 6-MP), thioguanine (6-thioguanine; TG), and pentostatin (2'-deoxycoformycin)).

In still further embodiments, chemotherapeutic agents suitable for use in the compositions and methods of the present invention include, but are not limited to: 1) vinca alkaloids (e.g., vinblastine (VLB), vincristine); 2) epipodophyllotoxins (e.g., etoposide and teniposide); 3) antibiotics (e.g., dactinomycin (actinomycin D), daunorubicin (daunomycin; rubidomycin), doxorubicin, bleomycin, plicamycin (mithramycin), and mitomycin (mitomycin C)); 4) enzymes (e.g., L-asparaginase); 5) biological response modifiers (e.g., interferon-alfa); 6) platinum coordinating complexes (e.g., cisplatin (cis-DDP) and carboplatin); 7) anthracenediones (e.g., mitoxantrone); 8) substituted ureas (e.g., hydroxyurea); 9) methylhydrazine derivatives (e.g., procarbazine (N-methylhydrazine; MIH)); 10) adrenocortical suppressants (e.g., mitotane (o,p'-DDD) and aminoglutethimide); 11) adrenocorticosteroids (e.g., prednisone); 12) progestins (e.g., hydroxyprogesterone caproate, medroxyprogesterone acetate, and megestrol acetate); 13) estrogens (e.g., diethylstilbestrol and ethinyl estradiol); 14) antiestrogens (e.g., tamoxifen); 15) androgens (e.g., testosterone propionate and fluoxymesterone); 16) antiandrogens (e.g., flutamide): and 17) gonadotropin-releasing hormone analogs (e.g., leuprolide).

Any oncolytic agent that is routinely used in a cancer therapy context finds use in the compositions and methods of the present invention. For example, the U.S. Food and Drug Administration maintains a formulary of oncolytic agents approved for use in the United States. International counterpart agencies to the U.S.F.D.A. maintain similar formularies. Table 1 provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 1

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N'',N''-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole | Arimidex | AstraZeneca |

TABLE 1-continued

| | | |
|---|---|---|
| (1,3-Benzenediacetonitrile, a,a,a',a'-tetramethyl-5-(1H-1,2,4-triazol-1-ylmethyl)) | | Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (Bacillus Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin $A_2$ and bleomycin $B_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |

TABLE 1-continued

| | | |
|---|---|---|
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |

TABLE 1-continued

| | | |
|---|---|---|
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3', 4':6,7] indolizino[1,2-b] quinoline-3,14(4H, 12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl-1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Mechlorethamine, nitrogen mustard (2-chloro-N-(2-chloroethyl)-N-methylethanamine hydrochloride) | Mustargen | Merck |
| Megestrol acetate 17α(acetyloxy)-6-methylpregna-4,6-diene-3,20-dione | Megace | Bristol-Myers Squibb |
| Melphalan, L-PAM (4-[bis(2-chloroethyl) amino]-L-phenylalanine) | Alkeran | GlaxoSmithKline |
| Mercaptopurine, 6-MP (1,7-dihydro-6H-purine-6-thione monohydrate) | Purinethol | GlaxoSmithKline |
| Mesna (sodium 2-mercaptoethane sulfonate) | Mesnex | Asta Medica |
| Methotrexate (N-[4-[[(2,4-diamino-6-pteridinyl)methyl]methylamino]benzoyl]-L-glutamic acid) | Methotrexate | Lederle Laboratories |
| Methoxsalen (9-methoxy-7H-furo[3,2-g][1]-benzopyran-7-one) | Uvadex | Therakos, Inc., Way Exton, Pa |
| Mitomycin C | Mutamycin | Bristol-Myers Squibb |
| mitomycin C | Mitozytrex | SuperGen, Inc., Dublin, CA |
| Mitotane (1,1-dichloro-2-(o-chlorophenyl)-2-(p-chlorophenyl) ethane) | Lysodren | Bristol-Myers Squibb |
| Mitoxantrone (1,4-dihydroxy-5,8-bis[[2-[(2-hydroxyethyl)amino]ethyl]amino]-9,10-anthracenedione dihydrochloride) | Novantrone | Immunex Corporation |
| Nandrolone phenpropionate | Durabolin-50 | Organon, Inc., West Orange, NJ |
| Nofetumomab | Verluma | Boehringer Ingelheim Pharma KG, Germany |
| Oprelvekin (IL-11) | Neumega | Genetics Institute, Inc., Alexandria, VA |
| Oxaliplatin (cis-[(1R,2R)-1,2-cyclohexanediamine-N,N'] [oxalato(2-)-O,O'] platinum) | Eloxatin | Sanofi Synthelabo, Inc., NY, NY |
| Paclitaxel (5β, 20-Epoxy-1,2a, 4,7β, 10β, 13a-hexahydroxytax-11-en-9-one 4,10-diacetate 2-benzoate 13-ester with (2R, 3 S)-N-benzoyl-3-phenylisoserine) | TAXOL | Bristol-Myers Squibb |

TABLE 1-continued

| | | |
|---|---|---|
| Pamidronate (phosphonic acid (3-amino-1-hydroxypropylidene) bis-, disodium salt, pentahydrate, (APD)) | Aredia | Novartis |
| Pegademase ((monomethoxypolyethylene glycol succinimidyl) 11-17-adenosine deaminase) | Adagen (Pegademase Bovine) | Enzon Pharmaceuticals, Inc., Bridgewater, NJ |
| Pegaspargase (monomethoxypolyethylene glycol succinimidyl L-asparaginase) | Oncaspar | Enzon |
| Pegfilgrastim (covalent conjugate of recombinant methionyl human G-CSF (Filgrastim) and monomethoxypolyethylene glycol) | Neulasta | Amgen, Inc |
| Pentostatin | Nipent | Parke-Davis Pharmaceutical Co., Rockville, MD |
| Pipobroman | Vercyte | Abbott Laboratories, Abbott Park, IL |
| Plicamycin, Mithramycin (antibiotic produced by *Streptomyces plicatus*) | Mithracin | Pfizer, Inc., NY, NY |
| Porfimer sodium | Photofrin | QLT Phototherapeutics, Inc., Vancouver, Canada |
| Procarbazine (N-isopropyl-μ-(2-methylhydrazino)-p-toluamide monohydrochloride) | Matulane | Sigma Tau Pharmaceuticals, Inc., Gaithersburg, MD |
| Quinacrine (6-chloro-9-(1-methyl-4-diethyl-amine) butylamino-2-methoxyacridine) | Atabrine | Abbott Labs |
| Rasburicase (recombinant peptide) | Elitek | Sanofi-Synthelabo, Inc., |
| Rituximab (recombinant anti-CD20 antibody) | Rituxan | Genentech, Inc., South San Francisco, CA |
| Sargramostim (recombinant peptide) | Prokine | Immunex Corp |
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6H-purine-6-thione) | Thioguanine | GlaxoSmithKline |
| Thiotepa (Aziridine,1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |

TABLE 1-continued

| | | |
|---|---|---|
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxy]]-2-naphthacenyl]-2-oxoethyl pentanoate) | Valstar | Anthra --> Medeva |
| Vinblastine, Leurocristine ($C_{46}H_{56}N_4O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

Anticancer agents further include compounds which have been identified to have anticancer activity. Examples include, but are not limited to, 3-AP, 12-O-tetradecanoylphorbol-13-acetate, 17AAG, 852A, ABI-007, ABR-217620, ABT-751, ADI-PEG 20, AE-941, AG-013736, AGRO100, alanosine, AMG 706, antibody G250, antineoplastons, AP23573, apaziquone, APC8015, atiprimod, ATN-161, atrasenten, azacitidine, BB-10901, BCX-1777, bevacizumab, BG00001, bicalutamide, BMS 247550, bortezomib, bryostatin-1, buserelin, calcitriol, CCI-779, CDB-2914, cefixime, cetuximab, CG0070, cilengitide, clofarabine, combretastatin A4 phosphate, CP-675,206, CP-724, 714, CpG 7909, curcumin, decitabine, DENSPM, doxercalciferol, E7070, E7389, ecteinascidin 743, efaproxiral, eflornithine, EKB-569, enzastaurin, erlotinib, exisulind, fenretinide, flavopiridol, fludarabine, flutamide, fotemustine, FR901228, G17DT, galiximab, gefitinib, genistein, glufosfamide, GTI-2040, histrelin, HKI-272, homoharringtonine, HSPPC-96, hu14.18-interleukin-2 fusion protein, HuMax-CD4, iloprost, imiquimod, infliximab, interleukin-12, IPI-504, irofulven, ixabepilone, lapatinib, lenalidomide, lestaurtinib, leuprolide, LMB-9 immunotoxin, lonafarnib, luniliximab, mafosfamide, MB07133, MDX-010, MLN2704, monoclonal antibody 3F8, monoclonal antibody J591, motexafin, MS-275, MVA-MUC1-IL2, nilutamide, nitrocamptothecin, nolatrexed dihydrochloride, nolvadex, NS-9, O6-benzylguanine, oblimersen sodium, ONYX-015, oregovomab, OSI-774, panitumumab, paraplatin, PD-0325901, pemetrexed, PHY906, pioglitazone, pirfenidone, pixantrone, PS-341, PSC 833, PXD101, pyrazoloacridine, R115777, RAD001, ranpirnase, rebeccamycin analogue, rhuAngiostatin protein, rhuMab 2C4, rosiglitazone, rubitecan, S-1, S-8184, satraplatin, SB-, 15992, SGN-0010, SGN-40, sorafenib, SR31747A, ST1571, SU011248, suberoylanilide hydroxamic acid, suramin, talabostat, talampanel, tariquidar, temsirolimus, TGFa-PE38 immunotoxin, thalidomide, thymalfasin, tipifarnib, tirapazamine, TLK286, trabectedin, trimetrexate glucuronate, TroVax, UCN-1, valproic acid, vinflunine, VNP40101M, volociximab, vorinostat, VX-680, ZD1839, ZD6474, zileuton, and zosuquidar trihydrochloride.

For a more detailed description of anticancer agents and other therapeutic agents, those skilled in the art are referred to any number of instructive manuals including, but not limited to, the Physician's Desk Reference and to Goodman and Gilman's "Pharmaceutical Basis of Therapeutics" tenth edition, Eds. Hardman et al., 2002.

The present invention provides methods for administering a compound of the invention with radiation therapy. The invention is not limited by the types, amounts, or delivery and administration systems used to deliver the therapeutic dose of radiation to an animal. For example, the animal may receive photon radiotherapy, particle beam radiation therapy, other types of radiotherapies, and combinations thereof. In some embodiments, the radiation is delivered to the animal using a linear accelerator. In still other embodiments, the radiation is delivered using a gamma knife.

The source of radiation can be external or internal to the animal. External radiation therapy is most common and involves directing a beam of high-energy radiation to a tumor site through the skin using, for instance, a linear accelerator. While the beam of radiation is localized to the tumor site, it is nearly impossible to avoid exposure of normal, healthy tissue. However, external radiation is usually well tolerated by animals. Internal radiation therapy involves implanting a radiation-emitting source, such as beads, wires, pellets, capsules, particles, and the like, inside the body at or near the tumor site including the use of delivery systems that specifically target cancer cells (e.g., using particles attached to cancer cell binding ligands). Such implants can be removed following treatment, or left in the body inactive. Types of internal radiation therapy include, but are not limited to, brachytherapy, interstitial irradiation, intracavity irradiation, radioimmunotherapy, and the like.

The animal may optionally receive radiosensitizers (e.g., metronidazole, misonidazole, intra-arterial Budr, intravenous iododeoxyuridine (IudR), nitroimidazole, 5-substituted-4-nitroimidazoles, 2H-isoindolediones, [[(2-bromoethyl)-amino]methyl]-nitro-1H-imidazole-1-ethanol, nitroaniline derivatives, DNA-affinic hypoxia selective cytotoxins, halogenated DNA ligand, 1,2,4 benzotriazine oxides, 2-nitroimidazole derivatives, fluorine-containing nitroazole derivatives, benzamide, nicotinamide, acridine-intercalator, 5-thiotretrazole derivative, 3-nitro-1,2,4-triazole, 4,5-dinitroimidazole derivative, hydroxylated texaphrins, cisplatin, mitomycin, tiripazamine, nitrosourea, mercaptopurine, methotrexate, fluorouracil, bleomycin, vincristine, carboplatin, epirubicin, doxorubicin, cyclophosphamide, vindesine, etoposide, paclitaxel, heat (hyperthermia), and the like), radioprotectors (e.g., cysteamine, aminoalkyl dihydrogen phosphorothioates, amifostine (WR 2721), IL-1, IL-6, and the like). Radiosensitizers enhance the killing of tumor cells. Radioprotectors protect healthy tissue from the harmful effects of radiation.

Any type of radiation can be administered to an animal, so long as the dose of radiation is tolerated by the animal without unacceptable negative side-effects. Suitable types of radiotherapy include, for example, ionizing (electromagnetic) radiotherapy (e.g., X-rays or gamma rays) or particle beam radiation therapy (e.g., high linear energy radiation). Ionizing radiation is defined as radiation comprising particles or photons that have sufficient energy to produce ionization, i.e., gain or loss of electrons (as described in, for example, U.S. Pat. No. 5,770,581 incorporated herein by reference in its entirety). The effects of radiation can be at least partially controlled by the clinician. In one embodiment, the dose of radiation is fractionated for maximal target cell exposure and reduced toxicity.

In one embodiment, the total dose of radiation administered to an animal is about 0.01 Gray (Gy) to about 100 Gy. In another embodiment, about 10 Gy to about 65 Gy (e.g., about 15 Gy, 20 Gy, 25 Gy, 30 Gy, 35 Gy, 40 Gy, 45 Gy, 50 Gy, 55 Gy, or 60 Gy) are administered over the course of treatment. While in some embodiments a complete dose of radiation can be administered over the course of one day, the total dose is ideally fractionated and administered over several days. Desirably, radiotherapy is administered over the course of at least about 3 days, e.g., at least 5, 7, 10, 14, 17, 21, 25, 28, 32, 35, 38, 42, 46, 52, or 56 days (about 1-8 weeks). Accordingly, a daily dose of radiation will comprise approximately 1-5 Gy (e.g., about 1 Gy, 1.5 Gy, 1.8 Gy, 2 Gy, 2.5 Gy, 2.8 Gy, 3 Gy, 3.2 Gy, 3.5 Gy, 3.8 Gy, 4 Gy, 4.2 Gy, or 4.5 Gy), or 1-2 Gy (e.g., 1.5-2 Gy). The daily dose of radiation should be sufficient to induce destruction of the targeted cells. If stretched over a period, in one embodiment, radiation is not administered every day, thereby allowing the animal to rest and the effects of the therapy to be realized. For example, radiation desirably is administered on 5 consecutive days, and not administered on 2 days, for each week of treatment, thereby allowing 2 days of rest per week. However, radiation can be administered 1 day/week, 2 days/week, 3 days/week, 4 days/week, 5 days/week, 6 days/week, or all 7 days/week, depending on the animal's responsiveness and any potential side effects. Radiation therapy can be initiated at any time in the therapeutic period. In one embodiment, radiation is initiated in week 1 or week 2, and is administered for the remaining duration of the therapeutic period. For example, radiation is administered in weeks 1-6 or in weeks 2-6 of a therapeutic period comprising 6 weeks for treating, for instance, a solid tumor. Alternatively, radiation is administered in weeks 1-5 or weeks 2-5 of a therapeutic period comprising 5 weeks. These exemplary radiotherapy administration schedules are not intended, however, to limit the present invention.

In some embodiments of the present invention, a compound of the invention and one or more therapeutic agents or anticancer agents are administered to an animal under one or more of the following conditions: at different periodicities, at different durations, at different concentrations, by different administration routes, etc. In some embodiments, the compound is administered prior to the therapeutic or anticancer agent, e.g., 0.5, 1, 2, 3, 4, 5, 10, 12, or 18 hours, 1, 2, 3, 4, 5, or 6 days, or 1, 2, 3, or 4 weeks prior to the administration of the therapeutic or anticancer agent. In some embodiments, the compound is administered after the therapeutic or anticancer agent, e.g., 0.5, 1, 2, 3, 4, 5, 10, 12, or 18 hours, 1, 2, 3, 4, 5, or 6 days, or 1, 2, 3, or 4 weeks after the administration of the anticancer agent. In some embodiments, the compound and the therapeutic or anticancer agent are administered concurrently but on different schedules, e.g., the compound is administered daily while the therapeutic or anticancer agent is administered once a week, once every two weeks, once every three weeks, or once every four weeks. In other embodiments, the compound is administered once a week while the therapeutic or anticancer agent is administered daily, once a week, once every two weeks, once every three weeks, or once every four weeks.

Compositions within the scope of this invention include all compositions wherein the compounds of the present invention are contained in an amount which is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for disorders responsive to induction of apoptosis. In one embodiment, about 0.01 to about 25 mg/kg is orally administered to treat, ameliorate, or prevent such disorders. For intramuscular injection, the dose is generally about one-half of the oral dose. For example, a suitable intramuscular dose would be about 0.0025 to about 25 mg/kg, or from about 0.01 to about 5 mg/kg.

The unit oral dose may comprise from about 0.01 to about 1000 mg, for example, about 0.1 to about 100 mg of the compound. The unit dose may be administered one or more times daily as one or more tablets or capsules each containing from about 0.1 to about 10 mg, conveniently about 0.25 to 50 mg of the compound or its solvates.

In a topical formulation, the compound may be present at a concentration of about 0.01 to 100 mg per gram of carrier. In a one embodiment, the compound is present at a concentration of about 0.07-1.0 mg/ml, for example, about 0.1-0.5 mg/ml, and in one embodiment, about 0.4 mg/ml.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. The preparations, particularly those preparations which can be administered orally or topically and which can be used for one type of administration, such as tablets, dragees, slow release lozenges and capsules, mouth rinses and mouth washes, gels, liquid suspensions, hair rinses, hair gels, shampoos and also preparations which can be administered rectally, such as suppositories, as well as suitable solutions for administration by intravenous infusion, injection, topically or orally, contain from about 0.01 to 99 percent, in one embodiment from about 0.25 to 75 percent of active compound(s), together with the excipient.

The pharmaceutical compositions of the invention may be administered to any patient which may experience the beneficial effects of the compounds of the invention. Foremost among such patients are mammals, e.g., humans, although the invention is not intended to be so limited. Other patients include veterinary animals (cows, sheep, pigs, horses, dogs, cats and the like).

The compounds and pharmaceutical compositions thereof may be administered by any means that achieve their intended purpose. For example, administration may be by parenteral, subcutaneous, intravenous, intramuscular, intraperitoneal, transdermal, buccal, intrathecal, intracranial, intranasal or topical routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings which, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropylmethylcellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are in one embodiment dissolved or suspended in suitable liquids, such as fatty oils, or liquid paraffin. In addition, stabilizers may be added.

Possible pharmaceutical preparations which can be used rectally include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400. Aqueous injection suspensions may contain substances which increase the viscosity of the suspension include, for example, sodium carboxymethyl cellulose, sorbitol, and/or dextran. Optionally, the suspension may also contain stabilizers.

The topical compositions of this invention are formulated in one embodiment as oils, creams, lotions, ointments and the like by choice of appropriate carriers. Suitable carriers include vegetable or mineral oils, white petrolatum (white soft paraffin), branched chain fats or oils, animal fats and high molecular weight alcohol (greater than $C_{12}$). The carriers may be those in which the active ingredient is soluble. Emulsifiers, stabilizers, humectants and antioxidants may also be included as well as agents imparting color or fragrance, if desired. Additionally, transdermal penetration enhancers can be employed in these topical formulations. Examples of such enhancers can be found in U.S. Pat. Nos. 3,989,816 and 4,444,762; each herein incorporated by reference in its entirety.

Ointments may be formulated by mixing a solution of the active ingredient in a vegetable oil such as almond oil with warm soft paraffin and allowing the mixture to cool. A typical example of such an ointment is one which includes about 30% almond oil and about 70% white soft paraffin by weight. Lotions may be conveniently prepared by dissolving the active ingredient, in a suitable high molecular weight alcohol such as propylene glycol or polyethylene glycol.

One of ordinary skill in the art will readily recognize that the foregoing represents merely a detailed description of certain preferred embodiments of the present invention. Various modifications and alterations of the compositions and methods described above can readily be achieved using expertise available in the art and are within the scope of the invention.

EXAMPLES

The following examples are illustrative, but not limiting, of the compounds, compositions, and methods of the present invention. Other suitable modifications and adaptations of the variety of conditions and parameters normally encountered in clinical therapy and which are obvious to those skilled in the art are within the spirit and scope of the invention.

Example I

This example describes the synthesis technique for thiopyrimidinone compounds of the present invention.

Preparation 1

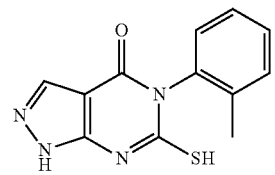 [SMILES: Cc1ccccc1-n1c(S)nc2[nH]ncc2c1=O]

6-mercapto-5-(o-tolyl)-1H-pyrazolo[3,4-d]pyrimidin-4(5H)-one

A solution of o-toluyl isothiocyanate (1.725 mL, 12.89 mmol), and ethyl 5-amino-1H-pyrazole-4-carboxylate (2 g, 12.89 mmol) in 15 mL toluene was refluxed under nitrogen for 3 hours. The mixture was allowed to cool to RT and the precipitate that formed was collected by filtration. The precipitate was added to 10 mL 1N NaOH and refluxed for 3 hours. The mixture was acidified with conc. HCl and the precipitate collected yielding the titled compound as a white solid (1.45 g, 5.61 mmol, 44% yield). $^1$H NMR (400 MHz, DMSO-$d_6$) δ 13.77 (br. s., 1H), 13.41 (br. s., 1H), 8.57 (br. s., 1H), 7.19-7.31 (m, 3H), 7.09 (d, J=5.87 Hz, 1H), 1.99 (s, 3H)

Sub-Example 1: CCG-232820

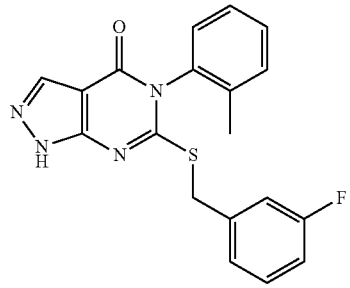 [SMILES: Cc1ccccc1-n1c(SCc2cccc(F)c2)nc2[nH]ncc2c1=O]

6-((3-fluorobenzyl)thio)-5-(o-tolyl)-1H-pyrazolo[3,4-d]pyrimidin-4(5H)-one

To a dry flask under nitrogen charged with 6-mercapto-5-(o-tolyl)-1H-pyrazolo[3,4-d]pyrimidin-4(5H)-one (1.46 g, 5.65 mmol) and potassium carbonate (1.562 g, 11.30 mmol) was added 10 mL DMF followed by 3-fluorobenzyl bromide (0.693 mL, 5.65 mmol). The mixture was stirred at 40° C. for 3 hours. When the reaction was complete by TLC, 10 mL 1N HCl was added followed by 50 mL water. The aqueous portion was extracted 2× with 50 mL ethyl acetate. The combined organics were subsequently washed with brine and dried over sodium sulfate. Removal of volatiles yielded a viscous yellow oil. Trituration with diethyl ether afforded the titled compound as a white crystalline solid (1.26 g, 3.44 mmol, 61% yield). MS (ESI): m/z 367.1 [M+H]$^+$. $^1$H NMR (500 MHz, CDCl$_3$) δ 8.40 (br. s, 1H), 8.15 (s, 1H), 7.40 (t, J=8.30 Hz, 1H), 7.34 (d, J=7.83 Hz, 1H), 7.31 (t, J=7.83 Hz, 1H), 7.21 (t, J=7.80 Hz, 1H), 7.18 (d, J=7.83 Hz, 1H), 7.07 (d, J=7.34 Hz, 1H), 7.02 (d, J=9.29 Hz, 1H), 6.90 (dt, J=1.96, 8.56 Hz, 1H), 4.28 (d, J=13.69 Hz, 1H), 4.31 (d, J=13.69 Hz, 1H), 2.10 (s, 3H) $^{13}$C NMR (126 MHz, CDCl$_3$) δ 162.7, 161.6, 157.8, 153.7, 138.3, 137.0, 135.7, 134.5, 131.5, 130.5, 130.1, 129.4, 127.4, 124.9, 116.1, 114.6, 102.9, 50.6, 17.3

Preparation 2

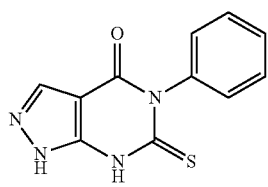 [SMILES: O=c1c2cn[nH]c2[nH]c(=S)n1-c1ccccc1]

5-phenyl-6-thioxo-6,7-dihydro-1H-pyrazolo[3,4-d]pyrimidin-4(5H)-one

A solution of phenyl isothiocyanate (0.770 mL, 6.45 mmol) and ethyl 5-amino-1H-pyrazole-4-carboxylate (1 g, 6.45 mmol) in 10 mL toluene was refluxed under nitrogen overnight. The mixture was allowed to cool to RT and the precipitate that formed was collected by filtration. The precipitate was added to 10 mL aq. 1N NaOH and refluxed for 3 hours. The mixture was acidified with conc. HCl and the precipitate collected yielding the titled compound as a white solid (1 g, 4.09 mmol, 64% yield).

Sub-Example 2: CCG-257901

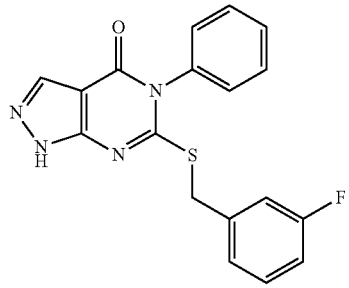 [SMILES: O=c1c2cn[nH]c2nc(SCc2cccc(F)c2)n1-c1ccccc1]

6-((3-fluorobenzyl)thio)-5-phenyl-1H-pyrazolo[3,4-d]pyrimidin-4(5H)-one

Potassium carbonate (1.154 g, 8.35 mmol), 5-phenyl-6-thioxo-6,7-dihydro-1H-pyrazolo[3,4-d]pyrimidin-4(5H)-one (1.02 g, 4.18 mmol), 1-(bromomethyl)-3-fluorobenzene (0.513 mL, 4.18 mmol) and 5 mL DMF were added to a dry flask and stirred overnight under nitrogen. The reaction was neutralized with Sat. Aq. NH$_4$Cl and the mixture was diluted with water and extracted 2× with EtOAc. The combined organic portions were washed 3× with brine and then dried with sodium sulfate and the solvent removed. The crude was purified by flash (0-100% EtOAc in Hex) yielding the titled compound as a white solid (1.02 g, 2.89 mmol, 69% yield). MS (ESI): m/z 353.0867 [M+H]$^+$. $^1$H NMR (400 MHz, CDCl$_3$) δ 12.54 (br. s., 1H), 8.08 (s, 1H), 7.47 (s, 3H), 7.30 (s, 2H), 7.14-7.22 (m, 1H), 7.06 (d, J=7.83 Hz, 1H), 7.02 (d, J=9.39 Hz, 1H), 6.89 (t, J=8.60 Hz, 1H), 4.22-4.35 (m, 2H), $^{13}$C NMR (101 MHz, CDCl$_3$) δ 162.6, 161.6, 158.5, 153.4, 138.3, 135.4, 130.1, 130.0, 129.8, 129.4, 125.0, 116.2, 114.6, 102.9, 36.8

General Procedure A

To a dry flask charged with 6-((3-fluorobenzyl)thio)-5-(o-tolyl)-1H-pyrazolo[3,4-d]pyrimidin-4(5H)-one or 6-((3-fluorobenzyl)thio)-5-phenyl-1H-pyrazolo[3,4-d]pyrimidin-4(5H)-one (0.273 mmol) and potassium carbonate (0.546 mmol) under nitrogen was added 2 mL DMF and the appropriate alkyl halide or mesylate (0.341 mmol) by syringe. The mixture was heated to 50 C overnight at which point starting material was consumed by HPLC. The mixture was diluted with ethyl acetate and washed with water and 3× with brine. The organic portion was dried over sodium sulfate and the solvent removed. The isomers were separated by flash (EtOAc in Hex gradient). The 1-alkyl pyrazoles eluted more quickly than the 2-alkyl pyrazoles. Sub-Examples 3-21 were all prepared by this general procedure.

Sub-Example 3: CCG: 257128

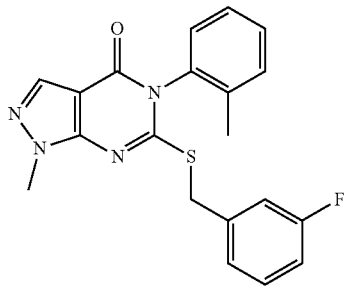 [SMILES: Cc1ccccc1-n1c(SCc2cccc(F)c2)nc2c(cnn2C)c1=O]

6-((3-fluorobenzyl)thio)-1-methyl-5-(o-tolyl)-1H-pyrazolo[3,4-d]pyrimidin-4(5H)-one White solid. (45 mg, 0.118 mmol, 43.3% yield) MS (ESI): m/z 380.9 [M+H]$^+$ $^1$H NMR (400 MHz, DMSO-d$_6$) δ 8.06 (s, 1H), 7.41 (dt, J=1.20, 6.40 Hz, 2H), 7.31-7.38 (m, 2H), 7.23-7.31 (m, 3H), 7.06 (tt, J=1.60, 8.60 Hz, 1H), 4.38 (d, J=13.30 Hz, 1H), 4.43 (d, J=13.30 Hz, 1H), 3.96 (s, 3H), 1.95 (s, 3H) $^{13}$C NMR (101 MHz, DMSO-d$_6$) δ 163.6, 161.3, 156.7, 150.9, 140.3, 136.8, 135.3, 135.1, 131.7, 130.9, 130.3, 128.0, 125.9, 116.4, 114.5, 110.0, 102.7, 35.8, 34.3, 17.2.

Sub-Example 4: CCG: 257432

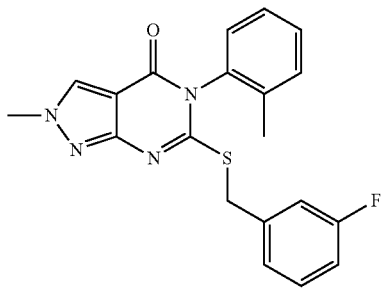 [SMILES: Cc1ccccc1-n1c(SCc2cccc(F)c2)nc2nn(C)cc2c1=O]

6-((3-fluorobenzyl)thio)-2-methyl-5-(o-tolyl)-2H-pyrazolo[3,4-d]pyrimidin-4(5H)-one Colorless Oil. (28 mg, 0.074 mmol, 27.0% yield) MS (ESI): m/z 381.1 [M+H]$^+$ $^1$H NMR (500 MHz, CDCl$_3$) δ 8.03 (s, 1H), 7.40 (t, J=7.58 Hz, 1H), 7.29-7.36 (m, 2H), 7.19-7.25 (m, 1H), 7.17 (d, J=7.83 Hz, 1H), 7.13 (d, J=7.83 Hz, 1H), 7.07 (d, J=9.78 Hz, 1H), 6.91 (dt, J=2.00, 8.30 Hz, 1H), 4.33-4.42 (m, 2H), 4.07 (s, 3H), 2.10 (s, 3H) $^{13}$C NMR (126 MHz, CDCl$_3$) δ 162.6, 159.9, 158.4, 158.0, 138.7, 137.1, 134.5, 131.3, 130.3, 129.9, 129.6, 129.3, 127.2, 124.9, 116.1, 114.3, 104.9, 40.3, 36.6, 17.3

Sub-Example 5: CCG: 257433

1-ethyl-6-((3-fluorobenzyl)thio)-5-(o-tolyl)-1H-pyrazolo[3,4-d]pyrimidin-4(5H)-one White solid (52 mg, 0.132 mmol, 48.3% yield) MS (ESI): m/z 395.1 [M+H]$^+$ $^1$H NMR (400 MHz, CDCl$_3$) δ 8.04 (s, 1H), 7.42 (t, J=7.70 Hz, 1H), 7.30-7.39 (m, 2H), 7.25 (s, 1H), 7.16 (d, J=7.83 Hz, 1H), 7.13 (d, J=7.83 Hz, 1H), 7.09 (d, J=9.78 Hz, 1H), 6.94 (dt, J=1.57, 8.41 Hz, 1H), 4.41 (q, J=7.04 Hz, 2H), 4.26-4.36 (m, 2H), 2.11 (s, 3H), 1.53 (t, J=7.24 Hz, 3H) $^{13}$C NMR (101 MHz, CDCl$_3$) δ 162.7, 161.0, 157.2, 150.4, 138.8, 137.0, 135.4, 134.6, 131.4, 130.4, 130.1, 129.4, 127.4, 124.6, 116.0, 114.5, 102.9, 42.4, 36.6, 17.4, 15.0 No

Sub-Example 6: CCG: 257434

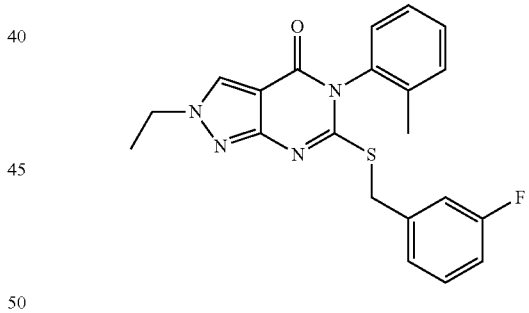

2-ethyl-6-((3-fluorobenzyl)thio)-5-(o-tolyl)-2H-pyrazolo[3,4-d]pyrimidin-4(5H)-one Colorless oil (30 mg, 0.076 mmol, 27.9% yield) MS (ESI): m/z 395.1 [M+H]$^+$ $^1$H NMR (400 MHz, CDCl$_3$) δ 8.08 (s, 1H), 7.41 (t, J=7.40 Hz, 1H), 7.28-7.37 (m, 2H), 7.19-7.26 (m, 1H), 7.17 (d, J=7.83 Hz, 1H), 7.12 (d, J=7.83 Hz, 1H), 7.06 (d, J=9.78 Hz, 1H), 6.91 (t, J=8.41 Hz, 1H), 4.40 (s, 2H), 4.33 (q, J=7.43 Hz, 2H), 2.11 (s, 3H), 1.61 (t, J=7.43 Hz, 3H) $^{13}$C NMR (101 MHz, CDCl$_3$) δ 162.7, 159.9, 158.3, 158.2, 138.7, 137.2, 134.6, 131.3, 130.3, 130.0, 129.6, 127.9, 127.3, 125.0, 116.2, 114.4, 104.6, 48.6, 36.7, 17.4, 15.4

49

Sub-Example 7: CCG: 257724

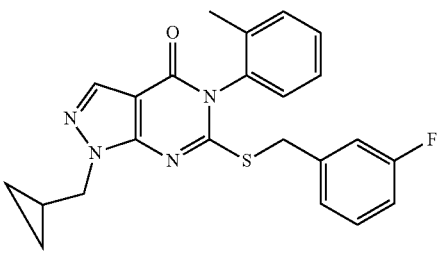 [SMILES: Cc1ccccc1-n1c(SCc2cccc(F)c2)nc2c(cnn2CC2CC2)c1=O]

1-(cyclopropylmethyl)-6-((3-fluorobenzyl)thio)-5-(o-tolyl)-1H-pyrazolo[3,4-d]pyrimidin-4(5H)-one Colorless oil (29.4 mg, 0.070 mmol, 32.0% yield) MS (ESI): m/z 421.1493 [M+H]$^+$ $^1$H NMR (500 MHz, CDCl$_3$) δ 8.05 (s, 1H), 7.42 (t, J=7.80 Hz, 1H), 7.31-7.39 (m, 2H), 7.21-7.28 (m, 1H), 7.17 (d, J=7.34 Hz, 1H), 7.12 (d, J=7.83 Hz, 1H), 7.07 (d, J=9.78 Hz, 1H), 6.94 (dt, J=2.20, 8.44 Hz, 1H), 4.32 (d, J=13.69 Hz, 1H), 4.29 (d, J=14.18 Hz, 1H), 4.19 (d, J=7.20 Hz, 2H), 2.12 (s, 3H), 1.32-1.44 (m, 1H), 0.62 (td, J=5.50, 7.80 Hz, 2H), 0.44 (dt, J=4.80, 5.50 Hz, 2H) $^{13}$C NMR (126 MHz, CDCl$_3$) δ 162.7, 161.1, 157.2, 150.6, 138.7, 137.0, 135.4, 134.6, 131.5, 130.4, 130.1, 129.4, 127.4, 124.5, 115.9, 114.6, 102.9, 52.1, 36.6, 17.4, 11.2, 4.1

Sub-Example 8: CCG: 257725

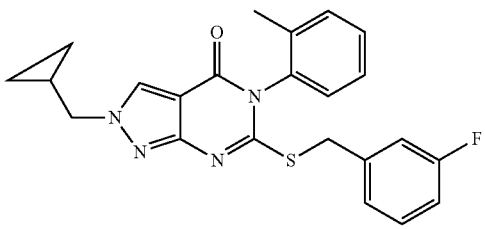 [SMILES: Cc1ccccc1-n1c(SCc2cccc(F)c2)nc2nn(CC3CC3)cc2c1=O]

2-(cyclopropylmethyl)-6-((3-fluorobenzyl)thio)-5-(o-tolyl)-2H-pyrazolo[3,4-d]pyrimidin-4(5H)-one White Crystalline solid (35 mg, 0.083 mmol, 38.1% yield) MS (ESI): m/z 421.1492 [M+H]$^+$ 1H NMR (500 MHz, CDCl$_3$) δ 8.21 (s, 1H), 7.40 (t, J=7.34 Hz, 1H), 7.28-7.36 (m, 2H), 7.19-7.25 (m, 1H), 7.17 (d, J=7.83 Hz, 1H), 7.12 (d, J=7.83 Hz, 1H), 7.06 (d, J=9.78 Hz, 1H), 6.91 (t, J=8.31 Hz, 1H), 4.41 (d, J=14.18 Hz, 1H), 4.38 (d, J=14.20 Hz, 1H), 4.13 (d, J=6.85 Hz, 2H), 2.12 (s, 3H), 1.36-1.47 (m, 1H), 0.69-0.78 (m, 2H), 0.42-0.49 (m, 2H) $^{13}$C NMR (126 MHz, CDCl$_3$) δ 162.7, 159.8, 158.3, 158.2, 138.7, 137.2, 134.6, 131.3, 130.3, 130.0, 129.7, 127.9, 127.3, 125.0, 116.2, 114.4, 104.6, 58.3, 36.7, 17.4, 10.8, 4.3

50

Sub-Example 9: CCG: 257911

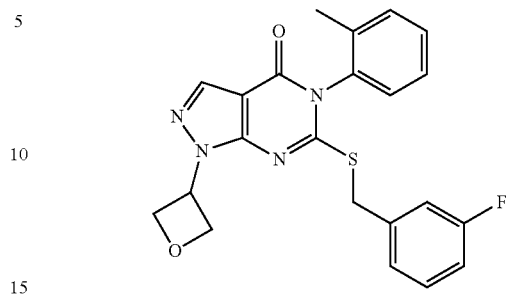

6-((3-fluorobenzyl)thio)-1-(oxetan-3-yl)-5-(o-tolyl)-1H-pyrazolo[3,4-d]pyrimidin-4(5H)-one White solid (21 mg, 0.050 mmol, 18.21% yield) MS (ESI): m/z 423.1282 [M+H]$^+$ $^1$H NMR (500 MHz, CDCl$_3$) δ 8.14 (s, 1H), 7.41-7.46 (m, 1H), 7.32-7.39 (m, 2H), 7.24-7.29 (m, 1H), 7.11-7.17 (m, 2H), 7.06-7.10 (m, 1H), 6.95 (dt, J=2.20, 8.44 Hz, 1H), 5.91-5.99 (m, 1H), 5.28-5.35 (m, 2H), 5.04-5.09 (m, 2H), 4.30 (d, J=13.69 Hz, 1H), 4.34 (d, J=13.69 Hz, 1H), 2.10 (s, 1H) $^{13}$C NMR (126 MHz, CDCl$_3$) δ 162.7, 161.9, 156.9, 151.1, 138.3, 136.9, 136.4, 134.4, 131.5, 130.6, 130.1, 129.3, 127.5, 124.6, 115.9, 114.7, 103.4, 76.9, 50.7, 36.6, 17.3

Sub-Example 10: CCG: 257913

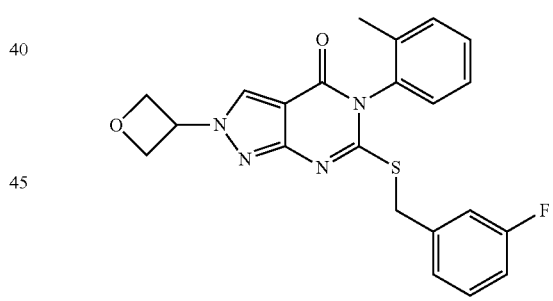

6-((3-fluorobenzyl)thio)-2-(oxetan-3-yl)-5-(o-tolyl)-2H-pyrazolo[3,4-d]pyrimidin-4(5H)-one White solid (17 mg, 0.040 mmol, 14.74% yield) MS (ESI): m/z 423.1285 [M+H]$^+$ $^1$H NMR (500 MHz, CDCl$_3$) δ 8.21 (s, 1H), 7.39-7.45 (m, 1H), 7.30-7.37 (m, 2H), 7.23 (dt, J=5.87, 7.83 Hz, 1H), 7.15-7.19 (m, 1H), 7.12 (d, J=7.83 Hz, 1H), 7.04-7.09 (m, 1H), 6.92 (dt, J=1.96, 8.56 Hz, 1H), 5.53-5.62 (m, 1H), 5.23 (t, J=6.60 Hz, 2H), 5.10 (t, J=7.34 Hz, 2H), 4.38-4.46 (m, 2H), 2.11 (s, 3H) $^{13}$C NMR (126 MHz, CDCl$_3$) δ 162.7, 160.9, 158.6, 157.9, 138.4, 137.1, 134.4, 131.4, 130.4, 130.0, 129.6, 128.1, 127.3, 125.0, 116.2, 114.5, 105.3, 76.8, 56.8, 36.9, 17.4

51

Sub-Example 11: CCG: 257910

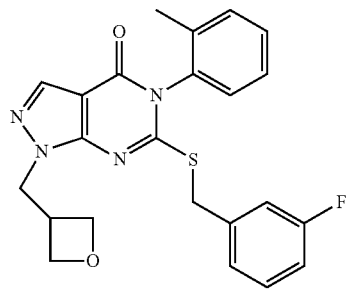 [SMILES: Cc1ccccc1-n1c(SCc2cccc(F)c2)nc2c(cnn2CC2COC2)c1=O]

6-((3-fluorobenzyl)thio)-1-(oxetan-3-ylmethyl)-5-(o-tolyl)-1H-pyrazolo[3,4-d]pyrimidin-4(5H)-one White crystalline solid (50 mg, 0.115 mmol, 42.0% yield) MS (ESI): m/z 437.1449 [M+H]+ $^1$H NMR (500 MHz, CDCl$_3$) δ 8.03 (s, 1H), 7.42-7.47 (m, 1H), 7.33-7.40 (m, 2H), 7.25-7.31 (m, 1H), 7.17 (d, J=7.34 Hz, 1H), 7.14 (d, J=7.34 Hz, 1H), 7.06-7.11 (m, 1H), 6.97 (dt, J=2.45, 8.31 Hz, 1H), 4.86 (dt, J=1.47, 7.09 Hz, 2H), 4.59-4.66 (m, 4H), 4.35 (d, J=13.69 Hz, 1H), 4.31 (d, J=14.18 Hz, 1H), 3.52-3.61 (m, 1H), 2.12 (s, 3H) $^{13}$C NMR (126 MHz, CDCl$_3$) δ 162.7, 161.8, 157.0, 151.1, 138.5, 137.0, 135.9, 134.5, 131.5, 130.5, 130.1, 129.3, 127.5, 124.6, 115.9, 114.6, 102.9, 74.9, 49.5, 36.7, 35.3, 17.4

Sub-Example 12: CCG: 257912

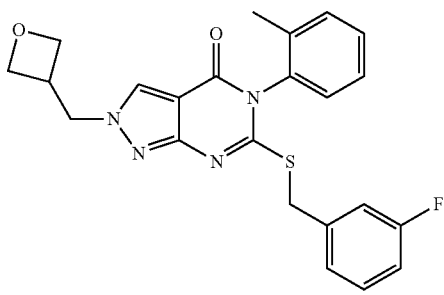 [SMILES: Cc1ccccc1-n1c(SCc2cccc(F)c2)nc2nn(CC3COC3)cc2c1=O]

6-((3-fluorobenzyl)thio)-2-(oxetan-3-ylmethyl)-5-(o-tolyl)-2H-pyrazolo[3,4d]pyrimidin-4(5H)-one Colorless oil (29 mg, 0.066 mmol, 24.34% yield) MS (ESI): m/z 437.1449 [M+H]+ $^1$H NMR (500 MHz, CDCl$_3$) δ 8.07 (s, 1H), 7.38-7.44 (m, 1H), 7.29-7.37 (m, 2H), 7.22 (dt, J=6.11, 7.95 Hz, 1H), 7.16 (d, J=7.34 Hz, 1H), 7.10 (d, J=7.83 Hz, 1H), 7.05 (dd, J=1.96, 9.78 Hz, 1H), 6.91 (dt, J=2.45, 8.31 Hz, 1H), 4.88 (t, J=7.09 Hz, 2H), 4.59 (d, J=7.83 Hz, 2H), 4.55 (t, J=6.36 Hz, 2H), 4.35-4.43 (m, 2H), 3.62-3.71 (m, 1H), 2.11 (s, 3H) $^{13}$C NMR (126 MHz, CDCl$_3$) δ 162.7, 160.5, 158.6, 158.0, 138.5, 137.2, 134.5, 131.4, 130.4, 130.0, 129.6, 128.7, 127.3, 124.9, 116.2, 114.5, 104.9, 74.5, 55.9, 36.8, 35.4, 17.4

52

Sub-Example 13: CCG: 257902

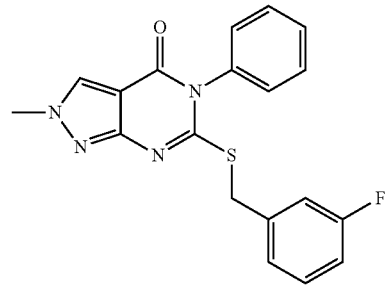 [SMILES: Cn1cc2c(=O)n(-c3ccccc3)c(SCc3cccc(F)c3)nc2n1]

6-((3-fluorobenzyl)thio)-2-methyl-5-phenyl-2H-pyrazolo[3,4-d]pyrimidin-4(5H)-one White solid (20 mg, 0.055 mmol, 24.04% yield). MS (ESI): m/z 367.1021 [M+H]+ $^1$H NMR (500 MHz, CDCl$_3$) δ 8.02 (s, 1H), 7.46-7.56 (m, 3H), 7.26-7.31 (m, 2H), 7.23 (q, J=7.34 Hz, 1H), 7.14 (d, J=7.83 Hz, 1H), 7.08 (d, J=9.29 Hz, 1H), 6.92 (t, J=8.07 Hz, 1H), 4.39 (s, 2H), 4.07 (s, 3H) $^{13}$C NMR (126 MHz, CDCl$_3$) δ 162.7, 159.9, 158.6, 158.3, 138.7, 135.6, 130.0, 130.0, 129.6, 129.6, 129.3, 125.0, 116.2, 114.4, 105.0, 40.3, 37.0

Sub-Example 14: CCG: 257904

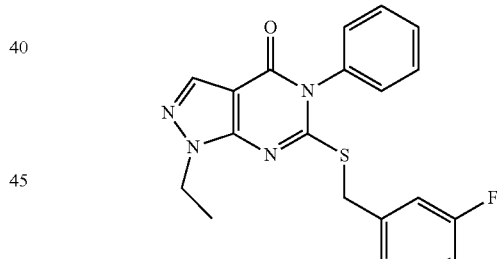

1-ethyl-6-((3-fluorobenzyl)thio)-5-phenyl-1H-pyrazolo[3,4-d]pyrimidin-4(5H)-one

White Solid (43 mg, 0.113 mmol, 49.8% yield) MS (ESI): m/z 381.1175 [M+H]+ $^1$H NMR (400 MHz, CDCl$_3$) δ 8.06 (s, 1H), 7.46-7.56 (m, 3H), 7.24-7.31 (m, 2H), 7.21 (dd, J=6.26, 7.83 Hz, 1H), 7.12 (d, J=7.83 Hz, 1H), 7.06 (d, J=9.78 Hz, 1H), 6.91 (dt, J=1.76, 8.51 Hz, 1H), 4.40 (s, 2H), 4.33 (q, J=7.43 Hz, 2H), 1.61 (t, J=7.43 Hz, 3H) $^{13}$C NMR (101 MHz, CDCl$_3$) δ 162.7, 159.9, 158.7, 158.1, 138.5, 135.6, 130.0, 130.0, 129.9, 129.6, 127.8, 125.0, 116.3, 114.5, 104.6, 48.6, 37.0, 15.4

Sub-Example 15: CCG: 257903

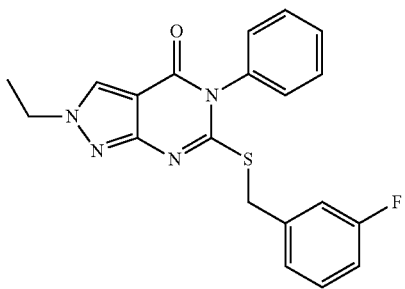 [SMILES: CCn1cc2c(=O)n(-c3ccccc3)c(SCc3cccc(F)c3)nc2n1]

2-ethyl-6-((3-fluorobenzyl)thio)-5-phenyl-2H-pyrazolo[3,4-d]pyrimidin-4(5H)-one

White Solid (8 mg, 0.021 mmol, 9.26% yield) M+H found: MS (ESI): m/z 381.1178 [M+H]$^+$ $^1$H NMR (500 MHz, CDCl$_3$) δ 8.04 (s, 1H), 7.49-7.57 (m, 3H), 7.23-7.32 (m, 3H), 7.14 (d, J=7.83 Hz, 1H), 7.10 (d, J=9.78 Hz, 1H), 6.95 (dt, J=2.20, 8.44 Hz, 1H), 4.41 (q, J=7.01 Hz, 2H), 4.33 (s, 2H), 1.53 (t, J=7.09 Hz, 3H) $^{13}$C NMR (126 MHz, CDCl$_3$) δ 162.7, 161.1, 157.7, 150.2, 138.7, 135.6, 135.4, 130.1, 130.1, 129.8, 129.4, 124.7, 116.1, 114.6, 103.0, 42.5, 36.8, 15.0

Sub-Example 16: CCG: 257905

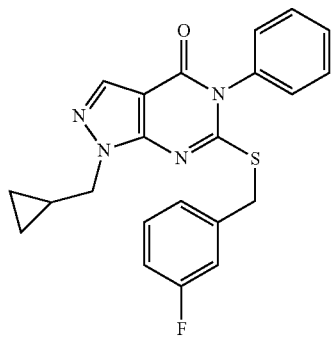 [SMILES: O=c1c2cnn(CC3CC3)c2nc(SCc2cccc(F)c2)n1-c1ccccc1]

1-(cyclopropylmethyl)-6-((3-fluorobenzyl)thio)-5-phenyl-1H-pyrazolo[3,4-d]pyrimidin-4(5H)-one White Solid (44 mg, 0.108 mmol, 47.7% yield) MS (ESI): m/z 407.1335 [M+H]$^+$ $^1$H NMR (400 MHz, CDCl$_3$) δ 8.05 (s, 1H), 7.48-7.57 (m, 3H), 7.20-7.33 (m, 3H), 7.12 (d, J=7.83 Hz, 1H), 7.08 (d, J=9.39 Hz, 1H), 6.95 (t, J=8.41 Hz, 1H), 4.31 (s, 2H), 4.19 (d, J=7.04 Hz, 2H), 1.38 (s, 1H), 0.54-0.69 (m, 2H), 0.36-0.50 (m, 2H) $^{13}$C NMR (101 MHz, CDCl$_3$) δ 162.7, 161.1, 157.8, 150.4, 138.5, 135.6, 135.4, 130.1, 130.1, 129.8, 129.4, 124.6, 116.0, 114.6, 103.0, 52.1, 36.9, 11.3, 4.0

Sub-Example 17: CCG: 257906

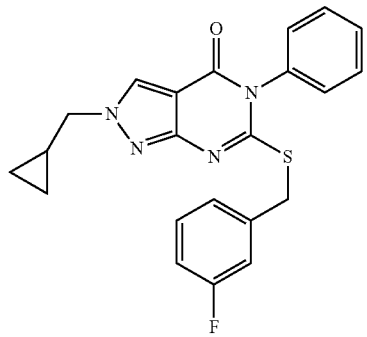 [SMILES: O=c1c2cn(CC3CC3)nc2nc(SCc2cccc(F)c2)n1-c1ccccc1]

2-(cyclopropylmethyl)-6-((3-fluorobenzyl)thio)-5-phenyl-2H-pyrazolo[3,4-d]pyrimidin-4(5H)-one White Solid (34 mg, 0.084 mmol, 36.8% yield) MS (ESI): m/z 407.1334 [M+H]$^+$ $^1$H NMR (400 MHz, CDCl$_3$) δ 8.19 (s, 1H), 7.42-7.58 (m, 3H), 7.27 (d, J=4.30 Hz, 2H), 7.16-7.24 (m, 1H), 7.11 (d, J=7.43 Hz, 1H), 7.06 (d, J=9.78 Hz, 1H), 6.90 (t, J=8.41 Hz, 1H), 4.39 (s, 2H), 4.12 (d, J=7.04 Hz, 2H), 1.34-1.49 (m, 1H), 0.72 (d, J=7.83 Hz, 2H), 0.44 (d, J=4.30 Hz, 2H) $^{13}$C NMR (101 MHz, CDCl$_3$) δ 162.7, 159.8, 158.8, 158.0, 138.5, 135.6, 130.0, 129.9, 129.6, 129.6, 127.9, 125.0, 116.2, 114.4, 104.7, 58.3, 37.0, 10.5, 4.3

Sub-Example 18: CCG: 258082

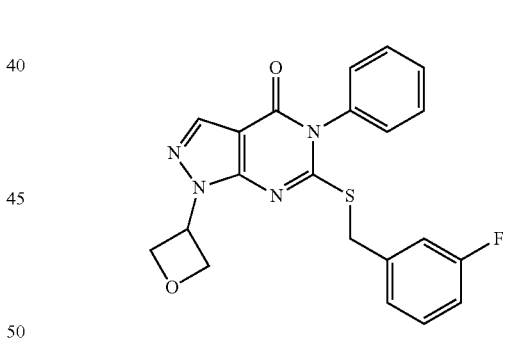

6-((3-fluorobenzyl)thio)-1-(oxetan-3-yl)-5-phenyl-H-pyrazolo[3,4-d]pyrimidin-4(5H)-one White solid (18 mg, 0.044 mmol, 15.53% yield) MS (ESI): m/z 409.1[M+H]$^+$ $^1$H NMR (500 MHz, CDCl$_3$) δ 8.13 (s, 1H), 7.50-7.57 (m, 3H), 7.21-7.31 (m, 3H), 7.12 (d, J=7.83 Hz, 1H), 7.08 (d, J=9.29 Hz, 1H), 6.92-6.99 (m, 1H), 5.94 (quin, J=7.21 Hz, 1H), 5.30 (t, J=6.36 Hz, 2H), 5.06 (t, J=7.09 Hz, 2H), 4.33 (s, 2H) $^{13}$C NMR (126 MHz, CDCl$_3$) δ 162.7, 162.0, 157.5, 150.9, 138.1, 136.3, 135.3, 130.2, 130.1, 129.8, 129.2, 124.6, 116.0, 114.7, 103.5, 76.8, 50.8, 36.9

Sub-Example 19: CCG: 258083

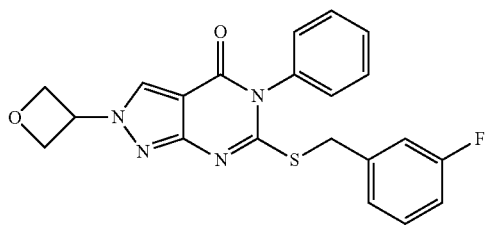 [SMILES: O=c1c2cn(C3COC3)nc2nc(SCc2cccc(F)c2)n1-c1ccccc1]

6-((3-fluorobenzyl)thio)-2-(oxetan-3-yl)-5-phenyl-2H-pyrazolo[3,4-d]pyrimidin-4(5H)-one White solid (25 mg, 0.061 mmol, 21.57% yield) MS (ESI): m/z 409.1 [M+H]+ $^1$H NMR (500 MHz, CDCl$_3$) δ 8.20 (s, 1H), 7.46-7.54 (m, 3H), 7.26-7.31 (m, 2H), 7.19-7.25 (m, 1H), 7.12 (d, J=7.34 Hz, 1H), 7.06 (d, J=9.78 Hz, 1H), 6.92 (dt, J=1.71, 8.44 Hz, 1H), 5.56 (quin, J=6.97 Hz, 1H), 5.21 (t, J=6.60 Hz, 2H), 5.07 (t, J=7.34 Hz, 2H), 4.42 (s, 2H) $^{13}$C NMR (126 MHz, CDCl$_3$) δ 162.6, 160.8, 158.4, 158.3, 138.1, 135.3, 130.0, 129.9, 129.6, 129.5, 128.1, 125.0, 116.2, 114.5, 105.2, 76.7, 56.7, 37.1

Sub-Example 20: CCG: 258084

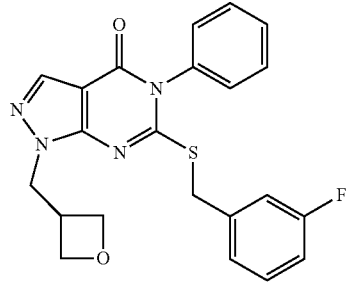 [SMILES: O=c1c2cnn(CC3COC3)c2nc(SCc2cccc(F)c2)n1-c1ccccc1]

6-((3-fluorobenzyl)thio)-1-(oxetan-3-ylmethyl)-5-phenyl-1H-pyrazolo[3,4-d]pyrimidin-4(5H)-one White solid (39 mg, 0.092 mmol, 32.5% yield) MS (ESI): m/z 423.1 [M+H]+. $^1$H NMR (500 MHz, cdcl$_3$) δ 8.00 (s, 1H), 7.48-7.56 (m, 3H), 7.23-7.31 (m, 3H), 7.14 (d, J=7.83 Hz, 1H), 7.08 (d, J=9.78 Hz, 1H), 6.92-6.98 (m, 1H), 4.83 (t, J=7.09 Hz, 2H), 4.62 (d, J=7.34 Hz, 2H), 4.60 (t, J=6.10 Hz, 2H), 4.32 (s, 2H), 3.48-3.59 (m, 1H) $^{13}$C NMR (126 MHz, cdcl$_3$) δ 162.6, 161.7, 157.4, 150.8, 138.2, 135.7, 135.3, 130.0, 130.0, 129.7, 129.2, 124.5, 115.8, 114.5, 102.8, 74.7, 49.3, 36.8, 35.1

Sub-Example 21: CCG: 258085

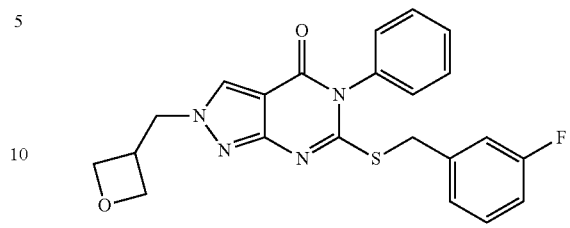

6-((3-fluorobenzyl)thio)-2-(oxetan-3-ylmethyl)-5-phenyl-2H-pyrazolo[3,4-d]pyrimidin-4(5H)-one White solid (27 mg, 0.064 mmol, 22.52% yield) MS (ESI): m/z 423.1 [M+H]+ $^1$H NMR (500 MHz, cdcl$_3$) δ 8.07 (s, 1H), 7.47-7.54 (m, 3H), 7.25-7.30 (m, 2H), 7.19-7.25 (m, 1H), 7.11 (d, J=7.34 Hz, 1H), 7.05 (d, J=9.29 Hz, 1H), 6.92 (dt, J=1.47, 8.31 Hz, 1H), 4.86 (t, J=7.09 Hz, 2H), 4.57 (d, J=7.34 Hz, 2H), 4.54 (t, J=6.11 Hz, 2H), 4.38 (s, 2H), 3.58-3.70 (m, 1H) $^{13}$C NMR (126 MHz, cdcl$_3$) δ 162.6, 160.3, 158.5, 158.4, 138.3, 135.4, 130.0, 129.9, 129.6, 129.5, 128.7, 125.0, 116.2, 114.4, 104.9, 74.4, 55.8, 37.0, 35.3

Preparation 3

Oxetan-3-ylmethyl methanesulfonate

TEA (0.633 mL, 4.54 mmol) was added to a solution of oxetan-3-ylmethanol (0.183 mL, 2.270 mmol) in 2.5 mL DCM in an ice cooled flask followed by Mesyl-Cl (0.212 mL, 2.72 mmol). After stirring for 24 hours at RT, the mixture was diluted with dichloromethane and washed with saturated sodium bicarbonate solution. The organic portion was dried with sodium sulfate and concentrated under reduced pressure to give the titled compound as pale yellow oil (340 mg, 2.046 mmol, 90% yield). $^1$H NMR (400 MHz, CDCl$_3$) δ 4.82 (t, J=7.40 Hz, 2H), 4.47 (t, J=6.30 Hz, 2H), 4.45 (d, J=7.04 Hz, 2H), 3.38 (m, 1H), 3.05 (s, 3H)

Preparation 4

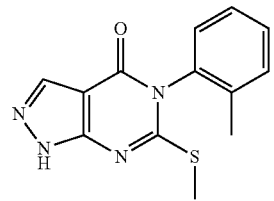 [SMILES: CSc1nc2[nH]ncc2c(=O)n1-c1ccccc1C]

6-(methylthio)-5-(o-tolyl)-1H-pyrazolo[3,4-d]pyrimidin-4(5H)-one 6-thioxo-5-(o-tolyl)-6,7-dihydro-1H-pyrazolo[3,4-d]pyrimidin-4(5H)-one (500 mg, 1.936 mmol), potassium carbonate (401 mg, 2.90 mmol), and 5 mL ACN were added to a flask followed by MeI (0.121 mL, 1.936 mmol). The flask was flushed with nitrogen and stirred at RT overnight. The next day the reaction was diluted with water and extracted with ethyl acetate. The organic portion was washed with brine, dried over sodium sulfate and the solvent was removed, yielding the titled compound as a white solid (370 mg, 1.359 mmol, 70.2% yield) which was taken forward without further purification.

Preparation 5

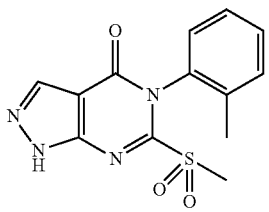 [SMILES: Cc1ccccc1-n1c(S(C)(=O)=O)nc2[nH]ncc2c1=O]

6-(methylsulfonyl)-5-(o-tolyl)-1H-pyrazolo[3,4-d]pyrimidin-4(5H)-one

A flask was charged with 70 wt. % mCPBA (1005 mg, 4.08 mmol) and 10 mL DCM. 6-(methylthio)-5-(o-tolyl)-1H-pyrazolo[3,4-d]pyrimidin-4(5H)-one (370 mg, 1.359 mmol) suspended in 5 mL DCM was added to the flask and the mixture was stirred overnight. The reaction was quenched with 10 mL 5% aq. sodium bisulfite solution and stirred for 30 min then diluted with 50 mL DCM. The organic portion was washed with brine, dried over sodium sulfate and the solvent was removed yielding a white solid which was purified by flash (50-75% EtOAc in Hex) yielding titled compound as a yellow oil (200 mg, 0.657 mmol, 48.4% yield). $^1$H NMR (400 MHz, CDCl$_3$) δ 8.28 (s, 1H), 7.38-7.44 (m, 1H), 7.28-7.37 (m, 3H), 3.37 (s, 3H), 2.16 (s, 3H)

Sub-Example 22: CCG: 257129

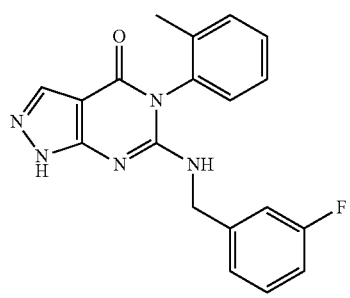 [SMILES: Cc1ccccc1-n1c(NCc2cccc(F)c2)nc2[nH]ncc2c1=O]

6-((3-fluorobenzyl)amino)-5-(o-tolyl)-1H-pyrazolo[3,4-d]pyrimidin-4(5H)-one

To a vial charged with DMAP (4.22 mg, 0.035 mmol), 6-(methylsulfonyl)-5-(o-tolyl)-1H-pyrazolo[3,4-d]pyrimidin-4(5H)-one (105 mg, 0.345 mmol), and 0.5 mL THF was added (3-fluorophenyl)methanamine (0.079 mL, 0.690 mmol) and DIPEA (0.060 mL, 0.345 mmol). The tube was flushed with argon, sealed, and heated to 70° C. for 1 Hr. The mixture was diluted with sat. aq. NH$_4$Cl and extracted with ethyl acetate. The organic portion was dried over sodium sulfate and the solvent was removed. The crude residue was purified twice by flash (50-80% EtOAc in Hex.) yielding titled compound (20 mg, 0.057 mmol, 16.59% yield) as a yellow oil. MS (ESI): m/z 350.0 [M+H]$^+$ $^1$H NMR (500 MHz, CDCl$_3$) δ 8.05 (s, 1H), 7.37-7.47 (m, 3H), 7.23 (t, J=8.00 Hz, 2H), 6.92 (d, J=8.80 Hz, 1H), 6.94 (d, J=6.85 Hz, 1H), 6.87 (d, J=9.78 Hz, 1H), 4.64 (t, J=5.10 Hz, 1H), 4.58 (m, 2H), 2.15 (s, 3H) $^{13}$C NMR (126 MHz, CDCl$_3$) δ 163.9, 161.9, 157.7, 154.3, 152.8, 140.2, 137.1, 133.2, 132.3, 130.5, 130.4, 129.0, 128.4, 122.6, 114.5, 114.2, 100.2, 45.2, 17.3

Preparation 6

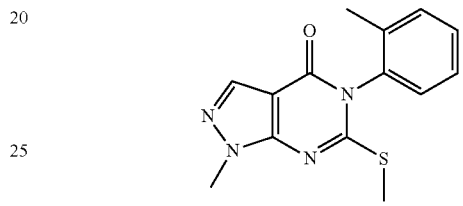

1-methyl-6-(methylthio)-5-(o-tolyl)-1H-pyrazolo[3,4-d]pyrimidin-4(5H)-one

A flask under nitrogen charged with 60% NaH (1.182 g, 29.6 mmol) in mineral oil was cooled to 0° C. and 15 mL DMF was added by syringe. 5-amino-1-methyl-1H-pyrazole-4-carboxylate (5 g, 29.6 mmol) was dissolved in another 15 mL DMF and added to the flask by syringe over the course of 10 minutes. The reaction was stirred for another 10 minutes at which point the evolution of hydrogen had subsided. O-toluyl isothiocyanate (3.96 mL, 29.6 mmol) was added by syringe over the course of a minute and the reaction was stirred for 10 minutes then allowed to warm to RT. After stirring overnight MeI (2.218 mL, 35.5 mmol) was added and the mixture was stirred for 4 hours. The product was precipitated by addition of water and collected by vacuum filtration yielding the titled compound as a white solid (6.3 g, 22.00 mmol, 74.4% yield). $^1$H NMR (400 MHz, CDCl$_3$) δ 8.04 (s, 1H), 7.45 (dt, J=1.40, 7.40 Hz, 1H), 7.38 (d, J=7.40 Hz, 1H), 7.36 (dt, J=1.40, 7.40 Hz, 1H), 7.16 (d, J=7.83 Hz, 1H), 4.01 (s, 3H), 2.51 (s, 3H), 2.13 (s, 3H)

Preparation 7

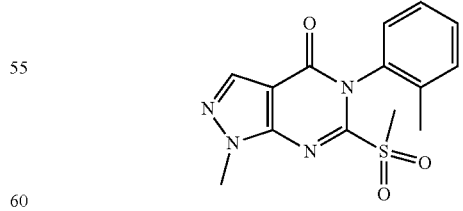

1-methyl-6-(methylsulfonyl)-5-(o-tolyl)-1H-pyrazolo[3,4-d]pyrimidin-4(5H)-one

A solution of 70 wt. % mCPBA (16.27 g, 66.0 mmol) and 1-methyl-6-(methylthio)-5-(o-tolyl)-1H-pyrazolo[3,4-d]pyrimidin-4(5H)-one (6.3 g, 22.00 mmol) in 100 mL DCM was stirred overnight at room temperature. 50 mL sat. aq. Sodium Thiosulfate was added and the mixture was stirred vigorously for 1 hour. The reaction was diluted with ethyl acetate and the organic portion washed 2× with water and 1× with brine before drying over sodium sulfate. The solvent was removed and the crude solid was taken up in DCM and the insoluble chlorobenzoic acid was filtered off. The filtrate was concentrated and taken up in minimal hot ethanol and slowly cooled to 0° C. at which point the titled compound crystallized out as a tan solid (5.1 g, 16.02 mmol, 72.8% yield). $^1$H NMR (400 MHz, CDCl$_3$) δ 8.19 (s, 1H), 7.46 (t, J=7.40 Hz, 1H), 7.32-7.40 (m, 2H), 7.26-7.29 (m, 1H), 4.09 (s, 3H), 3.44 (s, 3H), 2.15 (s, 3H)

Sub-Example 23: CCG: 257430

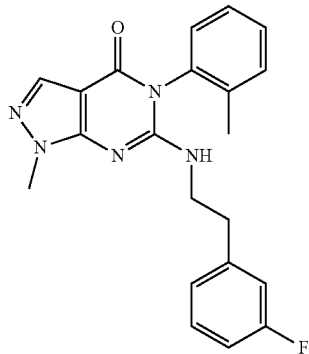 [SMILES: Cc1ccccc1-n1c(NCCc2cccc(F)c2)nc2c(cnn2C)c1=O]

6-((3-fluorophenethyl)amino)-1-methyl-5-(o-tolyl)-1H-pyrazolo[3,4-d]pyrimidin-4(5H)-one To a flask charged with 1-methyl-6-(methylsulfonyl)-5-(o-tolyl)-1H-pyrazolo[3,4-d]pyrimidin-4(5H)-one (100 mg, 0.314 mmol) under nitrogen, was added 0.5 mL DMF, pyridine (0.051 mL, 0.628 mmol) and 2-(3-fluorophenyl)ethanamine (0.041 mL, 0.314 mmol) sequentially by syringe. The mixture was stirred for 24 hours at which point the reaction was diluted with ethyl acetate and washed with sat. aq. NH$_4$Cl and brine. The organic portion was dried over sodium sulfate and the solvent removed. The crude product was purified by flash, (0-100% EtOAc in Hexanes) yielding the titled compound as a white solid (35 mg, 0.093 mmol, 29.5% yield). MS (ESI): m/z 378.1 [M+H]$^+$ $^1$H NMR (400 MHz, CDCl$_3$) δ 7.92 (s, 1H), 7.39 (dt, J=1.00, 7.40 Hz, 1H), 7.35 (d, J=6.26 Hz, 1H), 7.31 (dt, J=1.50, 7.70 Hz, 1H), 7.16-7.23 (m, 1H), 7.03 (d, J=7.43 Hz, 1H), 6.90 (dt, J=2.35, 8.61 Hz, 1H), 6.80 (d, J=7.43 Hz, 1H), 6.72 (d, J=9.39 Hz, 1H), 3.91 (s, 3H), 3.56-3.70 (m, 2H), 2.83 (t, J=6.65 Hz, 2H), 1.99 (s, 3H) $^{13}$C NMR (101 MHz, CDCl$_3$) δ 162.8, 157.7, 152.9, 152.1, 140.9, 137.0, 135.5, 133.3, 132.0, 130.2, 130.2, 128.1, 124.2, 115.5, 113.5, 100.0, 42.7, 34.7, 33.5, 17.1

Sub-Example 24: CCG: 257435

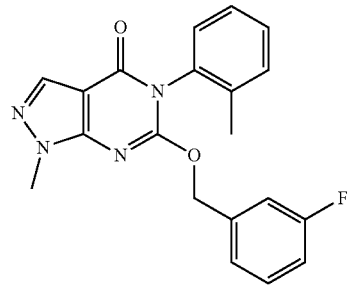 [SMILES: Cc1ccccc1-n1c(OCc2cccc(F)c2)nc2c(cnn2C)c1=O]

6-((3-fluorobenzyl)oxy)-1-methyl-5-(o-tolyl)-1H-pyrazolo[3,4-d]pyrimidin-4(5H)-one To a dry flask at 0° C. under N2 charged with 60 wt. % Sodium Hydride in mineral oil (15.08 mg, 0.377 mmol) was added 1 mL of DMF and (3-fluorophenyl)methanol (0.038 mL, 0.353 mmol) by syringe. The mixture was stirred for 10 minutes at which point solid 1-methyl-6-(methylsulfonyl)-5-(o-tolyl)-1H-pyrazolo[3,4-d]pyrimidin-4(5H)-one (75 mg, 0.236 mmol) was added quickly. The mixture was stirred overnight and gradually warmed to RT. The following day the mixture was diluted with EtOAc and washed with water. The water was back extracted with a small portion of EtOAc and the combined organics were washed 3× with brine before drying over sodium sulfate and concentrating. The crude was purified by flash (0-100% EtOAc in Hex) yielding the titled compound as a white solid (30 mg, 0.082 mmol, 34.9% yield). MS (ESI): m/z 365.1 [M+H]$^+$ $^1$H NMR (400 MHz, CDCl$_3$) δ 8.01 (s, 1H), 7.30-7.45 (m, 3H), 7.21-7.30 (m, 1H), 7.12 (d, J=7.43 Hz, 1H), 6.91-7.01 (m, 2H), 6.82 (d, J=9.39 Hz, 1H), 5.33-5.49 (m, 2H), 3.95 (s, 3H), 2.06 (s, 3H) $^{13}$C NMR (101 MHz, CDCl$_3$) δ 162.7, 157.5, 155.2, 151.0, 137.6, 135.7, 135.7, 134.1, 131.0, 130.1, 129.3, 128.3, 127.1, 122.7, 115.2, 114.2, 102.1, 69.2, 34.0, 17.4

Preparation 8

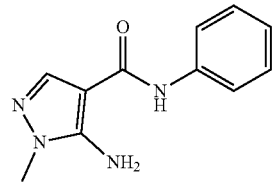 [SMILES: Cn1ncc(C(=O)Nc2ccccc2)c1N]

5-amino-1-methyl-N-phenyl-1H-pyrazole-4-carboxamide

A dry flask with gas inlet under nitrogen was charged with 25 mL THF and aniline (1.349 mL, 14.78 mmol). The flask was cooled to −78° C. and nBuLi in hexanes (2.1M, 5.67 mL, 14.19 mmol) was added slowly. After stirring for 30 min, solid ethyl 5-amino-1-methyl-1H-pyrazole-4-carboxylate (2 g, 11.82 mmol) was added against a strong counter-flow of nitrogen. The flask was allowed to warm to RT and stirred overnight. The next morning the flask was again cooled to −78° C. and another portion of nBuLi (2.1M, 5.67 mL, 14.19 mmol) was added and then the flask was warmed to RT. After 3 hours the reaction was quenched with sat. aq. ammonium chloride and the volatiles were removed. The residue was taken up in EtOAc and washed with water and brine before drying the organic portion over sodium sulfate and concentrating. The crude obtained was recrystallized from ethanol, yielding the titled compound as an orange crystalline solid (1.6 g, 7.40 mmol, 62.6% yield). $^1$H NMR (400 MHz, DMSO-$d_6$) δ 9.38 (s, 1H), 7.89 (s, 1H), 7.68 (d, J=7.83 Hz, 2H), 7.29 (t, J=8.02 Hz, 2H), 6.93-7.11 (m, 1H), 6.31 (s, 2H), 3.54 (s, 3H)

Preparation 9

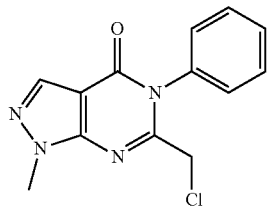 [SMILES: Cn1ncc2c(=O)n(-c3ccccc3)c(CCl)nc21]

6-(chloromethyl)-1-methyl-5-phenyl-1H-pyrazolo[3,4-d]pyrimidin-4(5H)-one

A flask under nitrogen charged with chloroacetic acid (12.76 g, 135 mmol) and 5-amino-1-methyl-N-phenyl-1H-pyrazole-4-carboxamide (1.46 g, 6.75 mmol) was heated at 80° C. until a homogenous melt was obtained. Chloroacetyl chloride (1.352 mL, 16.88 mmol) was added dropwise and the mixture was stirred at 80° C. for 1 hour. The flask was then fitted with a reflux condenser and heated to 120° C. overnight. The next day the flask was removed from the oil bath and immediately poured into 100 mL water. The mixture was stirred vigorously until cool to the touch then filtered yielding the titled compound as an off white solid (1.22 g, 4.44 mmol, 65.8% yield). $^1$H NMR (400 MHz, CDCl$_3$) δ 8.10 (s, 1H), 7.48-7.64 (m, 3H), 7.28-7.37 (m, 2H), 4.23 (s, 2H), 4.05 (s, 3H)

Sub-Example 25: CCG: 258079

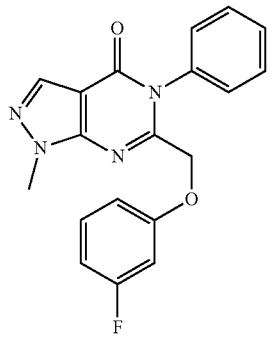 [SMILES: Cn1ncc2c(=O)n(-c3ccccc3)c(COc3cccc(F)c3)nc21]

6-((3-fluorophenoxy)methyl)-1-methyl-5-phenyl-1H-pyrazolo[3,4-d]pyrimidin-4(5H)-one To a dry vial charged with potassium carbonate (55.3 mg, 0.400 mmol) and 6-(chloromethyl)-1-methyl-5-phenyl-1H-pyrazolo[3,4-d]pyrimidin-4(5H)-one (55 mg, 0.200 mmol) was added 1 mL DMF followed by 3-fluorophenol (0.027 mL, 0.300 mmol). The vial was flushed with argon, sealed, and heated to 70° C. for 3 hours at which point the reaction was complete by HPLC. The mixture was diluted with 20 mL water and extracted 2× with ethyl acetate. The combined organics were washed 3× with brine and dried over sodium sulfate. Removal of solvent yielded a colorless oil which was subjected to flash (eluted at 40% EA/Hex) yielding the titled compound as a white crystalline solid (58 mg, 0.166 mmol, 83% yield). MS (ESI): m/z 351.1 [M+H]$^+$ $^1$H NMR (400 MHz, CDCl$_3$) δ 8.10 (s, 1H), 7.43-7.55 (m, 3H), 7.28 (d, J=7.04 Hz, 2H), 7.12-7.21 (m, 1H), 6.66 (dt, J=1.57, 8.22 Hz, 1H), 6.52-6.58 (m, 1H), 6.46-6.52 (m, 1H), 4.71 (s, 2H), 4.02 (s, 3H) $^{13}$C NMR (101 MHz, CDCl$_3$) δ 163.3, 158.7, 158.0, 153.9, 150.5, 135.6, 135.4, 130.3, 129.8, 129.7, 128.5, 110.3, 108.7, 104.7, 102.6, 68.3, 34.3

Sub-Example 26: CCG: 258080

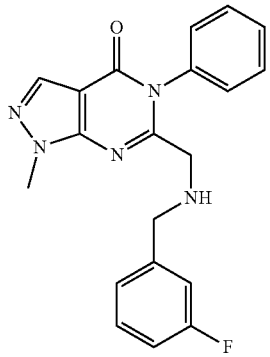 [SMILES: Cn1ncc2c(=O)n(-c3ccccc3)c(CNCc3cccc(F)c3)nc21]

6-(((3-fluorobenzyl)amino)methyl)-1-methyl-5-phenyl-1H-pyrazolo[3,4-d]pyrimidin-4(5H)-one To a dry vial charged with potassium carbonate (83 mg, 0.601 mmol) and 6-(chloromethyl)-1-methyl-5-phenyl-1H-pyrazolo[3,4-d]pyrimidin-4(5H)-one (55 mg, 0.200 mmol) was added 1 mL DMF followed by (3-fluorophenyl)methanamine (0.092 mL, 0.801 mmol). The vial was flushed with argon, sealed and heated to 40° C. overnight at which point the reaction was complete by HPLC. The mixture was diluted with 20 mL water and extracted 2× with ethyl acetate. The combined organics were washed 3× with brine and dried over sodium sulfate. The solvent was removed and the crude was purified by Prep TLC (20% Acetone in Chloroform) followed by recrystallization from ethanol yielding the titled compound as a white crystalline solid (15 mg, 0.041 mmol, 20.62% yield). MS (ESI): m/z 364.2 [M+H]$^+$ $^1$H NMR (500 MHz, CDCl$_3$) δ 8.07 (s, 1H), 7.46-7.57 (m, 3H), 7.22-7.29 (m, 1H), 7.18 (d, J=6.85 Hz, 2H), 6.97-7.06 (m, 2H), 6.94 (t, J=8.31 Hz, 1H), 4.04 (s, 3H), 3.76 (s, 2H), 3.44 (s, 2H), 2.36 (br. s., 1H) $^{13}$C NMR (126 MHz, CDCl$_3$) δ 163.0, 158.2, 158.2, 150.8, 142.1, 135.9, 135.3, 130.0, 129.9, 129.6, 128.3, 123.6, 114.9, 114.1, 104.2, 52.7, 51.5, 34.2

Preparation 10

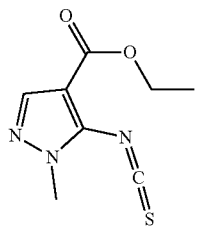

ethyl 5-isothiocyanato-1-methyl-1H-pyrazole-4-carboxylate

To a dry flask under nitrogen at 0° C. charged with 60 wt. % NaH (296 mg, 7.39 mmol) and ethyl 5-amino-1-methyl-1H-pyrazole-4-carboxylate (500 mg, 2.96 mmol) was added 10 mL THF. The mixture was stirred for 10 minutes at which point $CS_2$ (1.782 mL, 29.6 mmol) was added by syringe. The mixture was allowed warm to room temperature then heated to 40° C. and stirred for 3H. After cooling the flask to 0° C. and iodine was added portion wise over 10 minutes. The mixture was stirred for another hour at 0° C. then 30 mL diethyl ether was added and the precipitate was filtered off. The filtrate was washed 3× with 1N HCl, 1× with brine and the organic portion was dried over sodium sulfate and the solvent removed yielding a reddish black solid. The crude product was purified by flash (0-30% EA in Hex) yielding the titled compound as a yellow solid (460 mg, 2.178 mmol, 73.7% yield). M+H found 212.0 $^1$H NMR (400 MHz, CDCl$_3$) δ 7.81 (s, 1H), 4.25-4.44 (m, 2H), 3.80 (s, 3H), 1.30-1.44 (m, 3H)

General Procedure B

To a dry flask under nitrogen charged with ethyl 5-isothiocyanato-1-methyl-1H-pyrazole-4-carboxylate (50 mg, 0.237 mmol) and 2 mL dry DMF was added aniline (0.022 mL, 0.237 mmol) by syringe. The reaction was stirred at RT for 1 hr and then cooled to 0° C. 60 wt. % NaH (9.47 mg, 0.237 mmol) was added and the flask was stirred at 0 C for 20 min then allowed to warm to RT and stirred for 3H. The flask was once again cooled to 0 C and 3-fluorobenzyl bromide (0.029 mL, 0.237 mmol) was added by syringe. The mixture was stirred at 0 C for 30 min at which point the reaction was complete by HPLC. The reaction was diluted with 10 mL water and extracted 2× with 10 mL EtOAc. The combined organic portion was washed 3× with brine, dried over sodium sulfate and the solvent removed. The crude product was purified by flash (0-100% EtOAc in Hexanes) yielding the titled compound. This procedure was used for Sub-Examples 27-32

Sub-Example 27: CCG: 257723

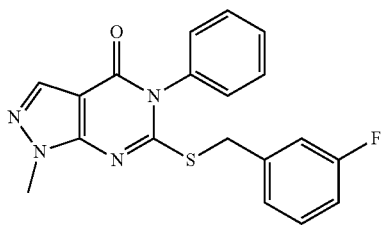 [SMILES: Cn1ncc2c(=O)n(-c3ccccc3)c(SCc3cccc(F)c3)nc21]

6-((3-fluorobenzyl)thio)-1-methyl-5-phenyl-1H-pyrazolo[3,4-d]pyrimidin-4(5H)-one Yellow solid (73 mg, 0.199 mmol, 84% yield). MS (ESI): m/z 367.03 [M+H]$^+$. $^1$H NMR (500 MHz, CDCl$_3$) δ 8.03 (s, 1H), 7.47-7.58 (m, 3H), 7.22-7.30 (m, 3H), 7.13 (d, J=7.83 Hz, 1H), 7.09 (d, J=9.78 Hz, 1H), 6.95 (dt, J=2.20, 8.44 Hz, 1H), 4.34 (s, 2H), 4.01 (s, 3H) $^{13}$C NMR (126 MHz, CDCl$_3$) δ 162.7, 161.3, 157.7, 150.9, 138.5, 135.5, 135.4, 130.1, 130.1, 129.8, 129.4, 124.8, 116.2, 114.6, 103.0, 36.9, 34.1

Sub-Example 28: CCG: 257727

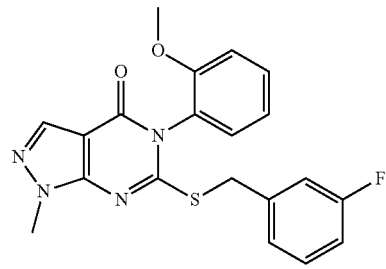 [SMILES: COc1ccccc1-n1c(SCc2cccc(F)c2)nc2c(cnn2C)c1=O]

6-((3-fluorobenzyl)thio)-5-(2-methoxyphenyl)-1-methyl-1H-pyrazolo[3,4-d]pyrimidin-4(5H)-one White crystalline solid (18 mg, 0.045 mmol, 19.18% yield) MS (ESI): m/z 397.0 [M+H]$^+$ (400 MHz, CDCl$_3$) δ 8.02 (s, 1H), 7.49 (t, J=8.02 Hz, 1H), 7.22-7.29 (m, 1H), 7.19 (d, J=7.83 Hz, 1H), 7.02-7.16 (m, 4H), 6.94 (t, J=8.22 Hz, 1H), 4.33 (s, 2H), 3.99 (s, 3H), 3.78 (s, 3H) $^{13}$C NMR (101 MHz, CDCl$_3$) δ 162.7, 161.8, 157.4, 155.4, 151.1, 138.8, 135.4, 131.9, 130.7, 130.0, 124.7, 123.9, 121.1, 116.0, 114.5, 112.4, 103.0, 55.9, 36.5, 34.1

Sub-Example 29: CCG: 258077

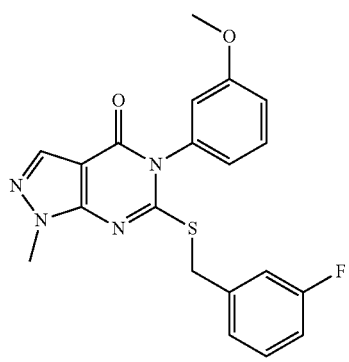 [SMILES: COc1cccc(-n2c(SCc3cccc(F)c3)nc3c(cnn3C)c2=O)c1]

6-((3-fluorobenzyl)thio)-5-(3-methoxyphenyl)-1-methyl-1H-pyrazolo[3-d]pyrimidin-4(5H)-one White Solid (75 mg, 0.189 mmol, 80% yield). MS (ESI): m/z 397.1 [M+H]$^+$ $^1$H NMR (400 MHz, CDCl$_3$) δ 7.99 (s, 1H), 7.41 (t, J=8.22 Hz, 1H), 7.21-7.30 (m, 1H), 7.07-7.17 (m, 2H), 7.04 (dd, J=2.35, 8.22 Hz, 1H), 6.90-6.98 (m, 1H), 6.85 (dd, J=0.78, 7.83 Hz, 1H), 6.80 (d, J=1.96 Hz, 1H), 4.33

(s, 2H), 3.99 (s, 3H), 3.80 (s, 3H) ¹³C NMR (101 MHz, CDCl₃) δ 162.7, 161.3, 160.5, 157.6, 150.9, 138.5, 136.5, 135.4, 130.4, 130.1, 124.8, 121.4, 116.2, 115.9, 114.9, 114.6, 102.9, 55.5, 36.9, 34.1

Sub-Example 30: CCG: 258078

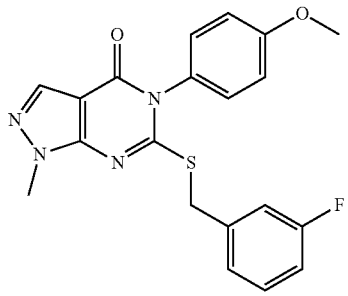 [SMILES: COc1ccc(-n2c(SCc3cccc(F)c3)nc3c(cnn3C)c2=O)cc1]

6-((3-fluorobenzyl)thio)-5-(4-methoxyphenyl)-1-methyl-1H-pyrazolo[3,4-d]pyrimidin-4(5H)-one White needles (44 mg, 0.111 mmol, 46.9% yield). MS (ESI): m/z 397.1 [M+H]⁺ ¹H NMR (400 MHz, CDCl₃) δ 8.01 (s, 1H), 7.22-7.30 (m, 1H), 7.07-7.19 (m, 4H), 6.98-7.04 (m, 2H), 6.95 (dt, J=2.35, 8.41 Hz, 1H), 4.32 (s, 2H), 4.00 (s, 3H), 3.85 (s, 3H) ¹³C NMR (101 MHz, cdcl₃) δ 162.7, 162.0, 160.7, 158.0, 150.9, 138.6, 135.4, 130.4, 130.0, 127.8, 124.8, 116.2, 115.0, 114.6, 102.9, 55.5, 37.0, 34.1

Sub-Example 31: CCG: 257907

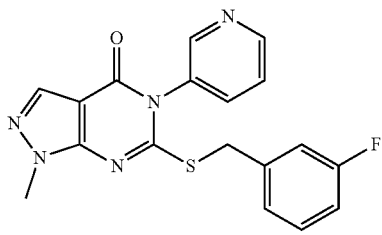 [SMILES: Cn1ncc2c(=O)n(-c3cccnc3)c(SCc3cccc(F)c3)nc21]

6-((3-fluorobenzyl)thio)-1-methyl-5-(pyridin-3-yl)-1H-pyrazolo[3,4-d]pyrimidin-4(5H)-one White solid (56 mg, 0.152 mmol, 64.4% yield) MS (ESI): m/z 368.0972 [M+H]+(500 MHz, CDCl₃) δ 8.72 (d, J=4.40 Hz, 1H), 8.52 (s, 1H), 7.97 (s, 1H), 7.63 (d, J=8.31 Hz, 1H), 7.45 (dd, J=4.89, 7.83 Hz, 1H), 7.21-7.30 (m, 1H), 7.12 (d, J=7.34 Hz, 1H), 7.07 (d, J=9.78 Hz, 1H), 6.94 (t, J=8.30 Hz, 1H), 4.37 (d, J=14.18 Hz, 1H), 4.33 (d, J=14.18 Hz, 1H), 4.00 (s, 3H) ¹³C NMR (126 MHz, CDCl₃) δ 162.7, 160.8, 157.4, 151.0, 150.8, 150.2, 138.1, 137.3, 135.4, 132.4, 130.2, 124.8, 124.2, 116.1, 114.8, 102.7, 36.9, 34.2

Sub-Example 32: CCG: 257908

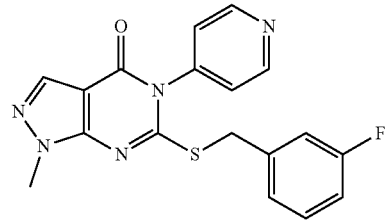 [SMILES: Cn1ncc2c(=O)n(-c3ccncc3)c(SCc3cccc(F)c3)nc21]

6-((3-fluorobenzyl)thio)-1-methyl-5-(pyridin-4-yl)-1H-pyrazolo[3,4-d]pyrimidin-4(5H)-one Off white solid (54 mg, 0.147 mmol, 62.1% yield) MS (ESI): m/z 368.0974 [M+H]⁺ ¹H NMR (500 MHz, CDCl₃) δ 8.82 (d, J=4.89 Hz, 2H), 8.00 (s, 1H), 7.26-7.32 (m, 1H), 7.25 (d, J=5.38 Hz, 2H), 7.13 (d, J=7.83 Hz, 1H), 7.09 (d, J=9.78 Hz, 1H), 6.96 (dt, J=2.45, 8.31 Hz, 1H), 4.37 (s, 2H), 4.01 (s, 3H) ¹³C NMR (126 MHz, CDCl₃) δ 162.7, 159.7, 156.9, 151.7, 150.7, 143.5, 138.0, 135.5, 130.2, 124.8, 124.4, 116.2, 114.8, 102.7, 36.8, 34.2

General Procedure C

To a dry flask under nitrogen charged with ethyl 5-isothiocyanato-1-methyl-1H-pyrazole-4-carboxylate (50 mg, 0.237 mmol) and 2 mL dry DMF was added aniline (25.8 mg, 0.237 mmol) by syringe. The reaction was stirred at RT for 1 hr and then cooled to 0° C. 60 wt. % NaH (28.4 mg, 0.710 mmol) was added and the flask was stirred at 0° C. for 20 min then allowed to warm to RT and stirred for 3H. The reaction was quenched with sat. aq. NH₄Cl and extracted 2× with ethyl acetate. The combined organics were dried with sodium sulfate and the solvent removed. The residue was dissolved in 2 mL DMF and 3-fluorobenzyl bromide (0.029 mL, 0.237 mmol) and sodium bicarbonate (80 mg, 0.947 mmol) were added. The mixture was stirred at RT overnight at which point the reaction was complete by HPLC. The mixture was diluted with water and extracted 2× with EtOAc. The combined organics were washed 3× with brine, dried over sodium sulfate, and the solvent removed. The crude product was purified by flash chromatography (0-100% EtOAc in Hex) yielding the titled compound. This procedure was used for Sub-Examples 33-35.

Sub-Example 33: CCG: 257909

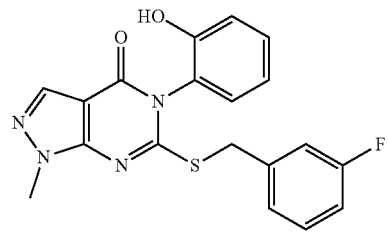 [SMILES: Cn1ncc2c(=O)n(-c3ccccc3O)c(SCc3cccc(F)c3)nc21]

6-((3-fluorobenzyl)thio)-5-(2-hydroxyphenyl)-1-methyl-1H-pyrazolo[3,4-d]pyrimidin-4(5H)-one as a white solid (140 mg, 0.366 mmol, 38.7% yield). MS (ESI): m/z 383.0975 [M+H]⁺ ¹H NMR (400 MHz, DMSO-d$_6$) δ 10.03 (s, 1H), 8.03 (s, 1H), 7.25-7.40 (m, 4H), 7.19 (d, J=7.43 Hz, 1H), 7.08 (t, J=8.41 Hz, 1H), 6.99 (d, J=7.83 Hz, 1H), 6.92 (t, J=7.43 Hz, 1H), 4.35-4.48 (m, 2H), 3.96 (s, 3H) $^{13}$C NMR (101 MHz, DMSO-d$_6$) δ 162.4, 162.3, 156.9, 154.3, 150.9, 140.4, 135.1, 131.8, 131.2, 130.7, 125.8, 122.8, 119.9, 117.3, 116.4, 114.5, 102.9, 35.7, 34.3

Sub-Example 34: CCG: 257914

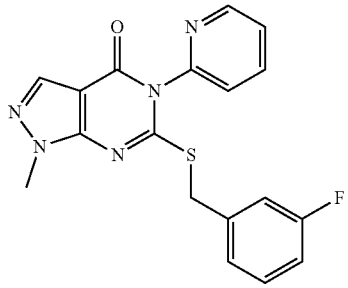 [SMILES: Cn1ncc2c(=O)n(-c3ccccn3)c(SCc3cccc(F)c3)nc21]

6-((3-fluorobenzyl)thio)-1-methyl-5-(pyridin-2-yl)-1H-pyrazolo[3,4-d]pyrimidin-4(5H)-one White needles (138 mg, 0.376 mmol, 39.7% yield) MS (ESI): m/z 368.0977 [M+H]$^+$ $^1$H NMR (500 MHz, CDCl$_3$) δ 8.69 (dd, J=1.47, 4.89 Hz, 1H), 8.03 (s, 1H), 7.92 (dt, J=1.96, 7.58 Hz, 1H), 7.44-7.49 (m, 1H), 7.38 (d, J=7.83 Hz, 1H), 7.21-7.29 (m, 1H), 7.13 (d, J=7.83 Hz, 1H), 7.06-7.11 (m, 1H), 6.95 (dt, J=2.20, 8.44 Hz, 1H), 4.38 (s, 2H), 4.01 (s, 3H) $^{13}$C NMR (126 MHz, CDCl$_3$) δ 162.7, 160.2, 157.6, 150.9, 150.3, 149.4, 138.8, 138.2, 135.5, 130.1, 125.1, 124.9, 124.8, 116.2, 114.7, 103.0, 36.7, 34.2

Sub-Example 35: CCG: 258081

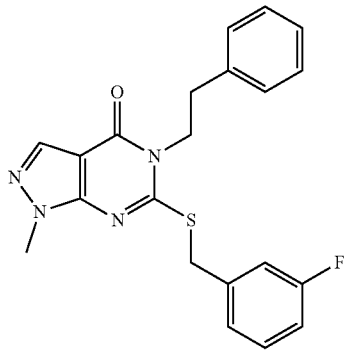 [SMILES: Cn1ncc2c(=O)n(CCc3ccccc3)c(SCc3cccc(F)c3)nc21]

6-((3-fluorobenzyl)thio)-1-methyl-5-phenethyl-1H-pyrazolo[3,4-d]pyrimidin-4(5H)-one White Needles (67 mg, 0.170 mmol, 71.8% yield) MS (ESI): m/z 368.0977 [M+H]$^+$ $^1$H NMR (500 MHz, CDCl$_3$) δ 8.00 (s, 1H), 7.27-7.36 (m, 5H), 7.23 (t, J=7.58 Hz, 2H), 7.17 (d, J=9.78 Hz, 1H), 7.00 (dt, J=2.20, 8.44 Hz, 1H), 4.48 (s, 2H), 4.24-4.31 (m, 2H), 3.96 (s, 3H), 2.97-3.04 (m, 2H) $^{13}$C NMR (126 MHz, CDCl$_3$) δ 162.8, 159.7, 157.4, 150.5, 138.4, 137.7, 135.0, 130.2, 128.9, 128.7, 126.8, 124.8, 116.2, 114.8, 102.8, 45.7, 36.4, 34.2, 34.0

Sub-Example 36: CCG: 257726

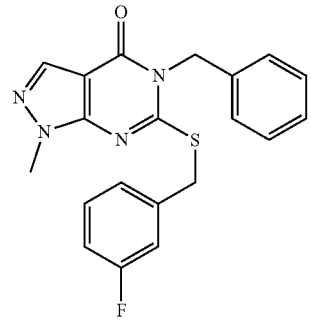 [SMILES: Cn1ncc2c(=O)n(Cc3ccccc3)c(SCc3cccc(F)c3)nc21]

5-benzyl-6-((3-fluorobenzyl)thio)-1-methyl-1H-pyrazolo[3,4-d]pyrimidin-4(5H)-one To a dry flask under nitrogen charged with ethyl 5-isothiocyanato-1-methyl-1H-pyrazole-4-carboxylate (50 mg, 0.237 mmol) and 2 mL dry DMF was added benzylamine (0.026 mL, 0.237 mmol) by syringe. The reaction was stirred at RT for 1 hr and then cooled to 0° C. 60 wt. % NaH (18.93 mg, 0.473 mmol) was added and the flask was stirred at 0° C. for 20 min then allowed to warm to RT and stirred for 3H. The flask was once again cooled to 0° C. and 3-fluorobenzyl bromide (0.029 mL, 0.237 mmol) was added by syringe. The mixture was stirred at 0° C. for 30 min at which point the reaction was complete by HPLC. The reaction was diluted with 10 mL water and extracted 2× with 10 mL EtOAc. The combined organic portion was washed 3× with brine, dried over sodium sulfate and the solvent removed. The crude product was purified by crystallization from ethanol yielding the titled compound as a white crystalline solid (51 mg, 0.134 mmol, 56.6% yield). MS (ESI): m/z 381.0 [M+H]$^+$. $^1$H NMR (500 MHz, CDCl$_3$) δ 8.02 (s, 1H), 7.22-7.35 (m, 6H), 7.16 (d, J=7.83 Hz, 1H), 7.11 (d, J=9.78 Hz, 1H), 6.97 (t, J=8.31 Hz, 1H), 5.36 (br. s., 2H), 4.43 (s, 2H), 3.96 (s, 3H) $^{13}$C NMR (126 MHz, CDCl$_3$) δ 162.7, 160.4, 157.8, 150.5, 138.4, 135.4, 135.2, 130.1, 128.6, 127.7, 127.3, 124.7, 116.1, 114.7, 102.6, 46.6, 36.5, 34.0

Sub-Example 37: CCG: 258074

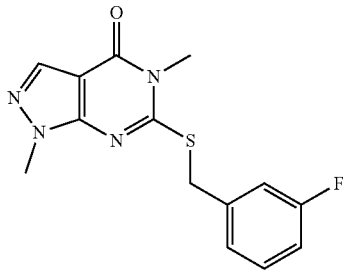 [SMILES: Cn1c(SCc2cccc(F)c2)nc2c(cnn2C)c1=O]

6-((3-fluorobenzyl)thio)-1,5-dimethyl-1H-pyrazolo[3,4-d]pyrimidin-4(5H)-one

Ethyl 5-isothiocyanato-1-methyl-1H-pyrazole-4-carboxylate (100 mg, 0.473 mmol) was dissolved in 1 mL 8N methylamine in ethanol and stirred at RT for 1 hour. The volatiles were removed and the residue was dissolved in 1 mL DMF to which sodium bicarbonate (80 mg, 0.947 mmol) and 3-fluorobenzyl bromide (69.7 µl, 0.568 mmol) were added. The reaction was stirred for one hour at which point the product was precipitated out by the addition of water. The precipitate was collected by filtration, washed with water followed by hexanes. The precipitate was then taken up in dichloromethane and dried with sodium sulfate. The solvent was removed to yield the titled compound as a white crystalline solid (122 mg, 0.401 mmol, 85% yield). MS (ESI): m/z 305.1 [M+H]$^+$ $^1$H NMR (500 MHz, CDCl$_3$) δ 7.99 (s, 1H), 7.29-7.35 (m, 1H), 7.24 (d, J=7.83 Hz, 1H), 7.19 (d, J=9.78 Hz, 1H), 7.00 (dt, J=2.45, 8.56 Hz, 1H), 4.49 (s, 2H), 3.96 (s, 3H), 3.55 (s, 3H) $^{13}$C NMR (126 MHz, CDCl$_3$) δ 162.8, 160.3, 157.6, 150.5, 138.4, 135.0, 130.2, 124.8, 116.2, 114.8, 102.5, 36.3, 34.0, 29.7

Preparation 11

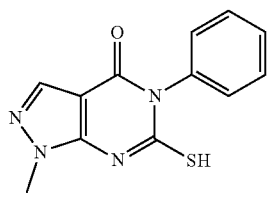 [SMILES: Cn1ncc2c(=O)n(-c3ccccc3)c(S)nc21]

6-mercapto-1-methyl-5-phenyl-1H-pyrazolo[3,4-d]pyrimidin-4(5H)-one

To a solution of ethyl 5-amino-1-methyl-1H-pyrazole-4-carboxylate (1 g, 5.91 mmol) in 15 mL DMF at 0° C. was slowly added 60 wt. % NaH (0.591 g, 14.78 mmol) against a counterflow of nitrogen. The reaction was stirred for 1 hr at 0° C. at which point isothiocyanatobenzene (0.706 mL, 5.91 mmol) was added and the reaction was warmed to 50° C. and stirred overnight. The reaction was quenched by adding a couple mL of sat. aq. ammonium chloride then the solvents were distilled off under high vacuum. The residue obtained was washed 3× with hexanes to remove the mineral oil then taken up in DCM and filtered to remove salts. After the DCM was evaporated the crude was triturated from hot EtOAc yielding the titled compound as a white solid (600 mg, 2.323 mmol, 39.3% yield)$^1$H NMR (400 MHz, DMSO-d$_6$) δ 8.23 (br. s., 1H), 7.65 (s, 1H), 7.33 (t, J=7.60 Hz, 2H), 7.22 (t, J=7.40 Hz, 1H), 6.96 (d, J=8.22 Hz, 2H), 3.71 (s, 3H)

Sub-Example 38: CCG: 258086

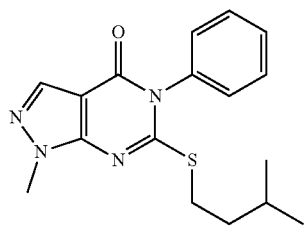 [SMILES: CC(C)CCSc1nc2c(cnn2C)c(=O)n1-c1ccccc1]

6-(isopentylthio)-1-methyl-5-phenyl-1H-pyrazolo[3,4-d]pyrimidin-4(5H)-one

To a flask under nitrogen charged with 6-mercapto-1-methyl-5-phenyl-1H-pyrazolo[3,4-d]pyrimidin-4(5H)-one (50 mg, 0.194 mmol), sodium bicarbonate (32.5 mg, 0.387 mmol) and 1 mL DMF was added 1-bromo-3-methylbutane (0.026 mL, 0.213 mmol) by syringe. The reaction was stirred at RT overnight. The next day the reaction was diluted with 10 mL water and extracted 2× with EtOAc. The combined organics were washed 3× with brine, dried over sodium sulfate, and the volatiles removed. The crude residue obtained was recrystallized from ethanol yielding the titled compound as a white solid (20 mg, 0.061 mmol, 31.5% yield). MS (ESI): m/z 329.1 [M+H]$^+$ $^1$H NMR (500 MHz, CDCl$_3$) δ 8.03 (s, 1H), 7.48-7.58 (m, J=4.90 Hz, 3H), 7.22-7.31 (m, J=3.90 Hz, 2H), 3.99 (s, 3H), 3.13 (t, J=7.80 Hz, 2H), 1.67 (sptd, J=6.50, 7.30 Hz, 1H), 1.59 (td, J=6.50, 7.80 Hz, 2H), 0.95 (d, J=6.85 Hz, 6H) $^{13}$C NMR (126 MHz, CDCl$_3$) δ 162.3, 157.8, 151.1, 135.8, 135.3, 129.8, 129.6, 129.3, 102.7, 37.5, 33.9, 31.0, 27.7, 22.2

Preparation 12

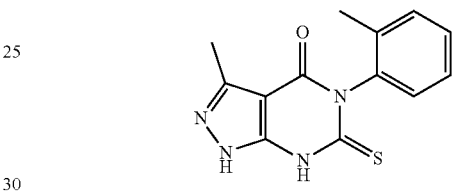

3-methyl-6-thioxo-5-(o-tolyl)-6,7-dihydro-2H-pyrazolo[3,4-d]pyrimidin-4(5H)-one To a dry flask was added ethyl 3-amino-5-methyl-1H-pyrazole-4-carboxylate (200 mg, 1.182 mmol), 1 mL dry Toluene, 1-isothiocyanato-2-methylbenzene (158 µl, 1.182 mmol) and 60 wt. % NaH (95 mg, 2.364 mmol). The reaction was refluxed overnight. At this point the mixture was diluted with 50 mL sat. NH4Cl and extracted 3× with ethyl acetate. The combined organics were washed with brine and dried over sodium sulfate. The solvent was removed yielding a yellow viscous oily residue. The crude material was purified by flash (0-50% EA in Hex) yielding the titled compound as a yellow solid (95 mg, 0.349 mmol, 29.5% yield). $^1$H NMR (400 MHz, DMSO-d$_6$) δ 13.43 (br. s., 1H), 13.29 (br. s., 1H), 7.17-7.36 (m, 3H), 7.08 (d, J=6.65 Hz, 1H), 2.46 (s, 3H), 2.01 (s, 3H)

Sub-Example 39: CCG: 257221

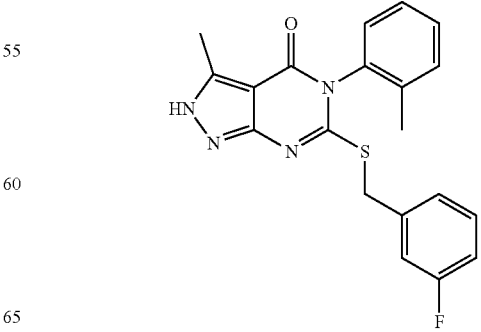

6-((3-fluorobenzyl)thio)-3-methyl-5-(o-tolyl)-2H-pyrazolo[3,4-d]pyrimidin-4(5H)-one To a dry flask under nitrogen charged with 3-methyl-6-thioxo-5-(o-tolyl)-6,7-dihydro-2H-pyrazolo[3,4-d]pyrimidin-4(5H)-one (60 mg, 0.220 mmol) and potassium carbonate (60.9 mg, 0.441 mmol) was added 2 mL DMF and 1-(bromomethyl)-3-fluorobenzene (27.0 µl, 0.220 mmol) by syringe. The flask was heated to 80° C. for 4 hours at which point the reaction was complete by HPLC. The reaction was diluted with water and extracted 2× with ethyl acetate. The combined organics were extracted 3× with brine and dried over sodium sulfate. The solvent was removed yielding an oily residue. The crude was purified by flash eluting with 60% EA in Hex yielding the titled compound as a white solid (23 mg, 0.060 mmol, 27.4% yield). MS (ESI): m/z 381.0 [M+H]+ 1H NMR (400 MHz, CDCl$_3$) δ 7.40 (t, J=7.00 Hz, 1H), 7.34 (d, J=6.65 Hz, 1H), 7.31 (t, J=7.40 Hz, 1H), 7.20 (dq, J=1.96, 8.00 Hz, 1H), 7.18 (d, J=7.43 Hz, 1H), 7.07 (d, J=7.83 Hz, 1H), 7.02 (td, J=2.00, 9.78 Hz, 1H), 6.91 (dt, J=2.35, 8.41 Hz, 1H), 4.29 (d, J=13.30 Hz, 1H), 4.34 (d, J=13.30 Hz, 1H), 2.65 (s, 3H), 2.12 (s, 3H) 13C NMR (101 MHz, CDCl$_3$) δ 163.8, 161.6, 161.4, 158.4, 154.2, 146.4, 138.1, 137.0, 134.3, 131.5, 130.2, 129.5, 127.5, 124.8, 116.0, 114.5, 101.1, 36.5, 17.4, 13.1

Sub-Example 40: CCG: 257722

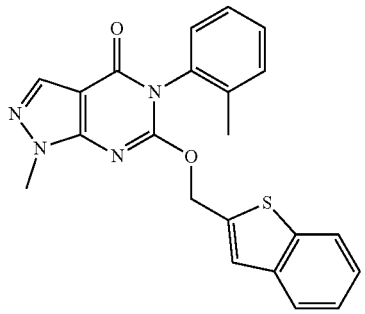 [SMILES: Cc1ccccc1-n1c(OCc2cc3ccccc3s2)nc2c(cnn2C)c1=O]

6-(benzo[b]thiophen-2-ylmethoxy)-1-methyl-5-(o-tolyl)-1H-pyrazolo[3,4-d]pyrimidin-4(5H)-one To a dry flask under nitrogen in an ice bath charged with 60 wt. % NaH (15.08 mg, 0.377 mmol) and benzo[b]thiophen-2-ylmethanol (38.7 mg, 0.236 mmol) was added 1 mL of DMF by syringe. The mixture was stirred for 10 minutes at which point solid 1-methyl-6-(methylsulfonyl)-5-(o-tolyl)-1H-pyrazolo[3,4-d]pyrimidin-4(5H)-one (75 mg, 0.236 mmol) was added quickly. The mixture was stirred overnight at RT. The following day the mixture was diluted with EtOAc and washed 3× with brine. The crude was purified by flash (EA in Hex) yielding the titled compound a white solid (54 mg, 0.134 mmol, 57.0% yield). MS (ESI): m/z 403.1 [M+H]+ 1H NMR (500 MHz, cdcl$_3$) δ 8.02 (s, 1H), 7.76-7.83 (m, 1H), 7.69-7.76 (m, 1H), 7.28-7.39 (m, 5H), 7.24 (s, 1H), 7.09 (d, J=7.34 Hz, 1H), 5.73 (d, J=12.72 Hz, 1H), 5.61 (d, J=12.72 Hz, 1H), 4.03 (s, 3H), 2.01 (s, 3H)
13C NMR (126 MHz, cdcl$_3$) δ 157.5, 155.2, 150.8, 140.5, 138.7, 137.6, 135.8, 135.7, 133.9, 131.0, 129.2, 128.4, 127.0, 124.9, 124.9, 124.5, 123.8, 122.4, 102.1, 65.6, 34.1, 17.4

Sub-Example 41: CCG: 258463

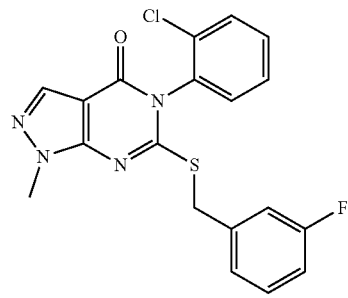 [SMILES: Cn1ncc2c(=O)n(-c3ccccc3Cl)c(SCc3cccc(F)c3)nc21]

5-(2-chlorophenyl)-6-((3-fluorobenzyl)thio)-1-methyl-1H-pyrazolo[3,4-d]pyrimidin-4(5H)-one General Procedure B
White crystalline solid. 83% yield. MS (ESI): m/z 401.1 [M+H]+ 1H NMR (500 MHz, Chloroform-d) δ 8.04 (s, 1H), 7.58 (dd, J=1.47, 7.83 Hz, 1H), 7.48 (dt, J=1.71, 7.70 Hz, 1H), 7.43 (dt, J=1.47, 7.58 Hz, 1H), 7.33 (d, J=7.83 Hz, 1H), 7.23-7.30 (m, 1H), 7.15 (d, J=7.34 Hz, 1H), 7.10 (d, J=9.78 Hz, 1H), 6.95 (dt, J=1.96, 8.31 Hz, 1H), 4.32-4.42 (m, 2H), 4.01 (s, 3H) 13C NMR (126 MHz, Chloroform-d) δ 162.67 (d, J=246.8 Hz), 160.82, 156.77, 150.91, 138.29 (d, J=7.3 Hz), 135.54, 133.78, 133.22, 131.56, 131.21, 130.73, 130.05 (d, J=8.5 Hz), 128.07, 124.69 (d, J=2.9 Hz), 116.07 (d, J=22.1 Hz), 114.63 (d, J=21.0 Hz), 102.72, 36.59, 34.15.

Sub-Example 42: CCG:258464

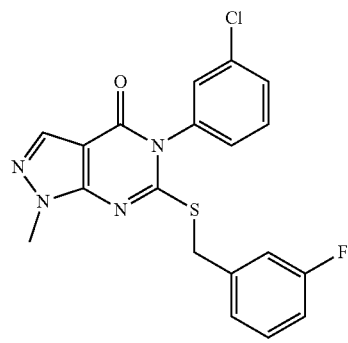 [SMILES: Cn1ncc2c(=O)n(-c3cccc(Cl)c3)c(SCc3cccc(F)c3)nc21]

5-(3-chlorophenyl)-6-((3-fluorobenzyl)thio)-1-methyl-1H-pyrazolo[3,4-d]pyrimidin-4(5H)-one General Procedure B
White crystalline solid. 44% yield. MS (ESI): m/z 401.1 [M+H]+ 1H NMR (500 MHz, Chloroform-d) δ 8.03 (s, 1H), 7.51 (td, J=1.60, 8.00 Hz, 1H), 7.47 (t, J=8.00 Hz, 1H), 7.26-7.32 (m, 2H), 7.18 (td, J=1.53, 7.70 Hz, 1H), 7.15 (d, J=7.83 Hz, 1H), 7.11 (td, J=2.08, 9.54 Hz, 1H), 6.98 (dt, J=2.69, 8.44 Hz, 1H), 4.32-4.41 (m, 2H), 4.02 (s, 3H) 13C NMR (126 MHz, Chloroform-d) δ 162.70 (d, J=246.8 Hz), 160.84, 157.42, 150.77, 138.20 (d, J=7.6 Hz), 136.53, 135.47, 135.27, 130.66, 130.47, 130.15 (d, J=8.1 Hz), 129.77, 127.77, 124.78 (d, J=3.2 Hz), 116.19 (d, J=21.7 Hz), 114.74 (d, J=21.0 Hz), 102.80, 36.93, 34.18.

Sub-Example 43: CCG:258465

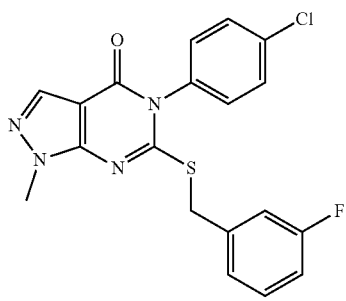 [SMILES: Cn1ncc2c(=O)n(-c3ccc(Cl)cc3)c(SCc3cccc(F)c3)nc21]

5-(4-chlorophenyl)-6-((3-fluorobenzyl)thio)-1-methyl-1H-pyrazolo[3,4-d]pyrimidin-4(5H)-one General Procedure B White crystalline solid. 44% yield. MS (ESI): m/z 401.1 [M+H]+ 1H NMR (500 MHz, Chloroform-d) δ 8.02 (s, 1H), 7.49 (d, J=8.31 Hz, 2H), 7.24-7.30 (m, 1H), 7.20 (d, J=8.31 Hz, 2H), 7.13 (d, J=7.34 Hz, 1H), 7.09 (d, J=9.78 Hz, 1H), 6.96 (dt, J=2.45, 8.31 Hz, 1H), 4.34 (s, 2H), 4.01 (s, 3H) 13C NMR (126 MHz, Chloroform-d) δ 162.69 (d, J=246.7 Hz), 160.96, 157.53, 150.81, 138.22 (d, J=7.6 Hz), 136.33, 135.44, 133.89, 130.75, 130.17, 130.11, 124.76 (d, J=2.9 Hz), 116.16 (d, J=22.1 Hz), 114.73 (d, J=21.0 Hz), 102.81, 36.92, 34.16.

Sub-Example 44: CCG:258466

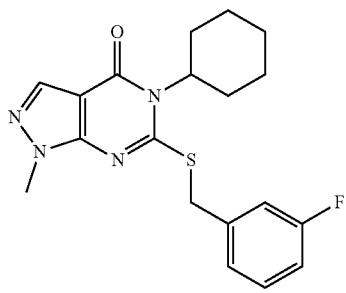 [SMILES: Cn1ncc2c(=O)n(C3CCCCC3)c(SCc3cccc(F)c3)nc21]

General Procedure C

White Needles (22 mg, 0.059 mmol, 20.80% yield) MS (ESI): m/z 373.1498 [M+H]+ 1H NMR (500 MHz, Chloroform-d) δ 7.93 (br. s., 1H), 7.28-7.37 (m, 1H), 7.23 (d, J=7.34 Hz, 1H), 7.18 (d, J=9.29 Hz, 1H), 7.00 (t, J=7.83 Hz, 1H), 4.44 (br. s., 2H), 4.07-4.19 (m, 1H), 3.92 (s, 3H), 2.69 (d, J=10.27 Hz, 2H), 1.88 (br. s., 2H), 1.59-1.77 (m, 3H), 1.30 (br. s., 3H) 13C NMR (126 MHz, Chloroform-d) δ 162.8, 160.2, 158.4, 150.0, 138.3, 134.8, 130.2, 124.9, 116.2, 114.7, 104.2, 62.2, 37.2, 33.9, 28.8, 26.5, 25.0

Sub-Example 45: CCG: 258467

5-cyclopentyl-6-((3-fluorobenzyl)thio)-1-methyl-1H-pyrazolo[3,4-d]pyrimidin-4(5H)-one General Procedure C Yellowish clear sheets (44 mg, 0.123 mmol, 43.2% yield) MS (ESI): m/z 359.1346 [M+H]+ 1H NMR (500 MHz, Chloroform-d) δ 7.93 (s, 2H), 7.32 (dq, J=1.90, 7.30 Hz, 1H), 7.23 (d, J=7.34 Hz, 1H, 7.18 (d, J=9.29 Hz, 1H), 7.00 (dt, J=1.90, 8.30 Hz, 1H), 4.79 (quin, J=8.44 Hz, 1H), 4.45 (s, 2H), 3.93 (s, 3H), 2.25-2.37 (m, 2H), 2.01-2.12 (m, 2H), 1.85-1.96 (m, 2H), 1.55-1.66 (m, 2H) 13C NMR (126 MHz, Chloroform-d) δ 162.8, 160.5, 157.8, 150.1, 138.3, 134.7, 130.1, 124.8, 116.2, 114.7, 104.0, 60.5, 37.1, 33.9, 28.8, 26.0

Sub-Example 46: CCG: 258468

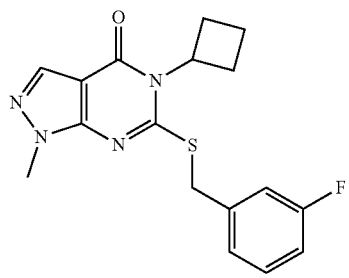 [SMILES: Cn1ncc2c(=O)n(C3CCC3)c(SCc3cccc(F)c3)nc21]

5-cyclobutyl-6-((3-fluorobenzyl)thio)-1-methyl-1H-pyrazolo[3,4-d]pyrimidin-4(5H)-one General Procedure C White crystalline solid (11 mg, 0.032 mmol, 11.24% yield) MS (ESI): m/z 345.1182 [M+H]+ 1H NMR (500 MHz, Chloroform-d) δ 7.95 (s, 1H), 7.31 (q, J=7.5 Hz, 1H), 7.22 (d, J=7.7 Hz, 1H), 7.17 (d, J=9.6 Hz, 1H), 6.99 (td, J=8.4, 2.4 Hz, 1H), 4.91 (p, J=8.7 Hz, 1H), 4.44 (s, 2H), 3.92 (s, 3H), 3.24 (pd, J=9.6, 2.7 Hz, 3H), 2.40-2.24 (m, 3H), 2.11-1.94 (m, 2H), 1.76 (h, J=9.4 Hz, 1H). 13C NMR (126 MHz, Chloroform-d) δ 162.73 (d, J=246.7 Hz), 160.20, 158.96, 149.94, 138.38 (d, J=7.4 Hz), 134.87, 130.14 (d, J=8.2 Hz), 124.81 (d, J=3.1 Hz), 116.19 (d, J=22.0 Hz), 114.71 (d, J=21.0 Hz), 103.87, 53.45, 36.93, 33.91, 27.66, 14.72.

Preparation 13

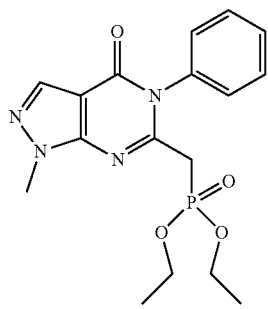 [SMILES: CCOP(=O)(Cc1nc2c(cnn2C)c(=O)n1-c1ccccc1)OCC]

Diethyl ((1-methyl-4-oxo-5-phenyl-4,5-dihydro-1H-pyrazolo[3,4-d]pyrimidin-6-yl)methyl)phosphonate 6-(chloromethyl)-1-methyl-5-phenyl-1H-pyrazolo[3,4-d]pyrimidin-4(5H)-one (250 mg, 0.910 mmol) and triethyl phosphite (318 μl, 1.820 mmol) were dissolved in 2 mL DMF and heated to 150° C. for 3 hours. The mixture was concentrated under vacuum and the crude residue was purified by flash chromatography (EtOAc in Hex) yielding the titled compound as a yellow solid (250 mg, 0.664 mmol, 73.0% yield).

Sub-Example 47: CCG: 258471

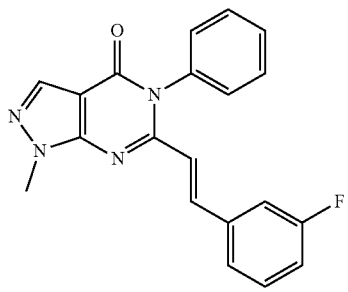 [SMILES: Cn1ncc2c(=O)n(-c3ccccc3)c(/C=C/c3cccc(F)c3)nc21]

(E)-6-(3-fluorostyryl)-1-methyl-5-phenyl-1H-pyrazolo[3,4-d]pyrimidin-4(5H)-one

A dry flask charged with 60% NaH in mineral oil (11.16 mg, 0.279 mmol) and diethyl ((1-methyl-4-oxo-5-phenyl-4,5-dihydro-1H-pyrazolo[3,4-d]pyrimidin-6-yl)methyl)phosphonate (100 mg, 0.266 mmol) was cooled to 0° C. and DMF was added by syringe. After stirring for 10 min 3-fluorobenzaldehyde (0.031 ml, 0.292 mmol) was added by syringe and the flask was allowed to warm to RT. After an hour the reaction went from yellow to brownish red and was complete by HPLC. Water was added to precipitate product which was collected by filtration, washed with additional water and hexanes, and then recrystallized from hot ethanol yielding the titled compound as a yellow crystalline solid (50 mg, 0.144 mmol, 54.3% yield). MS (ESI): m/z 347.1305 [M+H]+ 1H NMR (500 MHz, Chloroform-d) δ 8.10 (s, 1H), 7.91 (d, J=15.65 Hz, 2H), 7.53-7.64 (m, 3H), 7.22-7.34 (m, 3H), 7.09 (d, J=7.83 Hz, 1H), 7.02 (dt, J=2.45, 8.31 Hz, 1H), 6.96 (d, J=9.78 Hz, 1H), 6.34 (d, J=15.16 Hz, 2H), 4.10 (s, 3H) 13C NMR (126 MHz, Chloroform-d) δ 162.92 (d, J=247.3 Hz), 158.17, 154.11, 151.05, 139.17, 137.23 (d, J=7.5 Hz), 136.73, 135.40, 130.38 (d, J=8.4 Hz), 129.96, 129.54, 128.88, 123.80 (d, J=2.6 Hz), 120.96, 116.75 (d, J=21.5 Hz), 114.04 (d, J=21.8 Hz), 104.23, 34.17.

Sub-Example 48: CCG:258472

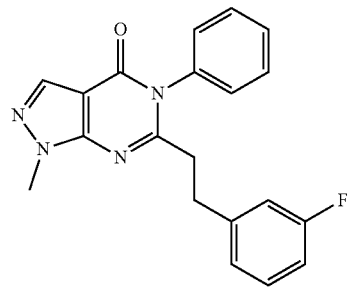 [SMILES: Cn1ncc2c(=O)n(-c3ccccc3)c(CCc3cccc(F)c3)nc21]

6-(3-fluorophenethyl)-1-methyl-5-phenyl-1H-pyrazolo[3,4-d]pyrimidin-4(5H)-one

A solution of (E)-6-(3-fluorostyryl)-1-methyl-5-phenyl-1H-pyrazolo[3,4-d]pyrimidin-4(5H)-one (40 mg, 0.115 mmol) and 10% Pd—C (36.9 mg, 0.035 mmol) in 5 mL methanol was degassed under vacuum and the flask back-filled with an H₂ Balloon. The mixture was stirred vigorously for 2 hours then filtered through Celite and concentrated yielding the titled compound as a white solid (27 mg, 0.078 mmol, 67.1% yield). MS (ESI): m/z 349.1461 [M+H]+ 1H NMR (400 MHz, Chloroform-d) δ 8.05 (s, 1H), 7.44-7.62 (m, 3H), 7.10-7.23 (m, 3H), 6.86 (t, J=8.41 Hz, 1H), 6.81 (d, J=7.83 Hz, 1H), 6.74 (d, J=10.17 Hz, 1H), 4.04 (s, 3H), 3.04 (t, J=7.83 Hz, 2H), 2.68 (t, J=7.83 Hz, 2H) 13C NMR (101 MHz, Chloroform-d) δ 162.7, 158.9, 158.3, 150.8, 142.8, 136.9, 135.1, 130.0, 129.8, 129.4, 128.4, 123.9, 115.3, 113.2, 104.0, 37.2, 34.1, 32.3.

Sub-Example 49: CCG:258473

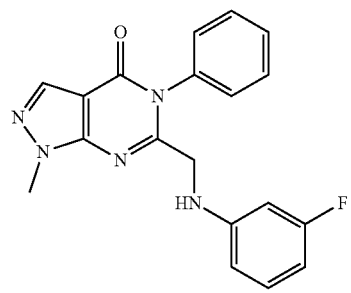 [SMILES: Cn1ncc2c(=O)n(-c3ccccc3)c(CNc3cccc(F)c3)nc21]

6-(((3-fluorophenyl)amino)methyl)-1-methyl-5-phenyl-1H-pyrazolo[3,4-d]pyrimidin-4(5H)-one A flask was charged with 1 mL DMF, Potassium Carbonate (151 mg, 1.092 mmol), Potassium Iodide (18.13 mg, 0.109 mmol), 6-(chloromethyl)-1-methyl-5-phenyl-1H-pyrazolo[3,4-d]pyrimidin-4(5H)-one (150 mg, 0.546 mmol) and was briefly vacuum degassed and put under nitrogen at which point 3-fluoroaniline (0.063 ml, 0.655 mmol) was added by syringe. The flask was heated at 50° C. for 24 hours. Water was added to precipitate the product which was collected by filtration yielding the titled compound as a light pink powder (177 mg, 0.507 mmol, 93% yield). MS (ESI): m/z 350.1415 [M+H]+ 1H NMR (500 MHz, Chloroform-d) δ 8.07 (s, 1H), 7.54-7.65 (m, 3H), 7.26 (d, J=6.36 Hz, 2H), 7.07 (q, J=7.83 Hz, 1H), 6.41 (t, J=8.07 Hz, 1H), 6.29 (d, J=7.83 Hz, 1H), 6.18 (d, J=11.25 Hz, 1H), 5.00 (br. s., 1H), 4.05 (s, 3H), 3.88 (d, J=5.20 Hz, 2H) 13C NMR (126 MHz, Chloroform-d) δ 163.9, 157.9, 156.2, 150.3, 148.4, 135.6, 135.4, 130.4, 130.3, 130.1, 128.3, 109.0, 104.8, 104.3, 99.9, 46.8, 34.3

Preparation 14

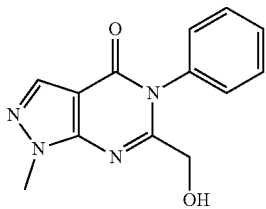 [SMILES: Cn1ncc2c(=O)n(-c3ccccc3)c(CO)nc21]

6-(hydroxymethyl)-1-methyl-5-phenyl-1H-pyrazolo[3,4-d]pyrimidin-4(5H)-one

A solution of 6-(chloromethyl)-1-methyl-5-phenyl-1H-pyrazolo[3,4-d]pyrimidin-4(5H)-one (100 mg, 0.364 mmol), Potassium Acetate (71.5 mg, 0.728 mmol), and Potassium Iodide (6.04 mg, 0.036 mmol) in 1 mL DMF was stirred at 40° C. overnight. The mixture was diluted with water and extracted twice with ethyl acetate. The combined organics were washed with brine and dried over sodium sulfate and concentrated. The crude residue was taken up in 1 mL or MeOH and 1 mL THF to which Potassium Carbonate (101 mg, 0.728 mmol) was added and the mixture was stirred overnight. The solvent was removed and the residue was taken up in ethyl acetate and washed with water and brine before drying over sodium sulfate. After concentrating the crude was purified by flash (EtOAc in Hex) yielding the titled compound as a white solid (45 mg, 0.176 mmol, 48.2% yield). 1H NMR (500 MHz, Chloroform-d) δ 8.10 (s, 1H), 7.52-7.60 (m, 3H), 7.18-7.24 (m, 2H), 4.15 (d, J=4.89 Hz, 2H), 4.06 (s, 3H), 3.76 (t, J=4.89 Hz, 1H)

Sub-Example 50: CCG:258474

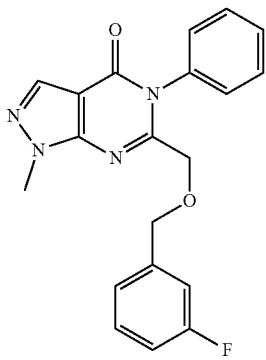 [SMILES: Cn1ncc2c(=O)n(-c3ccccc3)c(COCc3cccc(F)c3)nc21]

6-(((3-fluorobenzyl)oxy)methyl)-1-methyl-5-phenyl-1H-pyrazolo[3,4-d]pyrimidin-4(5H)-one To a flask at 0° C. charged with 3-fluorobenzyl bromide (0.108 ml, 0.878 mmol), 60% NaH in mineral oil (7.02 mg, 0.176 mmol) and 1 mL DMF under nitrogen was added by syringe 6-(hydroxymethyl)-1-methyl-5-phenyl-1H-pyrazolo[3,4-d]pyrimidin-4(5H)-one (45 mg, 0.176 mmol) in 1 mL DMF portion-wise over an hour. After 30 additional minutes the flask was warmed to RT and stirred for 2 h. The reaction was diluted with water and extracted 2× with EtOAc which was then washed 3× with brine before drying over sodium sulfate. The crude was purified by Flash (EtOAc in Hex) and purified further by recrystallization from EtOH yielding the titled compound as white crystalline solid (7 mg, 0.019 mmol, 10.94% yield). MS (ESI): m/z 365.1403 [M+H]+ 1H NMR (500 MHz, Chloroform-d) δ 8.09 (s, 1H), 7.49-7.56 (m, 3H), 7.21-7.31 (m, 3H), 6.94-7.01 (m, 3H), 4.41 (s, 2H), 4.21 (s, 2H), 4.06 (s, 3H) 13C NMR (126 MHz, Chloroform-d) δ 162.8, 158.2, 155.5, 150.7, 139.5, 135.9, 135.3, 129.9, 129.7, 129.6, 128.6, 123.1, 114.8, 114.6, 104.6, 72.6, 70.2, 34.3

Sub-Example 51: CCG: 258475

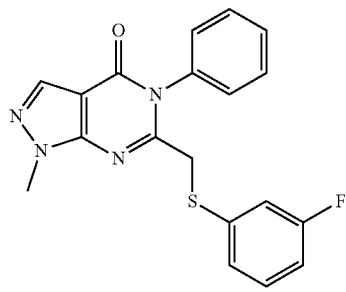

6-(((3-fluorophenyl)thio)methyl)-1-methyl-5-phenyl-1H-pyrazolo[3,4-d]pyrimidin-4(5H)-one 6-(chloromethyl)-1-methyl-5-phenyl-1H-pyrazolo[3,4-d]pyrimidin-4(5H)-one (60 mg, 0.218 mmol), Potassium Carbonate (45.3 mg, 0.328 mmol), and 3-fluorobenzenethiol (0.025 ml, 0.306 mmol) and 1 mL DMF were stirred overnight at 50° C. The product was precipitated by the addition of water and collected by filtration. The filtrate was recrystallized from EtOH yielding the titled compound as a white crystalline solid (24 mg, 0.066 mmol, 30.0% yield). MS (ESI): m/z 367.1025 [M+H]+ 1H NMR (400 MHz, Chloroform-d) δ 8.06 (s, 1H), 7.49-7.60 (m, 3H), 7.28-7.34 (m, 2H), 7.15-7.24 (m, 2H), 7.08 (d, J=7.83 Hz, 1H), 6.92 (dt, J=1.96, 8.41 Hz, 1H), 3.95 (s, 3H), 3.86 (s, 2H) 13C NMR (101 MHz, Chloroform-d) δ 164.1, 163.9, 161.4, 158.2, 155.9, 136.3, 135.3, 130.1, 129.9, 129.7, 128.9, 125.9, 117.2, 114.1, 104.3, 38.7, 34.1

Sub-Example 52: CCG: 258477

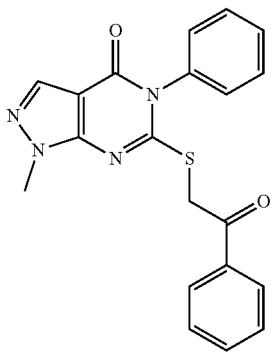 [SMILES: Cn1ncc2c(=O)n(-c3ccccc3)c(SCC(=O)c3ccccc3)nc21]

1-methyl-6-((2-oxo-2-phenylethyl)thio)-5-phenyl-1H-pyrazolo[3,4-d]pyrimidin-4(5H)-one Prepared in a Similar Manner to Sub-Example 38

Yellow needles (40 mg, 0.106 mmol, 54.9% yield). MS (ESI): m/z 377.1061 [M+H]+ $^1$H NMR (400 MHz, Chloroform-d) δ 8.06 (d, J=7.7 Hz, 2H), 7.96 (s, 1H), 7.65 (t, J=7.4 Hz, 1H), 7.60-7.49 (m, 5H), 7.39-7.30 (m, 2H), 4.49 (s, 2H), 3.46 (s, 3H). $^{13}$C NMR (101 MHz, Chloroform-d) δ 192.67, 161.08, 157.56, 150.61, 136.16, 135.54, 135.39, 133.84, 130.28, 129.88, 129.37, 128.92, 128.28, 102.84, 39.68, 33.51.

Sub-Example 53: CCG: 258478

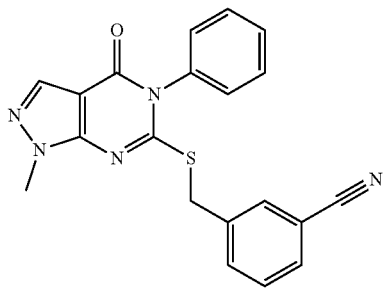 [SMILES: Cn1ncc2c(=O)n(-c3ccccc3)c(SCc3cccc(C#N)c3)nc21]

3-(((1-methyl-4-oxo-5-phenyl-4,5-dihydro-1H-pyrazolo[3,4-d]pyrimidin-6-yl)thio)methyl)benzonitrile Prepared in a Similar Manner to Sub-Example 38

White crystalline solid. (34 mg, 0.091 mmol, 47.0% yield) MS (ESI): m/z 374.1069 [M+H]+ $^1$H NMR (500 MHz, Chloroform-d) δ 8.02 (s, 1H), 7.70 (s, 1H), 7.61 (d, J=7.83 Hz, 1H), 7.51-7.57 (m, 4H), 7.39-7.45 (m, 1H), 7.22-7.29 (m, 2H), 4.35 (s, 2H), 4.01 (s, 3H) $^{13}$C NMR (126 MHz, Chloroform-d) δ 160.8, 157.5, 150.8, 138.0, 135.4, 135.4, 133.4, 132.7, 131.2, 130.2, 129.8, 129.4, 129.3, 118.4, 112.7, 103.0, 36.4, 34.2

Sub-Example 54: CCG:258479

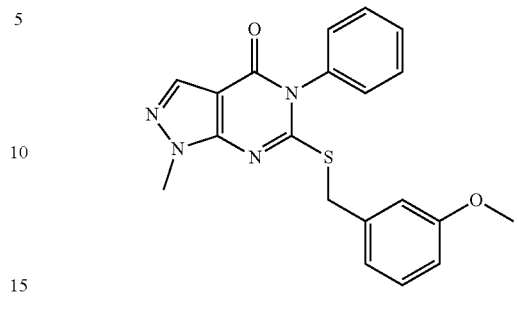

6-((3-methoxybenzyl)thio)-1-methyl-5-phenyl-1H-pyrazolo[3,4-d]pyrimidin-4(5H)-one Prepared in a Similar Manner to Sub-Example 38

White crystalline solid. (37 mg, 0.098 mmol, 50.5% yield) MS (ESI): m/z 379.1225 [M+H]+ $^1$H NMR (500 MHz, Chloroform-d) δ 8.01 (s, 1H), 7.47-7.53 (m, 3H), 7.23-7.28 (m, 2H), 7.20 (t, J=7.83 Hz, 1H), 6.93 (d, J=7.34 Hz, 1H), 6.90 (s, 1H), 6.78 (dd, J=2.20, 8.07 Hz, 1H), 4.33 (s, 2H), 4.01 (s, 3H), 3.76 (s, 3H) $^{13}$C NMR (126 MHz, Chloroform-d) δ 161.7, 159.6, 157.7, 150.9, 137.1, 135.5, 135.3, 129.9, 129.6, 129.5, 129.3, 121.4, 115.1, 112.7, 102.8, 55.1, 37.5, 34.0.

Sub-Example 55: CCG:258480

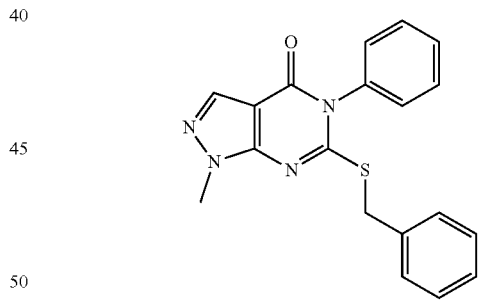

6-(benzylthio)-1-methyl-5-phenyl-1H-pyrazolo[3,4-d]pyrimidin-4(5H)-one

Prepared in a Similar Manner to Sub-Example 38

White crystalline solid. (28 mg, 0.080 mmol, 41.5% yield) MS (ESI): m/z 349.1127 [M+H]+ $^1$H NMR (500 MHz, Chloroform-d) δ 8.00 (s, 1H), 7.50 (s, 3H), 7.35 (d, J=7.34 Hz, 2H), 7.29 (t, J=7.30 Hz, 2H), 7.25 (s, 3H), 4.36 (s, 2H), 4.01 (s, 3H) $^{13}$C NMR (126 MHz, Chloroform-d) δ 161.7, 157.7, 150.9, 135.6, 135.5, 135.3, 129.9, 129.6, 129.3, 129.1, 128.5, 127.6, 102.8, 37.5, 34.0

Sub-Example 56: CCG: 258962

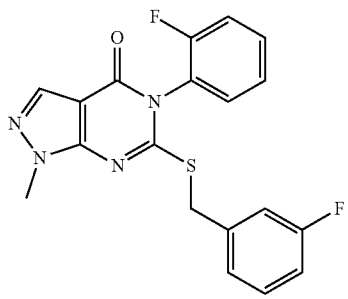 [SMILES: Cn1ncc2c(=O)n(-c3ccccc3F)c(SCc3cccc(F)c3)nc21]

6-((3-fluorobenzyl)thio)-5-(2-fluorophenyl)-1-methyl-1H-pyrazolo[3,4-d]pyrimidin-4(5H)-one General Procedure B White crystalline solid. 70% yield. MS (ESI): m/z 385.1 [M+H]+ 1H NMR (500 MHz, Chloroform-d) δ 8.03 (s, 1H), 7.57-7.49 (m, 1H), 7.36-7.20 (m, 4H), 7.14 (d, J=7.6 Hz, 1H), 7.10 (d, J=9.5 Hz, 1H), 6.96 (td, J=8.4, 2.5 Hz, 1H), 4.40 (d, J=13.7 Hz, 1H), 4.34 (d, J=13.6 Hz, 1H), 4.01 (s, 3H). 13C NMR (126 MHz, Chloroform-d) δ 162.70 (d, J=247.0 Hz), 161.09, 158.28 (d, J=253.4 Hz), 156.94, 150.92, 138.20 (d, J=7.6 Hz), 135.52, 132.33 (d, J=8.0 Hz), 131.24, 130.12 (d, J=8.5 Hz), 125.05 (d, J=3.9 Hz), 124.75 (d, J=3.1 Hz), 123.11 (d, J=14.1 Hz), 117.03 (d, J=19.5 Hz), 116.15 (d, J=22.2 Hz), 114.71 (d, J=21.0 Hz), 102.69, 36.73, 34.18.

Preparation 15

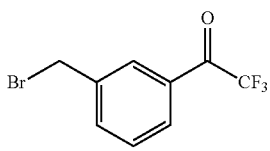

1-(3-(bromomethyl)phenyl)-2,2,2-trifluoroethanone 2,2,2-trifluoro-1-(m-tolyl)ethanone (250 mg, 1.329 mmol), NBS (248 mg, 1.395 mmol), and benzoyl peroxide (80 mg, 0.332 mmol) were refluxed for 4 h in 3 mL Carbon Tetrachloride at which point the mixture was cooled to RT and filtered. The filtrate was diluted with DCM and extracted with water and brine, dried over sodium sulfate and concentrated. The crude was purified by Flash (Hexanes) yielding an impure mixture predominantly composed of the titled compound as a yellow oil which was carried forward without further purification.

Sub-Example 57: CCG: 259004

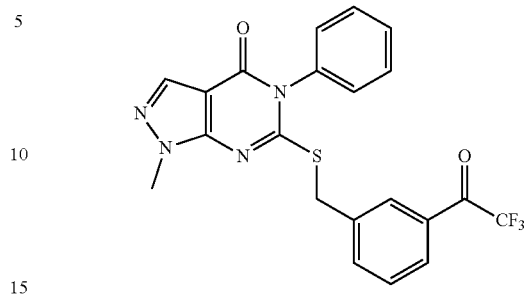

1-methyl-5-phenyl-6-((3-(2,2,2-trifluoroacetyl)benzyl)thio)-1H-pyrazolo[3,4-d]pyrimidin-4(5H)-one Prepared in a Similar Manner to Sub-Example 38

White crystalline solid. (75 mg, 0.169 mmol, 19.59% yield) MS (ESI): m/z 477.1201 [M+MeOH+H]+ 1H NMR (500 MHz, Chloroform-d) δ 8.15 (s, 1H), 8.02 (s, 1H), 7.96 (d, J=8.0 Hz, 1H), 7.71 (d, J=7.7 Hz, 1H), 7.57-7.47 (m, 5H), 7.34-7.19 (m, 1H), 4.41 (s, 2H), 4.03 (s, 3H) 13C NMR (126 MHz, Chloroform-d) δ 180.17 (q, J=35.0 Hz), 160.85, 157.60, 150.80, 138.12, 136.12, 135.45, 135.42, 130.66, 130.19, 130.08, 129.80, 129.42, 129.37, 129.34 (d, J=2.9 Hz), 116.54 (q, J=291.3 Hz), 103.01, 36.54, 34.18. (NMR sample solution treated overnight with 4 Å molecular sieves to eliminate hydrate)

Preparation 16

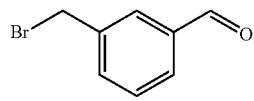

3-(bromomethyl)benzaldehyde

To a solution of 3-(bromomethyl)benzonitrile (212 mg, 1.081 mmol) in 2.5 mL Toluene was added dropwise 1M DIBAL-H in THF (1.5 ml, 1.5 mmol) at 0° C. After stirring at 0° C. for 2 h the reaction was diluted with DCM and 1N aq. HCl and stirred for 1 hour. The organic layer was washed with brine, dried over sodium sulfate, and concentrated yielding the titled compound as an orange oil. (200 mg, 0.970 mmol, 93% yield)

Sub-Example 58: CCG: 259006

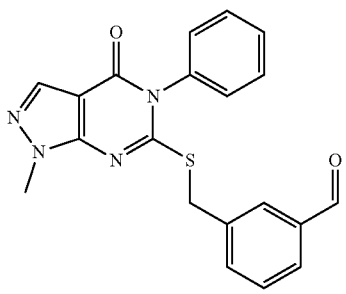 [SMILES: Cn1ncc2c(=O)n(-c3ccccc3)c(SCc3cccc(C=O)c3)nc21]

3-(((1-methyl-4-oxo-5-phenyl-4,5-dihydro-1H-pyrazolo[3,4-d]pyrimidin-6-yl)thio)methyl)benzaldehyde Prepared in a Similar Manner to Sub-Example 38

White solid. (46 mg, 0.122 mmol, 31.6% yield) MS (ESI): m/z 377.1061 [M+H]$^+$ 1H NMR (400 MHz, Chloroform-d) δ 9.99 (s, 1H), 8.01 (s, 1H), 7.95 (s, 1H), 7.76 (d, J=7.6 Hz, 1H), 7.64 (d, J=7.7 Hz, 1H), 7.56-7.43 (m, 4H), 7.32-7.18 (m, 2H), 4.40 (s, 2H), 4.03 (s, 3H) 13C NMR (101 MHz, Chloroform-d) δ 191.84, 161.10, 157.67, 150.84, 137.51, 136.54, 135.46, 135.39, 135.09, 130.16, 129.79, 129.77, 129.66, 129.37, 129.35, 102.98, 36.77, 34.24.

Preparation 17

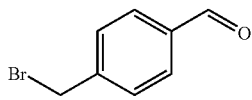

4-(bromomethyl)benzaldehyde

To a solution of 4-(bromomethyl)benzonitrile (200 mg, 1.020 mmol) in 2.5 mL Toluene was added dropwise 1M DIBAL-H in THF (1.122 ml, 1.122 mmol) at 0° C. After stirring at 0° C. for 2 h the reaction was diluted with DCM and 1N aq. HCl and stirred for 1 hour. The organic layer was washed with brine, dried over sodium sulfate, and concentrated yielding the titled compound as a white solid. (193 mg, 0.970 mmol, 95% yield)

Sub-Example 59: CCG: 259007

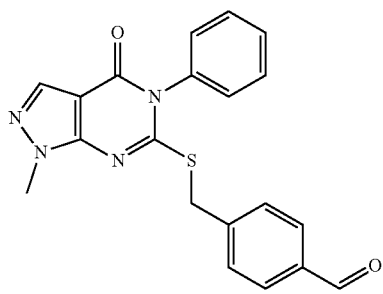 [SMILES: Cn1ncc2c(=O)n(-c3ccccc3)c(SCc3ccc(C=O)cc3)nc21]

4-(((1-methyl-4-oxo-5-phenyl-4,5-dihydro-1H-pyrazolo[3,4-d]pyrimidin-6-yl)thio)methyl)benzaldehyde Prepared in a Similar Manner to Sub-Example 38

White solid. (62 mg, 0.165 mmol, 42.5% yield) MS (ESI): m/z 377.1061 [M+H]$^+$ 1H NMR (400 MHz, Chloroform-d) δ 9.95 (s, 1H), 7.97 (s, 1H), 7.81 (d, J=7.8 Hz, 2H), 7.56-7.49 (m, 5H), 7.31-7.16 (m, 2H), 4.41 (s, 2H), 3.99 (s, 3H). 13C NMR (101 MHz, Chloroform-d) δ 191.39, 160.89, 157.44, 150.62, 143.07, 135.44, 135.27, 135.14, 130.00, 129.75, 129.61(2 overlapping), 129.19, 102.74, 36.84, 33.98.

Sub-Example 60: CCG: 259011

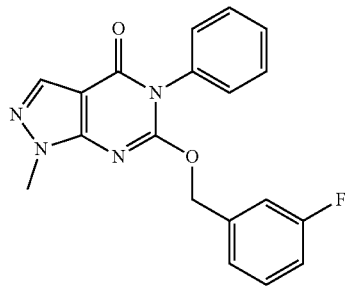 [SMILES: Cn1ncc2c(=O)n(-c3ccccc3)c(OCc3cccc(F)c3)nc21]

6-((3-fluorobenzyl)oxy)-1-methyl-5-phenyl-1H-pyrazolo[3,4-d]pyrimidin-4(5H)-one

Prepared in a Similar Manner to Sub-Example 24

White Solid (10 mg, 0.029 mmol, 8.69% yield) MS (ESI): m/z 351.1252 [M+H]$^+$ 1H NMR (500 MHz, Chloroform-d) δ 8.00 (s, 1H), 7.59-7.43 (m, 3H), 7.32-7.24 (m, 1H), 7.22 (d, J=7.5 Hz, 2H), 7.04-6.90 (m, 2H), 6.84 (d, J=9.6 Hz, 1H), 5.41 (s, 2H), 3.94 (s, 3H). 13C NMR (126 MHz, Chloroform-d) δ 162.73 (d, J=246.7 Hz), 157.90, 155.24, 150.75, 137.55 (d, J=7.6 Hz), 135.64, 134.86, 130.08 (d, J=8.3 Hz), 129.38, 128.95, 128.35, 122.58 (d, J=3.0 Hz), 115.15 (d, J=21.1 Hz), 114.12 (d, J=22.3 Hz), 102.06, 69.24, 33.90.

Sub-Example 61: CCG:259122

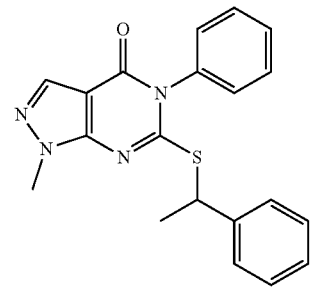 [SMILES: CC(Sc1nc2c(cnn2C)c(=O)n1-c1ccccc1)c1ccccc1]

1-methyl-5-phenyl-6-((1-phenylethyl)thio)-1H-pyrazolo[3,4-d]pyrimidin-4(5H)-one

Prepared in a Similar Manner to Sub-Example 38

White Solid (183 mg, 0.505 mmol, 65.2% yield) MS (ESI): m/z 363.1278 [M+H]$^+$ 1H NMR (500 MHz, Chloroform-d) δ 7.99 (s, 1H), 7.64-7.45 (m, 3H), 7.42-7.35 (m, 2H), 7.34-7.22 (m, 4H), 7.18 (d, J=6.9 Hz, 1H), 5.02 (q, J=7.2 Hz, 1H), 4.00 (s, 3H), 1.70 (d, J=7.1 Hz, 3H). 13C NMR (126 MHz, Chloroform-d) δ 161.50, 157.82, 151.05, 142.12, 135.64, 135.36, 129.93, 129.72, 129.65, 129.41, 129.38, 128.53, 127.56, 127.52, 102.88, 46.89, 34.07, 21.97.

Sub-Example 62: CCG: 259123

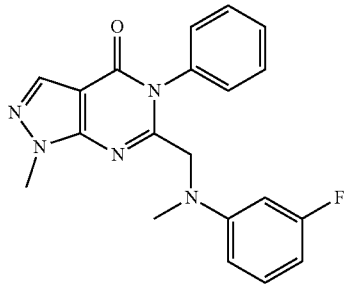 [SMILES: CN(Cc1nc2c(cnn2C)c(=O)n1-c1ccccc1)c1cccc(F)c1]

6-(((3-fluorophenyl)(methyl)amino)methyl)-1-methyl-5-phenyl-1H-pyrazolo[3,4-d]pyrimidin-4(5H)-one A flask containing Potassium Carbonate (24.72 mg, 0.179 mmol), MeI (9.40 μl, 0.150 mmol), 6-(((3-fluorophenyl)amino)methyl)-1-methyl-5-phenyl-1H-pyrazolo[3,4-d]pyrimidin-4(5H)-one (50 mg, 0.143 mmol), and 1 mL DMF was heated to 50° C. and stirred overnight. The next day the mixture was diluted with water and extracted 2× with ethyl acetate. The combined organic portion was washed 3× with brine, dried over sodium sulfate, and concentrated. The crude mixture was purified by flash chromatography (EtOAc in Hex) and the product obtained was further purified by recrystallization from ethanol yielding the titled compound as a white solid (10 mg, 0.028 mmol, 19.23% yield). MS (ESI): m/z 364.16 [M+H]+ 1H NMR (500 MHz, Chloroform-d) δ 8.05 (s, 1H), 7.59 (t, J=7.5 Hz, 2H), 7.53 (t, J=7.4 Hz, 1H), 7.28 (d, J=8.1 Hz, 2H), 7.10 (q, J=7.9 Hz, 1H), 6.41 (t, J=8.3 Hz, 1H), 6.29 (dd, J=16.8, 10.6 Hz, 2H), 4.16 (s, 2H), 3.87 (s, 3H), 2.99 (s, 3H). 13C NMR (126 MHz, Chloroform-d) δ 163.94 (d, J=242.4 Hz), 158.37, 156.25, 150.80, 150.59 (d, J=10.6 Hz), 136.07, 135.24, 130.30, 130.07 (d, J=10.3 Hz), 129.73, 128.15, 107.78 (d, J=2.3 Hz), 104.16, 103.66 (d, J=21.5 Hz), 99.46 (d, J=26.3 Hz), 55.73, 39.56, 33.91.

Preparation 18

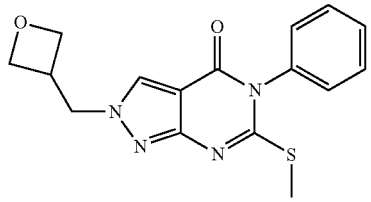 [SMILES: CSc1nc2nn(CC3COC3)cc2c(=O)n1-c1ccccc1]

6-(methylthio)-2-(oxetan-3-ylmethyl)-5-phenyl-2H-pyrazolo[3,4-d]pyrimidin-4(5H)-one To a solution of Potassium Carbonate (594 mg, 4.30 mmol), 6-mercapto-5-phenyl-1H-pyrazolo[3,4-d]pyrimidin-4(5H)-one (500 mg, 2.047 mmol) in 5 mL DMF under nitrogen was added MeI (0.128 ml, 2.047 mmol) by syringe. The mixture was stirred for 2 h at which point oxetan-3-ylmethyl methanesulfonate (340 mg, 2.047 mmol) was added and the mixture was heated to 50° C. overnight. The next day the mixture was diluted with water and extracted 2× with ethyl acetate. The combined organics were washed with brine, dried over sodium sulfate, and concentrated. The product was purified by flash (EtOAc in Hex), The last major peak contained the desired product which was a white solid. (85 mg, 0.259 mmol, 12.65% yield) 1H NMR (500 MHz, Chloroform-d) δ 8.05 (s, 1H), 7.61-7.48 (m, 3H), 7.28 (dd, J=6.3, 2.8 Hz, 2H), 4.87 (t, J=7.1 Hz, 2H), 4.65-4.42 (m, 4H), 3.66 (p, J=7.0 Hz, 1H), 2.51 (s, 3H).

Preparation 19

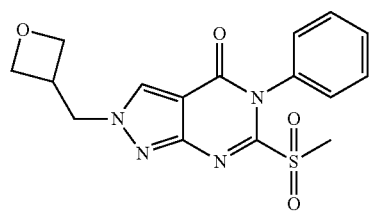 [SMILES: CS(=O)(=O)c1nc2nn(CC3COC3)cc2c(=O)n1-c1ccccc1]

6-(methylsulfonyl)-2-(oxetan-3-ylmethyl)-5-phenyl-2H-pyrazolo[3,4-d]pyrimidin-4(5H)-one 6-(methylthio)-2-(oxetan-3-ylmethyl)-5-phenyl-2H-pyrazolo[3,4-d]pyrimidin-4(5H)-one (85 mg, 0.259 mmol) and mCPBA (191 mg, 0.777 mmol) were dissolved in 2 mL DCM and stirred for 4 hours. 2 mL 10% thiosulfate solution was added and the mixture was stirred vigorously for 30 min. Additional DCM and 10% sodium carbonate solution was added and the organic portion was dried over sodium sulfate. Upon evaporation the titled compound was obtained as a white solid. (67 mg, 0.186 mmol, 71.8% yield)

Sub-Example 63: CCG: 259163

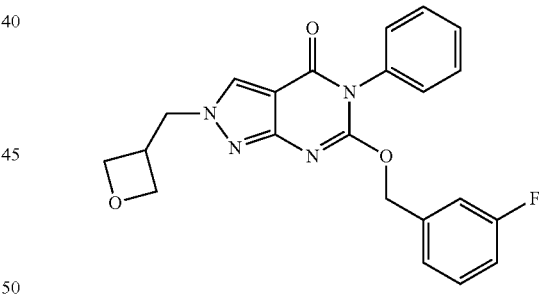

6-((3-fluorobenzyl)-2-(oxetan-3-ylmethyl)-5-phenyl-2H-pyrazolo[3,4-d]pyrimidin-4(5H)-one To a flask at 0° C. charged with 60% NaH in mineral oil (7.65 mg, 0.223 mmol) and 1 mL DMF was added (3-fluorophenyl)methanol (0.026 ml, 0.242 mmol). After stirring for 20 min, 6-(methylsulfonyl)-2-(oxetan-3-ylmethyl)-5-phenyl-2H-pyrazolo[3,4-d]pyrimidin-4(5H)-one (67 mg, 0.186 mmol) in 2 mL DMF was added by syringe. The mixture was allowed to warm gradually to room temperature overnight. The next day the reaction was diluted with water and extracted 2× with ethyl acetate. The combined organic was washed 3× with brine then dried over sodium sulfate. Upon evaporation a yellow oil was obtained to which ethanol was quickly added and crystals began to form immediately. The white crystalline solid was collected by filtration, washed with additional ethanol and then with hexanes, affording the titled compound (33 mg, 0.081 mmol, 43.7% yield). MS (ESI): m/z 407.1515 [M+H]⁺ ¹H NMR (500 MHz, Chloroform-d) δ 8.04 (s, 1H), 7.52 (t, J=7.4 Hz, 2H), 7.48 (d, J=7.1 Hz, 1H), 7.25-7.18 (m, 3H), 6.94 (dt, J=9.2, 4.6 Hz, 1H), 6.90 (d, J=7.8 Hz, 1H), 6.80-6.70 (m, 1H), 5.43 (s, 2H), 4.87 (t, J=7.1 Hz, 2H), 4.59-4.50 (m, 4H), 3.63 (hept, J=7.1 Hz, 1H). 13C NMR (126 MHz, Chloroform-d) δ 162.73 (d, J=246.4 Hz), 159.03, 157.58, 154.77, 137.82 (d, J=7.6 Hz), 134.98, 129.95 (d, J=8.2 Hz), 129.35, 128.92, 128.44, 122.29 (d, J=3.1 Hz), 114.83 (d, J=21.2 Hz), 113.74 (d, J=22.4 Hz), 109.99, 104.09, 74.55, 69.02, 55.73, 35.36.

Sub-Example 64: CCG:262547

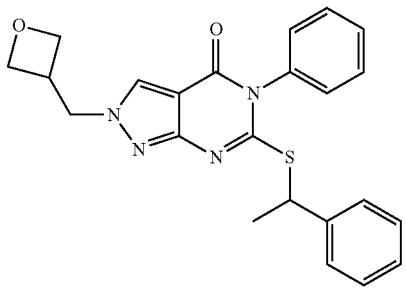 [SMILES: CC(Sc1nc2nn(CC3COC3)cc2c(=O)n1-c1ccccc1)c1ccccc1]

2-(oxetan-3-ylmethyl)-5-phenyl-6-((1-phenylethyl)thio)-2H-pyrazolo[3,4-d]pyrimidin-4(5H)-one 6-mercapto-5-phenyl-1H-pyrazolo[3,4-d]pyrimidin-4(5H)-one (100 mg, 0.409 mmol), Potassium Carbonate (141 mg, 1.023 mmol), and (1-bromoethyl)benzene (55.9 µl, 0.409 mmol) were stirred in 2 mL DMF at room temperature for 1 h. Oxetan-3-ylmethyl methanesulfonate (68.0 mg, 0.409 mmol) was added by syringe and the mixture was heated to 60° C. overnight. The next morning the mixture was diluted with water and extracted 2× with ethyl acetate. The combined organic portions were washed 3× with brine, dried over sodium sulfate, and concentrated. The crude residue was purified by flash (EtOAc in Hex) yielding the titled compound as a colorless oil (26 mg, 0.062 mmol, 15.18% yield). MS (ESI): m/z 419.1537 [M+H]⁺ 1H NMR (500 MHz, Chloroform-d) δ 8.06 (s, 1H), 7.56-7.40 (m, 3H), 7.35 (d, J=7.6 Hz, 2H), 7.31-7.25 (m, 3H), 7.24-7.14 (m, 2H), 5.18 (q, J=7.0 Hz, 1H), 4.87 (t, J=7.2 Hz, 2H), 4.57 (d, J=7.5 Hz, 2H), 4.54 (q, J=5.7 Hz, 2H), 3.66 (h, J=6.9 Hz, 1H), 1.75 (d, J=7.0 Hz, 3H). 13C NMR (126 MHz, Chloroform-d) δ 160.53, 158.69, 158.62, 141.62, 135.57, 129.82, 129.62, 129.59, 129.56, 129.51, 128.62, 128.54, 127.70, 127.48, 105.00, 74.46, 55.80, 46.52, 35.38, 22.10.

Sub-Example 65: CCG: 262548

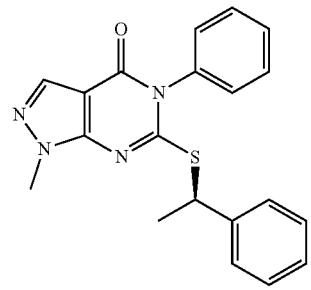 [SMILES: C[C@@H](Sc1nc2c(cnn2C)c(=O)n1-c1ccccc1)c1ccccc1]

(R)-1-methyl-5-phenyl-6-((1-phenylethyl)thio)-1H-pyrazolo[3,4-d]pyrimidin-4(5H)-one To a flask at 0° C. charged with Triphenylphosphine (76 mg, 0.290 mmol), 6-mercapto-1-methyl-5-phenyl-1H-pyrazolo[3,4-d]pyrimidin-4(5H)-one (50 mg, 0.194 mmol), and (S)-1-phenylethanol (34.8 µl, 0.290 mmol) suspended in 2 mL THF was added DIAD (56.5 µl, 0.290 mmol) dropwise by syringe. The mixture was allowed to return to RT and stirred for 1.5 h at which point a homogenous solution was obtained. The solvent was removed and the residue was purified by flash (EtOAc in Hex) with the product eluting around 45% EtOAc. The compound was enantioenriched further by dissolving this sample in 15 mL hot ethanol, allowing it to cool to RT then storing at −20° C. for several days and collecting the resulting crystals. White solid (12 mg, 0.033 mmol, 17.10% yield) >95% EE as determined by Chiral HPLC (15% IPA in Hexanes on chiralcel OD column). NMR and MS data were verified to be identical to the racemate.

Sub-Example 66: CCG: 262703

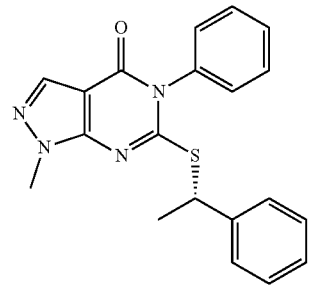 [SMILES: C[C@H](Sc1nc2c(cnn2C)c(=O)n1-c1ccccc1)c1ccccc1]

(S)-1-methyl-5-phenyl-6-((1-phenylethyl)thio)-1H-pyrazolo[3,4-d]pyrimidin-4(5H)-one To a dry scintillation vial was added Polystyrene bound triphenylphosphine (3 mmol/g, 1.5 eq) and 6-mercapto-1-methyl-5-phenyl-1H-pyrazolo[3,4-d]pyrimidin-4(5H)-one (85 mg, 0.329 mmol) and 2 mL THF under a stream of nitrogen. (R)-1-phenylethanol (0.069 mL, 0.576 mmol) and DIAD (0.112 mL, 0.576 mmol) were added sequentially by syringe. The vial was sealed under nitrogen and placed on an orbit shaker overnight. The next day the mixture was filtered through celite and the solvent removed. The crude residue was purified by flash (EtOAc/Hexanes) then was recrystallized from hot ethanol and was finally purified by Prep TLC (20% Acetone in Chloroform) yielding the titled compound as a white solid (7 mg, 0.019 mmol, 5.87% yield). 91% EE by Chiral HPLC (15% IPA in Hexanes on chiralcel OD column). NMR and MS data were verified to be identical to the racemate.

Sub-Example 67: CCG: 262561

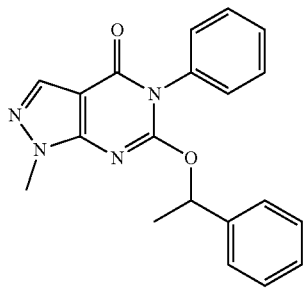 [SMILES: CC(Oc1nc2c(cnn2C)c(=O)n1-c1ccccc1)c1ccccc1]

1-methyl-5-phenyl-6-(1-phenylethoxy)-1H-pyrazolo[3,4-d]pyrimidin-4(5H)-one

60% NaH in mineral oil (7.89 mg, 0.197 mmol) was added to a solution of 1-phenylethanol (0.026 ml, 0.214 mmol) in DMF at 0° C. The mixture was stirred for 10 minutes at which point 1-methyl-6-(methylsulfonyl)-5-phenyl-1H-pyrazolo[3,4-d]pyrimidin-4(5H)-one (50 mg, 0.164 mmol) was added and the mixture was allowed to warm to room temperature and stirred overnight. The mixture was diluted with water and extracted 2× with ethyl acetate. The combined organics were washed 3× with brine, dried over sodium sulfate, and concentrated. The crude residue was purified by flash (EtOAc and Hexanes) yielding the titled compound as a white solid (5 mg, 0.014 mmol, 8.79% yield). MS (ESI): m/z 347.1504 [M+H]+ 1H NMR (500 MHz, Chloroform-d) δ 7.97 (s, 1H), 7.60-7.44 (m, 3H), 7.28 (dd, J=10.4, 7.1 Hz, 4H), 7.14 (d, J=7.0 Hz, 3H), 6.20 (q, J=6.6 Hz, 1H), 3.90 (s, 3H), 1.50 (d, J=6.6 Hz, 3H). 13C NMR (126 MHz, Chloroform-d) δ 158.07, 154.93, 151.02, 141.03, 135.55, 135.21, 129.23, 128.72, 128.48, 128.44, 128.39, 128.02, 125.70, 109.99, 101.91, 33.77, 22.59.

Sub-Example 68: CCG:262701

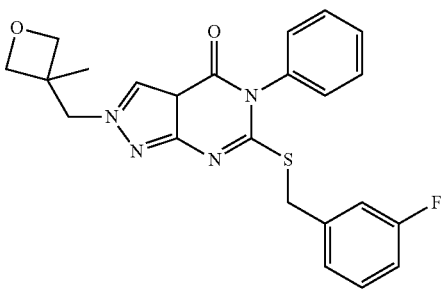

6-((3-fluorobenzyl)thio)-2-((3-methyloxetan-3-yl)methyl)-5-phenyl-2H-pyrazolo[3,4-d]pyrimidin-4(5H)-one General Procedure A White solid (30 mg, 0.069 mmol, 24.22% yield) MS (ESI): m/z 437.1444 [M+H]+ 1H NMR (500 MHz, Chloroform-d) δ 8.05 (s, 1H), 7.55-7.46 (m, 3H), 7.31-7.25 (m, 2H), 7.22 (q, J=7.5 Hz, 1H), 7.10 (d, J=7.7 Hz, 1H), 7.05 (d, J=9.6 Hz, 1H), 6.91 (t, J=8.3 Hz, 1H), 4.78 (d, J=6.3 Hz, 2H), 4.47 (s, 2H), 4.45 (d, J=6.4 Hz, 2H), 4.39 (s, 2H), 1.29 (s, 3H). 13C NMR (126 MHz, Chloroform-d) δ 162.68 (d, J=246.5 Hz), 160.34, 158.62, 158.34, 138.20 (d, J=7.6 Hz), 135.49, 130.03, 130.01 (d, J=8.0 Hz), 129.65, 129.57, 129.50, 125.06 (d, J=2.9 Hz), 116.31 (d, J=21.8 Hz), 114.52 (d, J=21.0 Hz), 104.86, 80.24, 60.07, 40.49, 37.18, 21.52.

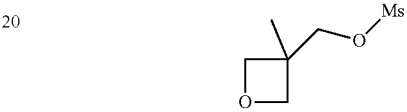

(3-methyloxetan-3-yl)methyl methanesulfonate

Prepared Similarly to Oxetan-3-Ylmethyl Methanesulfonate (Preparation 3)

Yellow solid (650 mg, 3.61 mmol, 73.7% yield).

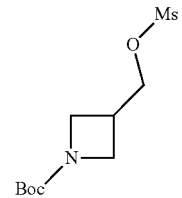

tert-butyl 3-(((methylsulfonyl)oxy)methyl)azetidine-1-carboxylate

Prepared Similarly to Oxetan-3-Ylmethyl Methanesulfonate (Preparation 3)

Orange oil (0.9 g, 3.39 mmol, 94% yield).

Preparation 20

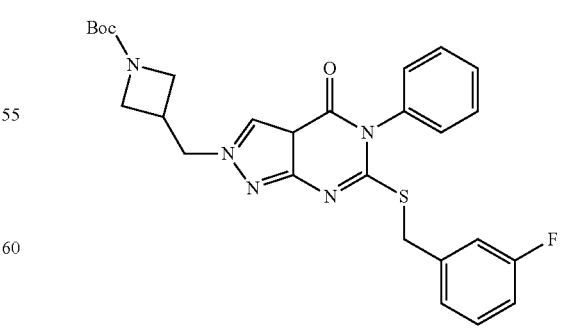

tert-butyl 3-((6-((3-fluorobenzyl)thio)-4-oxo-5-phenyl-4,5-dihydro-2H-pyrazolo[3,4-d]pyrimidin-2-yl)methyl)azetidine-1-carboxylate General Procedure A White solid (230 mg, 0.441 mmol, 15.54% yield). 1H NMR (400 MHz, Chloroform-d) δ 8.06 (s, 1H), 7.59-7.46 (m, 3H), 7.25-7.17 (m, 3H), 7.11 (d, J=7.6 Hz, 1H), 7.06 (d, J=9.6 Hz, 1H), 6.93 (dt, J=9.8, 4.9 Hz, 1H), 4.47 (d, J=7.6 Hz, 2H), 4.39 (s, 2H), 4.08 (t, J=8.5 Hz, 2H), 3.77 (dd, J=8.9, 5.0 Hz, 2H), 3.23 (q, J=8.0, 6.8 Hz, 1H), 1.45 (s, 9H).

Sub-Example 69: CCG: 262702

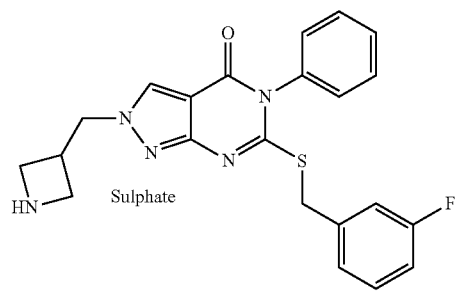 [SMILES: O=c1c2cn(CC3CNC3)nc2nc(SCc2cccc(F)c2)n1-c1ccccc1]

3-((6-((3-fluorobenzyl)thio)-4-oxo-5-phenyl-4,5-dihydro-2H-pyrazolo[3,4-d]pyrimidin-2-yl)methyl)azetidin-1-ium sulfate Tert-butyl 3-((6-((3-fluorobenzyl)thio)-4-oxo-5-phenyl-4,5-dihydro-2H-pyrazolo[3,4-d]pyrimidin-2-yl)methyl)azetidine-1-carboxylate (230 mg, 0.441 mmol), 5 mL toluene and 0.5 mL concentrated sulfuric acid was stirred for 1 hour at RT. The toluene layer was discarded and the sulfuric acid layer was washed with 10 mL Diethyl ether before being dissolved in 5 mL hot methanol. The product crystallized out upon cooling. The product was further washed with cold methanol to remove residual sulfuric acid yielding the titled compound as a white solid (50 mg, 0.118 mmol, 26.8% yield). MS (ESI): m/z 422.1445 [M+H]$^+$ $^1$H NMR (500 MHz, DMSO-d$_6$) δ 9.11 (s, 3H), 8.68 (s, 1H), 7.52 (d, J=5.3 Hz, 3H), 7.41-7.34 (m, 2H), 7.34-7.29 (m, 1H), 7.23 (t, J=9.2 Hz, 2H), 7.07 (t, J=8.7 Hz, 1H), 4.61 (d, J=7.2 Hz, 2H), 4.35 (s, 2H), 4.03 (t, J=9.6 Hz, 2H), 3.91 (t, J=8.6 Hz, 2H), 3.33 (dq, J=15.3, 7.6 Hz, 1H). 13C NMR (126 MHz, DMSO-d6) δ 162.38 (d, J=244.0 Hz), 159.53, 158.25, 157.93, 139.95 (d, J=7.9 Hz), 136.15, 130.96, 130.81 (d, J=8.6 Hz), 130.28, 130.24, 129.85, 125.71, 116.35 (d, J=21.9 Hz), 114.60 (d, J=21.1 Hz), 104.54, 54.06, 48.89, 35.98, 32.39.

Preparation 21:

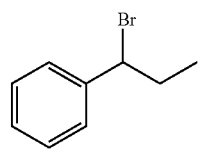

(1-bromopropyl)benzene

PBr3 (0.346 ml, 3.67 mmol) was added dropwise to a solution of 1-phenylpropan-1-ol (1 g, 7.34 mmol) in 10 ml DCM at 0° C. The mixture was warmed to RT and stirred for 24 hr. The next day 10 mL 10% Aq. sodium carbonate was added and the mixture was vigorously stirred for 10 min. The organic portion was further washed with brine before drying over sodium sulfate and concentrating under vacuum yielding the titled compound as a yellow oil (1.1 g, 5.53 mmol, 75% yield)

Sub-Example 70: CCG:262704

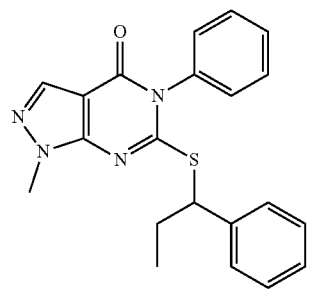 [SMILES: CCC(Sc1nc2c(cnn2C)c(=O)n1-c1ccccc1)c1ccccc1]

1-methyl-5-phenyl-6-((1-phenylpropyl)thio)-1H-pyrazolo[3,4-d]pyrimidin-4(5H)-one Prepared in a Similar Manner to Sub-Example 38

White solid. (110 mg, 0.292 mmol, 75% yield) MS (ESI): m/z 377.1321 [M+H]$^+$ 1H NMR (500 MHz, Chloroform-d) δ 7.99 (s, 1H), 7.58-7.46 (m, 3H), 7.37-7.32 (m, 2H), 7.30 (t, J=7.7 Hz, 2H), 7.28-7.22 (m, 2H), 7.17 (d, J=7.2 Hz, 1H), 4.77 (dd, J=9.1, 6.1 Hz, 1H), 4.00 (s, 3H), 2.16-2.02 (m, 1H), 1.97-1.83 (m, 1H), 0.92 (t, J=7.3 Hz, 3H). 13C NMR (126 MHz, Chloroform-d) δ 161.60, 157.83, 151.02, 140.91, 135.72, 135.34, 129.90, 129.70, 129.63, 129.42, 129.36, 128.40, 128.08, 127.46, 102.86, 53.65, 34.03, 29.25, 12.29.

Preparation 22:

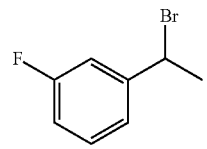

1-(1-bromoethyl)-3-fluorobenzene

PBr3 (0.084 ml, 0.892 mmol) was added to a solution of 1-(3-fluorophenyl)ethanol (0.25 g, 1.784 mmol) in 3 mL DCM at 0° C. and the mixture was stirred for a day at RT. The mixture was diluted with DCM and washed with saturated sodium bicarbonate and brine before drying over sodium sulfate and concentrating to yield the titled compound as a yellow oil (240 mg, 1.182 mmol, 66.3% yield).

Sub-Example 71: CCG:262741

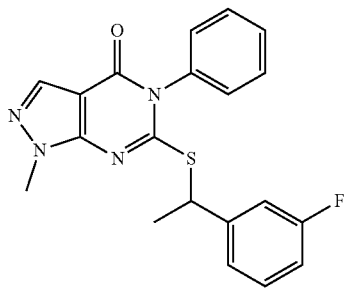 [SMILES: CC(Sc1nc2c(cnn2C)c(=O)n1-c1ccccc1)c1cccc(F)c1]

6-((1-(3-fluorophenyl)ethyl)thio)-1-methyl-5-phenyl-1H-pyrazolo[3,4-d]pyrimidin-4(5H)-one Prepared in a Similar Manner to Sub-Example 38

White solid. (106 mg, 0.279 mmol, 67.9% yield). MS (ESI): m/z 381.1182 [M+H]$^+$ 1H NMR (500 MHz, Chloroform-d) δ 7.99 (s, 1H), 7.60-7.45 (m, 3H), 7.32-7.23 (m, 2H), 7.19 (dd, J=4.8, 2.2 Hz, 1H), 7.17 (d, J=8.3 Hz, 1H), 7.10 (dt, J=10.0, 2.1 Hz, 1H), 6.93 (td, J=8.4, 2.5 Hz, 1H), 4.99 (q, J=7.2 Hz, 1H), 3.98 (s, 3H), 1.67 (d, J=7.0 Hz, 3H). 13C NMR (126 MHz, Chloroform-d) δ 162.69 (d, J=246.1 Hz), 161.07, 157.70, 150.94, 144.96 (d, J=7.4 Hz), 135.45 (d, J=23.9 Hz), 135.38, 130.02, 129.96, 129.73 (d, J=9.7 Hz), 129.37 (d, J=2.6 Hz), 123.07 (d, J=2.9 Hz), 114.59 (d, J=19.2 Hz), 114.42 (d, J=18.5 Hz), 102.92, 46.26, 34.10, 21.78.

Sub-Example 72: CCG:262901

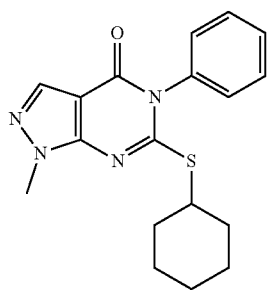 [SMILES: Cn1ncc2c(=O)n(-c3ccccc3)c(SC3CCCCC3)nc21]

6-(cyclohexylthio)-1-methyl-5-phenyl-1H-pyrazolo[3,4-d]pyrimidin-4(5H)-one

Prepared in a Similar Manner to Sub-Example 38

White solid (42 mg, 0.123 mmol, 45.5% yield) MS (ESI): m/z 341.1432 [M+H]$^+$ 1H NMR (500 MHz, Chloroform-d) δ 8.02 (s, 1H), 7.56-7.47 (m, 3H), 7.29-7.20 (m, 2H), 3.97 (s, 3H), 3.88-3.76 (m, 1H), 2.18-2.01 (m, 2H), 1.83-1.70 (m, 2H), 1.69-1.60 (m, 1H), 1.53-1.35 (m, 4H), 1.33-1.25 (m, 1H). 13C NMR (126 MHz, Chloroform-d) δ 162.12, 157.98, 151.16, 135.93, 135.37, 129.80, 129.61, 129.39, 102.76, 46.42, 33.78, 32.51, 26.12, 25.59.

Sub-Example 73: CCG: 263051

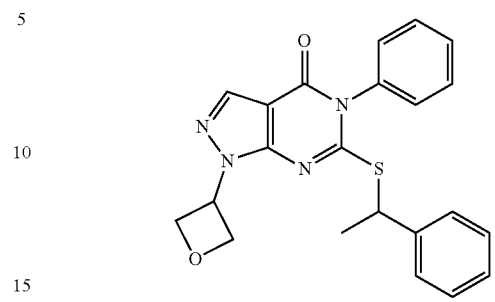

1-(oxetan-3-yl)-5-phenyl-6-((1-phenylethyl)thio)-1H-pyrazolo[3,4-d]pyrimidin-4(5H)-one Prepared in a Manner Similar to Example 18

White Solid (57 mg, 0.141 mmol, 34.4% yield) MS (ESI): m/z 405.1383 [M+H]$^+$ 1H NMR (500 MHz, Chloroform-d) δ 8.10 (s, 1H), 7.57-7.47 (m, 3H), 7.39 (d, J=7.6 Hz, 2H), 7.32 (t, J=7.5 Hz, 2H), 7.28-7.22 (m, 2H), 7.18 (d, J=6.8 Hz, 1H), 5.93 (p, J=7.4 Hz, 1H), 5.34 (t, J=6.6 Hz, 1H), 5.27 (t, J=6.5 Hz, 1H), 5.09 (t, J=7.2 Hz, 1H), 5.03 (t, J=7.2 Hz, 1H), 4.98 (q, J=7.2 Hz, 1H), 1.70 (d, J=7.2 Hz, 3H). 13C NMR (126 MHz, Chloroform-d) δ 162.19, 157.62, 151.07, 141.96, 136.28, 135.47, 130.06, 129.80, 129.73, 129.28, 128.59, 127.62, 127.35, 103.41, 76.99, 76.81, 50.70, 47.04, 22.14.

Sub-Example 74: CCG: 263052

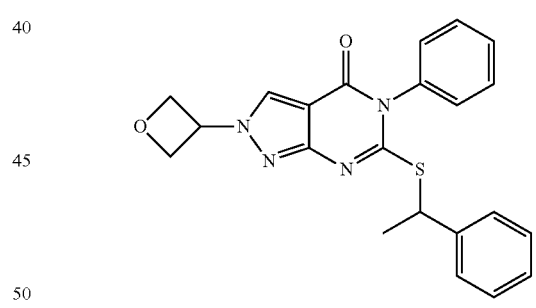

2-(oxetan-3-yl)-5-phenyl-6-((1-phenylethyl)thio)-2H-pyrazolo[3,4-d]pyrimidin-4(5H)-one Prepared in a Manner Similar to Example 19

White Solid (14 mg, 0.035 mmol, 8.45% yield) MS (ESI): m/z 405.1381 [M+H]$^+$ $^1$H NMR (500 MHz, Chloroform-d) δ 8.19 (s, 1H), 7.55-7.42 (m, 3H), 7.36 (d, J=7.6 Hz, 2H), 7.31-7.26 (m, 3H), 7.25-7.16 (m, 2H), 5.57 (p, J=6.9 Hz, 1H), 5.26-5.18 (m, 3H), 5.09 (t, J=7.3 Hz, 2H), 1.77 (d, J=6.9 Hz, 3H). 13C NMR (126 MHz, Chloroform-d) δ 160.97, 158.63, 141.50, 135.49, 129.87, 129.61, 129.54, 129.53, 128.57, 127.96, 127.70, 127.52, 105.33, 76.86, 76.82, 56.78, 46.58, 22.15.

Sub-Example 75: CCG:263055

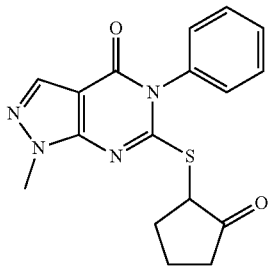

1-methyl-6-((2-oxocyclopentyl)thio)-5-phenyl-1H-pyrazolo[3,4-d]pyrimidin-4(5H)-one Prepared in a Similar Manner to Sub-Example 38

Off white solid (37 mg, 0.109 mmol, 56.2% yield) MS (ESI): m/z 341.1068 [M+H]$^+$ 1H NMR (500 MHz, Chloroform-d) δ 8.02 (s, 1H), 7.57-7.50 (m, 3H), 7.35-7.26 (m, 2H), 4.15 (t, J=9.5 Hz, 1H), 3.95 (s, 3H), 2.68-2.56 (m, 1H), 2.47 (dd, J=18.9, 8.7 Hz, 1H), 2.34 (dt, J=18.9, 9.4 Hz, 1H), 2.24-2.08 (m, 2H), 1.98 (p, J=9.7, 9.2 Hz, 1H). 13C NMR (126 MHz, Chloroform-d) δ 212.37, 160.45, 157.59, 150.69, 135.49, 130.19, 129.85, 129.72, 129.48, 129.34, 103.11, 51.85, 37.02, 34.21, 30.08, 20.75.

Sub-Example 76: CCG: 263056

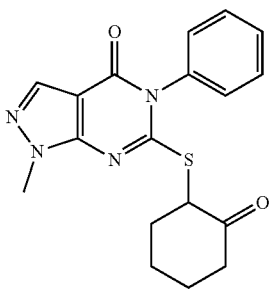 [SMILES: Cn1ncc2c(=O)n(-c3ccccc3)c(SC3CCCCC3=O)nc21]

1-methyl-6-((2-oxocyclohexyl)thio)-5-phenyl-1H-pyrazolo[3,4-d]pyrimidin-4(5H)-one Prepared in a Similar Manner to Sub-Example 38

White Solid (34 mg, 0.096 mmol, 49.6% yield) MS (ESI): m/z 355.1223 [M+H]$^+$ 1H NMR (500 MHz, Chloroform-d) δ 7.98 (s, 1H), 7.56-7.48 (m, 3H), 7.35-7.30 (m, 1H), 7.23 (dt, J=5.8, 2.8 Hz, 1H), 4.61 (dd, J=11.5, 5.3 Hz, 1H), 3.91 (s, 3H), 2.61 (dt, J=13.4, 4.5 Hz, 1H), 2.53-2.42 (m, 2H), 2.11 (ddt, J=12.8, 6.3, 2.9 Hz, 1H), 1.95 (dt, J=12.4, 3.8 Hz, 1H), 1.89-1.67 (m, 3H). 13C NMR (126 MHz, Chloroform-d) δ 204.81, 160.89, 157.67, 150.76, 135.60, 135.34, 130.10, 129.90, 129.68, 129.47, 129.24, 102.89, 56.78, 41.66, 33.99, 33.86, 27.70, 25.36.

Sub-Example 77: CCG:263057

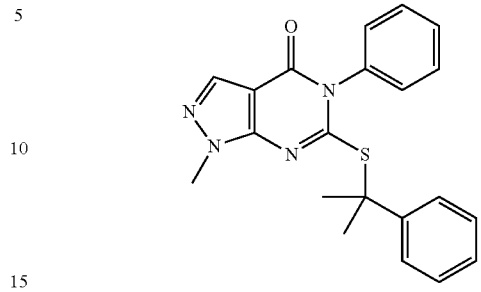

1-methyl-5-phenyl-6-((2-phenylpropan-2-yl)thio)-1H-pyrazolo[3,4-d]pyrimidin-4(5H)-one To a slurry of 6-mercapto-1-methyl-5-phenyl-1H-pyrazolo[3,4-d]pyrimidin-4(5H)-one (75 mg, 0.290 mmol) and prop-1-en-2-ylbenzene (0.038 ml, 0.290 mmol) in DCM at 0° C. was added TFA (0.224 ml, 2.90 mmol) dropwise. The resulting homogenous solution was stirred for 30 min at 0° C. and 30 min at RT. The reaction was diluted with DCM and washed with saturated bicarb. The organic portion was dried over sodium sulfate and concentrated. The crude product was purified by flash (eluting around 40-50% EtOAc in Hex) yielding a white solid. (65 mg, 0.173 mmol, 59.5% yield) MS (ESI): m/z 377.1434 [M+H]$^+$ 1H NMR (500 MHz, Chloroform-d) δ 7.91 (s, 1H), 7.62-7.50 (m, 5H), 7.31 (t, J=7.6 Hz, 2H), 7.25-7.14 (m, 3H), 3.71 (s, 3H), 1.89 (s, 6H). 13C NMR (126 MHz, Chloroform-d) δ 160.48, 157.80, 150.72, 145.95, 135.76, 135.19, 129.82, 129.65, 129.43, 127.91, 126.59, 126.28, 102.90, 54.87, 33.99, 29.71.

Preparation 23:

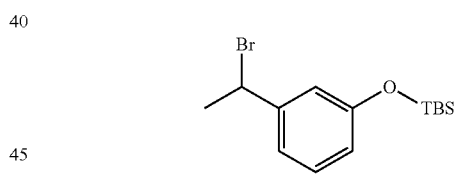

(3-(1-bromoethyl)phenoxy)(tert-butyl)dimethylsilane 3-ethylphenol (1 g, 8.19 mmol), TBS-Cl (1.357 g, 9.00 mmol), and Imidazole (1.226 g, 18.01 mmol) were stirred overnight in 10 mL DMF. Diluted with 25 mL water and extracted with 25 mL Ethyl acetate. The organic portion was dried over sodium sulfate and the solvent was removed.

The crude oil was filtered through a pad of silica using ~5% EtOAc in Hexanes yielding tert-butyl(3-ethylphenoxy)dimethylsilane compound as a colorless oil (1.8 g, 7.61 mmol, 93% yield).

A suspension of tert-butyl(3-ethylphenoxy)dimethylsilane (1.8 g, 7.61 mmol), Benzoyl Peroxide (0.277 g, 1.142 mmol), and NBS (1.355 g, 7.61 mmol) in 15 mL carbon tetrachloride was refluxed for 3 hours. The mixture was cooled, filtered and the filtrated was diluted with DCM and washed with water and brine before drying over sodium sulfate. The mixture was concentrated and the resulting Sub-Example 78: CCG:263117

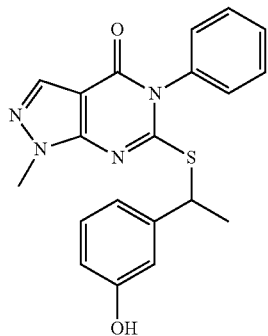 [SMILES: CC(Sc1nc2c(cnn2C)c(=O)n1-c1ccccc1)c1cccc(O)c1]

6-((1-(3-hydroxyphenyl)ethyl)thio)-1-methyl-5-phenyl-1H-pyrazolo[3,4-d]pyrimidin-4(5H)-one 6-mercapto-1-methyl-5-phenyl-1H-pyrazolo[3,4-d]pyrimidin-4(5H)-one (125 mg, 0.484 mmol), (3-(1-bromoethyl)phenoxy)(tert-butyl)dimethylsilane (214 mg, 0.678 mmol), and K2CO3 (100 mg, 0.726 mmol) in 5 mL DMF was stirred overnight. The next day the mixture was diluted with 15 mL water and extracted 2× with Ethyl acetate. The combined organics were washed 3× with brine, dried over sodium sulfate and concentrated. The crude oil was purified by flash with the product eluting around 30% EtOAc in Hex yielding 6-((1-(3-((tert-butyldimethylsilyl)oxy)phenyl)ethyl)thio)-1-methyl-5-phenyl-1H-pyrazolo[3,4-d]pyrimidin-4(5H)-one (195 mg, 0.396 mmol, 82% yield) as a yellow oil.

To an HDPE vial was added 6-((1-(3-((tert-butyldimethylsilyl)oxy)phenyl)ethyl)thio)-1-methyl-5-phenyl-1H-pyrazolo[3,4-d]pyrimidin-4(5H)-one (195 mg, 0.396 mmol) dissolved in 3 mL THF. HF (250 µl, 10.15 mmol) 70% in pyridine was added and the vial was sealed under nitrogen and left overnight. The next morning the reaction was diluted with 15 mL water and extracted with EtOAc. The organic portion was washed with saturated aqueous sodium bicarbonate and brine then dried over sodium sulfate and concentrated yielding the titled compound as a white solid (123 mg, 0.325 mmol, 82% yield). MS (ESI): m/z 379.1218 [M+H]+ 1H NMR (500 MHz, DMSO-d6) δ 9.43 (s, 1H), 8.04 (s, 1H), 7.59-7.53 (m, 1H), 7.53-7.48 (m, 2H), 7.38 (d, J=7.6 Hz, 1H), 7.33-7.26 (m, 1H), 7.10 (t, J=7.8 Hz, 1H), 6.83 (d, J=7.7 Hz, 1H), 6.78 (s, 1H), 6.63 (dd, J=8.1, 2.4 Hz, 1H), 4.94 (q, J=7.0 Hz, 1H), 3.97 (s, 3H), 1.64 (d, J=7.0 Hz, 3H). 13C NMR (126 MHz, DMSO-d6) δ 161.31, 157.80, 157.30, 150.87, 143.59, 136.14, 135.10, 130.26, 130.07, 129.98, 129.95, 118.52, 114.93, 114.74, 102.80, 46.84, 34.34, 22.09.

Preparation 24

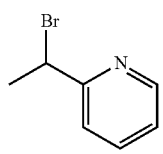

2-(1-bromoethyl)pyridine 2-ethylpyridine (1.067 ml, 9.33 mmol), AIBN (0.153 g, 0.933 mmol), and NBS (1.744 g, 9.80 mmol) were refluxed in 20 mL of Carbon tetrachloride for 1 hour. The reaction was cooled and filtered and the solid was washed with DCM. The filtrate was washed with saturated aqueous sodium bicarbonate and brine before drying over sodium sulfate and concentrating. The resulting 2.1 g of orange oil was carried forward without further purification.

Sub-Example 79: CCG:263118

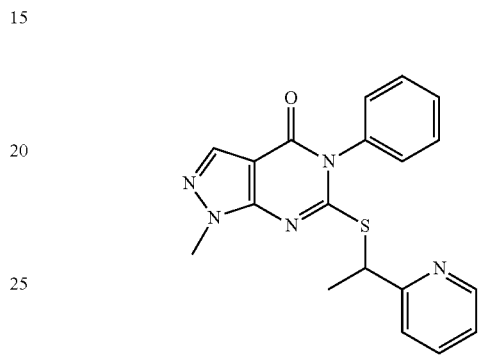

1-methyl-5-phenyl-6-((1-(pyridin-2-yl)ethyl)thio)-1H-pyrazolo[3,4-d]pyrimidin-4(5H)-one Prepared in a Similar Manner to Sub-Example 38

White solid (56 mg, 0.154 mmol, 39.8% yield) MS (ESI): m/z 364.1225 [M+H]+ 1H NMR (500 MHz, Chloroform-d) δ 8.55 (d, J=4.8 Hz, 1H), 8.00 (s, 1H), 7.64 (t, J=7.7 Hz, 1H), 7.57-7.45 (m, 3H), 7.40 (d, J=7.8 Hz, 1H), 7.28 (d, J=7.5 Hz, 1H), 7.22 (d, J=6.5 Hz, 1H), 7.16 (t, J=6.2 Hz, 1H), 5.14 (q, J=7.2 Hz, 1H), 3.96 (s, 3H), 1.73 (d, J=7.1 Hz, 3H). 13C NMR (126 MHz, Chloroform-d) δ 161.52, 161.07, 157.78, 150.96, 149.52, 136.66, 135.53, 135.37, 129.96, 129.75, 129.38, 122.34, 121.76, 102.83, 48.47, 34.00, 20.95.

Preparation 25

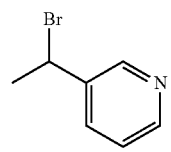

3-(1-bromoethyl)pyridine 3-ethylpyridine (1.067 ml, 9.33 mmol), AIBN (0.153 g, 0.933 mmol), and NBS (1.744 g, 9.80 mmol) were refluxed in 20 mL of Carbon tetrachloride for 1 hour. The reaction was cooled and filtered and the solid was washed with DCM. The filtrate was washed with saturated aqueous sodium bicarbonate and brine before drying over sodium sulfate and concentrating. The resulting 2.2 g of orange oil was carried forward without further purification.

Sub-Example 80: CCG:263119

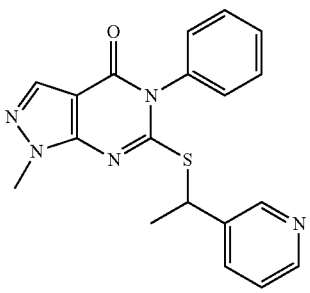 [SMILES: CC(Sc1nc2c(cnn2C)c(=O)n1-c1ccccc1)c1cccnc1]

1-methyl-5-phenyl-6-((1-(pyridin-3-yl)ethyl)thio)-
1H-pyrazolo[3,4-d]pyrimidin-4(5H)-one Prepared in a Similar Manner to Sub-Example 38

White solid (90 mg, 0.248 mmol, 64.0% yield) MS (ESI): m/z 364.1225 [M+H]$^+$ $^1$H NMR (500 MHz, Chloroform-d) δ 8.72 (d, J=2.2 Hz, 1H), 8.49 (d, J=4.8 Hz, 1H), 7.99 (s, 1H), 7.70 (d, J=7.9 Hz, 1H), 7.59-7.47 (m, 3H), 7.29-7.21 (m, 2H), 7.18 (d, J=7.1 Hz, 1H), 5.01 (q, J=7.3 Hz, 1H), 3.99 (s, 3H), 1.68 (d, J=7.3 Hz, 3H). $^{13}$C NMR (126 MHz, Chloroform-d) δ 160.67, 157.61, 150.85, 149.37, 148.81, 138.32, 135.47, 135.37, 134.47, 130.10, 129.79, 129.72, 129.37, 129.35, 123.49, 102.96, 44.04, 34.20, 21.59.

Example II

This example describes the compound inhibition and IC$_{50}$ determination for the thiopyrimidinone compounds of the present invention.

Compound Inhibition and IC$_{50}$ Determination:

Inhibition of ALDH isoenzymes by the compounds and respective IC$_{50}$ curves were determined by measuring the formation of NAD(P)H spectrophotometrically at 340 nm (molar extinction coefficient of 6220 M$^{-1}$ cm$^{-1}$) on a Beckman DU-640 spectrophotometer or a Spectromax 340PC using purified recombinant enzyme. All assays were performed at 25° C. and were initiated by addition of the substrate after a 2 min incubation period with non-saturating levels of coenzyme and aldehyde substrate that was optimized for each set of enzymes. For the ALDH1A family members and ALDH2, the assay included 100-200 nM enzyme, 200 μM NAD$^+$, 100 μM propionaldehyde, and 1% DMSO in 25 mM BES buffer, pH 7.5. The assay for ALDH1B1 used 500 μM NAD$^+$ and 200 μM propionaldehyde. For ALDH4A1 the assay included 500 μM NAD$^+$ and 20 mM propionaldehyde. For ALDH5A1 the assay included 200 μM NAD$^+$ and 2 mM propionaldehyde respectively. For ALDH1L1 the assay included 500 μM NADP$^+$ and 4 mM propionaldehyde. For ALDH3A1, the assay included the commonly utilized substrate benzaldehyde at 300 μM alongside 200 μM NAD$^+$, 20 nM ALDH3A1 and 1% DMSO. Assays for ALDH3A1, ALDH4A1, and ALDH5A1 were performed in 100 mM sodium phosphate buffer, pH 7.5. Data were fit to the four parameter EC$_{50}$ equation using SigmaPlot (v12) and the values represent the average of three independent experiments.

Selection and Characterization of Analogs of Initial Inhibitors

Compounds were initially tested for their effect on the oxidation of aldehyde substrate by ALDH1A1, ALDH2, and ALDH3A1. Compounds which showed potential selectivity for ALDH1A1 were examined further by measuring EC$_{50}$ values for each of the three enzymes. EC$_{50}$ curves for ALDH1A2, ALDH1A3, and ALDH1B1 inhibition were determined for compounds which continued to show selectivity towards ALDH2 or ALDH1A1. Data were fit to the four parameter EC$_{50}$ equation using SigmaPlot (v12) and the values represent the average of three independent experiments.

Steady-State Kinetic Characterization with ALDH1A1

The mode of inhibition towards coenzyme (NAD$^+$) binding was determined via steady-state kinetics by varying inhibitor and coenzyme concentrations at fixed substrate concentrations. Dehydrogenase activity was measured spectrophotometrically by measuring the formation of NADH at 340 nm (molar extinction coefficient of 6220 M$^{-1}$ cm$^{-1}$) on a Beckman DU-640 spectrophotmer. All assays included 100-200 nM enzyme, 100 μM propionaldehyde, and 1% DMSO in 25 mM BES buffer, pH 7.5 at 25° C. For ALDH1A1 ranges of 20-200 μM NAD$^+$ and the appropriate inhibitor concentrations. All data were fit to the tight binding or single substrate-single inhibitor non-linear velocity expressions for competitive, non-competitive, mixed type non-competitive, and uncompetitive inhibition using SigmaPlot (v12, Enzyme Kinetics Module) to evaluate goodness of fit. Lineweaver-Burk plots were generated using SigmaPlot to better visualize the inhibition patterns. All data represent the average of three independent experiments (each n=3).

Crystallization of ALDH1A1 in Complex with Compounds

Crystals of ALDH1A1 were grown by equilibrating 3 mg/mL ALDH1A1 with 100 mM Na-BisTris, pH 6.2-6.6, 9-11% PEG3350, 200 mM NaCl, and 5 mM YbCl$_3$ at 25° C. Inhibitor complexes were prepared by growing crystals in the presence of 200 μM compound (co-crystals or by soaking ALDH1A1 crystals overnight with crystallization solution containing 500 μM inhibitor in 2% (v/v) DMSO. Crystals were cryoprotected for flash-freezing with 20% (v/v) ethylene glycol for ALDH1A1. Diffraction data was collected at Beamline 19-ID operated by the Structural Biology Consortium at the Advanced Proton Source (APS), Argonne National Laboratory. Diffraction data was indexed, integrated, and scaled using HKL2000 and HKL3000. CCP4 was used for molecular replacement and refinement with the human apo-ALDH1A structure (PDB code 4WJ9) for ALDH1A1. Coot was used for model building.

Tables 2 and 3 present the IC$_{50}$ values for the thiopyrimidinone compounds of the present invention.

TABLE 2

| | | IC50 (μM) or % Control at 20 μM | | | | OVSAHO Cell Viability (50 μM) | |
|---|---|---|---|---|---|---|---|
| | | | | | | Total Cell | % CD133 + |
| Example | CCG | ALDH1A1 | ALDH1A2 | ALDH1A3 | ALDH2 | % ctrl | % ctrl |
| 1 | 232820 | 0.500 | 4.7 | >20 | 85% | | |
| 2 | 257901 | 0.520 | 0.680 | 0.360 | 94% | 39 | 58 |
| 3 | 257128 | 0.550 | >20 | 2.8 | 94% | | |
| 4 | 257432 | 0.700 | 5.5 | 1.8 | 87% | | |
| 5 | 257433 | 0.350 | 15 | >10 | 93% | | |
| 6 | 257434 | 0.400 | 5.2 | 7.5 | 91% | | |
| 7 | 257724 | 0.18 | >10 | >10 | N.I. | 14 | 5 |
| 8 | 257725 | 0.085 | >10 | 1.7 | N.I. | 18 | 27 |
| 9 | 257911 | 0.320 | 31% | 60% | 96% | 22 | 50 |
| 10 | 257913 | 0.570 | 38% | 40% | 101% | 9 | 31 |
| 11 | 257910 | 0.430 | 45% | 58% | 97% | 30 | 69 |
| 12 | 257912 | 0.250 | 3.8 | 2.2 | 98% | 50 | 69 |
| 13 | 257902 | 0.250 | 0.344 | 0.130 | 94% | 69 | 83 |
| 14 | 257904 | 0.320 | 0.400 | 0.250 | 82% | 13 | 39 |
| 15 | 257903 | 0.172 | 0.600 | 0.153 | 98% | 51 | 83 |
| 16 | 257905 | 0.540 | 1.4 | 0.590 | 83% | 19 | 22 |
| 17 | 257906 | 0.190 | 0.550 | 0.230 | 87% | 16 | 64 |
| 18 | 258082 | 2% | 7% | 9% | 95% | | |
| 19 | 258083 | 0.110 | 0.220 | 0.150 | 97% | 56 | 97 |
| 20 | 258084 | 5% | 10% | 18% | 96% | | |
| 21 | 258085 | 4% | 7% | 4% | 99% | | |
| 22 | 257129 | 61% | 96% | 90% | 96% | | |
| 23 | 257430 | 66% | 68% | 100% | 94% | | |
| 24 | 257435 | 1.200 | 72% | 66% | 95% | | |
| 25 | 258079 | 24% | 65% | 83% | 101% | | |
| 26 | 258080 | 28% | 77% | 74% | 98% | | |
| 27 | 257723 | 0.074 | 0.14 | 0.074 | N.I. | 27 | 18 |
| 28 | 257727 | 1 | >10 | N.I. | N.I. | 29 | 23 |
| 29 | 258077 | 5.1 | 1.0 | 9.2 | 82% | | |
| 30 | 258078 | 29% | 4% | 17% | 86% | | |
| 31 | 257907 | 3.8 | 45% | 117% | 99% | 79 | 81 |
| 32 | 257908 | 5.2 | 52% | 60% | 97% | 66 | 75 |
| 33 | 257909 | 4.1 | 92% | 100% | 88% | 18 | 92 |
| 34 | 257914 | 1.7 | 64% | 67% | 99% | 77 | 81 |
| 35 | 258081 | 1.4 | 1.2 | 0.170 | 88% | 33 | 29 |
| 36 | 257726 | 0.78 | 0.79 | >10 | N.I. | 12 | 5 |
| 37 | 258074 | 4.1 | 79% | 66% | 95% | 7 | 88 |
| 38 | 258086 | 1.2 | 0.940 | 0.390 | 96% | 39 | 50 |
| 39 | 257221 | 1.200 | 93% | 79% | 95% | | |
| 40 | 257722 | 1.7 | >10 | >10 | N.I. | 15 | 50 |

N.I. No inhibition at 20 μM

TABLE 3

| | | IC50 (μM) or % Control at 20 μM | | | | OVSAHO Cell Viability (30 μM) | |
|---|---|---|---|---|---|---|---|
| | | | | | | Total Cell | % CD133 + |
| Example | CCG | ALDH1A1 | ALDH1A2 | ALDH1A3 | ALDH2 | % ctrl | % ctrl |
| 41 | 258463 | 0.27 | 75% | 15 | 120% | | |
| 42 | 258464 | 4.1 | 0.56 | 2.6 | 137% | | |
| 43 | 258465 | 69% | 1.1 | 0.75 | 153% | | |
| 44 | 258466 | 37% | 36% | 43% | 177% | | |
| 45 | 258467 | 46% | 37% | 95% | 117% | | |
| 46 | 258468 | 28% | 14% | 73% | 96% | | |
| 47 | 258471 | 28% | 15% | 79% | 110% | | |
| 48 | 258472 | 24% | 41% | 26% | 98% | | |
| 49 | 258473 | 0.570 | 2.3 | 1.05 | 89% | | |
| 50 | 258474 | 15% | 52% | 37% | 101% | | |
| 51 | 258475 | 25% | 71% | 86% | 92% | | |
| 52 | 258477 | 0.547 | 0.130 | 0.095 | 91% | | |
| 53 | 258478 | 24% | 30% | 32% | 95% | | |
| 54 | 258479 | 0.281 | 0.265 | 0.207 | 88% | | |

TABLE 3-continued

|  |  | IC50 (µM) or % Control at 20 µM | | | | OVSAHO Cell Viability (30 µM) | |
|---|---|---|---|---|---|---|---|
| Example | CCG | ALDH1A1 | ALDH1A2 | ALDH1A3 | ALDH2 | Total Cell % ctrl | % CD133 + % ctrl |
| 55 | 258480 | 0.387 | 0.139 | 0.203 | 91% | | |
| 56 | 258962 | 0.1158 | 7% | 9% | 95% | | |
| 57 | 259004 | 0.073 | 1.72 | 1.75 | 100% | 29% | 84% |
| 58 | 259006 | substrate | 3.4 (slow substrate) | 0.764 | 102% | | |
| 59 | 259007 | substrate | substrate | 0.236 | 89% | | |
| 60 | 259011 | 0.775 | 3.7 | 1.7 | 91% | 35% | 76% |
| 61 | 259122 | 0.0954 | 0.0844 | 0.0756 | 107% | 7% | 88% |
| 62 | 259123 | 88%* | 72%* | 74%* | 103% | 65% | 96% |
| 63 | 259163 | 2.28 | 43%* | 61%* | 102% | 18% | 81% |
| 64 | 262547 | 0.0507 | 0.0586 | 0.0724 | 100% | 42% | 83% |
| 65 | 262548 | 0.0694 | 0.0254 | 0.0355 | 100% | 75% | 117% |
| 66 | 262561 | 1.68 | 42%* | 0.374 | 92% | 76% | |
| 67 | 262701 | 7% | 21% | 4% | 97% | 16% | 100% |
| 68 | 262702 | 14% | 14% | 10% | 93% | 16% | |
| 69 | 262703 | 18% | 19% | 9% | 95% | 25% | 80% |
| 70 | 262704 | −5% | −14% | −10% | 90% | 17% | 56% |
| 71 | 262741 | −4% | −8% | −10% | 94% | | |
| 72 | 262901 | 26% | 34% | 24% | 96% | | |
| 73 | 263051 | 3% | 0% | 1% | 95% | | |
| 74 | 263052 | 3% | 0% | 0% | 96% | | |
| 75 | 263055 | 23% | 46% | 64% | 95% | | |
| 76 | 263056 | 16% | 25% | 14% | 94% | | |
| 77 | 263057 | 22% | 23% | 17% | 102% | | |
| 78 | 263117 | 4% | 0% | 0% | 91% | | |
| 79 | 263118 | 9% | 1% | 0% | 92% | | |
| 80 | 263119 | 6% | 7% | 0% | 96% | | |

*% Control at 5 µM

Example III

Scheme 1. Preparation of initial CM39 analogs.

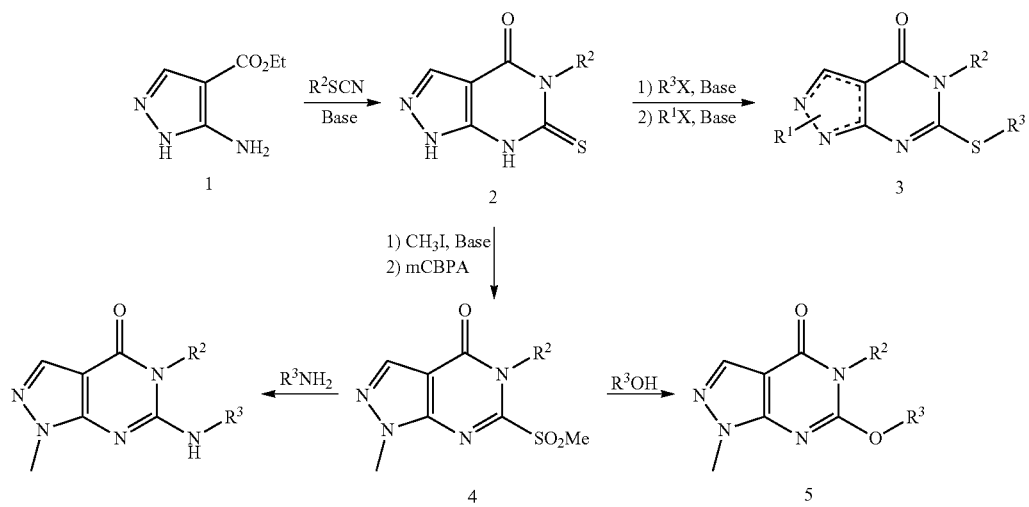

Compounds of the invention were prepared by the general synthetic route shown in Scheme 1. Commercially available pyrazole ester 1 and various isothiocyanates were condensed to form bicyclic pyrazoles 2 (see, Vicentini C B, et al., Journal of agricultural and food chemistry. 2007; 55(25): 10331-8). Alkylation of sulfur followed by optional alkylation of pyrazole nitrogen then afforded regioisomeric thiopyrimidinones 3 that were separable by chromatography. Ether and amine analogs 5 and 6 could be made by methylating the sulfur of thiopyrimidinones 2 and oxidizing to the corresponding methyl sulfones 4. Facile displacement by alcohols then provided the target ethers 5 (see, Radi M, et al., Journal of medicinal chemistry. 2011; 54(8):2610-26).

Having now fully described the invention, it will be understood by those of skill in the art that the same can be performed within a wide and equivalent range of conditions, formulations, and other parameters without affecting the scope of the invention or any embodiment thereof. All patents, patent applications and publications cited herein are fully incorporated by reference herein in their entirety.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

What is claimed is:
1. A compound selected from the group consisting of:
6-((3-fluorobenzyl)thio)-2-methyl-5-(o-tolyl)-2H-pyrazolo[3,4-d]pyrimidin-4(5H)-one,
2-ethyl-6-((3-fluorobenzyl)thio)-5-(o-tolyl)-2H-pyrazolo[3,4-d]pyrimidin-4(5H)-one,
1-(cyclopropylmethyl)-6-((3-fluorobenzyl)thio)-5-(o-tolyl)-1H-pyrazolo[3,4-d]pyrimidin-4(5H)-one,
2-(cyclopropylmethyl)-6-((3-fluorobenzyl)thio)-5-(o-tolyl)-2H-pyrazolo[3,4-d]pyrimidin-4(5H)-one,
6-((3-fluorobenzyl)thio)-1-(oxetan-3-yl)-5-(o-tolyl)-1H-pyrazolo[3,4-d]pyrimidin-4(5H)-one,
6-((3-fluorobenzyl)thio)-2-(oxetan-3-yl)-5-(o-tolyl)-2H-pyrazolo[3,4-d]pyrimidin-4(5H)-one,
6-((3-fluorobenzyl)thio)-1-(oxetan-3-ylmethyl)-5-(o-tolyl)-1H-pyrazolo[3,4-d]pyrimidin-4(5H)-one,
6-((3-fluorobenzyl)thio)-2-(oxetan-3-ylmethyl)-5-(o-tolyl)-2H-pyrazolo[3,4-d]pyrimidin-4(5H)-one,
6-((3-fluorobenzyl)thio)-2-methyl-5-phenyl-2H-pyrazolo[3,4-d]pyrimidin-4(5H)-one,
2-ethyl-6-((3-fluorobenzyl)thio)-5-phenyl-2H-pyrazolo[3,4-d]pyrimidin-4(5H)-one,
1-(cyclopropylmethyl)-6-((3-fluorobenzyl)thio)-5-phenyl-1H-pyrazolo[3,4-d]pyrimidin-4(5H)-one,
2-(cyclopropylmethyl)-6-((3-fluorobenzyl)thio)-5-phenyl-2H-pyrazolo[3,4-d]pyrimidin-4(5H)-one,
6-((3-fluorobenzyl)thio)-1-(oxetan-3-yl)-5-phenyl-1H-pyrazolo[3,4-d]pyrimidin-4(5H)-one,
6-((3-fluorobenzyl)thio)-2-(oxetan-3-yl)-5-phenyl-2H-pyrazolo[3,4-d]pyrimidin-4(5H)-one,
6-((3-fluorobenzyl)thio)-1-(oxetan-3-ylmethyl)-5-phenyl-1H-pyrazolo[3,4-d]pyrimidin-4(5H)-one,
6-((3-fluorobenzyl)thio)-2-(oxetan-3-ylmethyl)-5-phenyl-2H-pyrazolo[3,4-d]pyrimidin-4(5H)-one,
6-((3-fluorobenzyl)amino)-5-(o-tolyl)-1H-pyrazolo[3,4-d]pyrimidin-4(5H)-one,
6-((3-fluorophenethyl)amino)-1-methyl-5-(o-tolyl)-1H-pyrazolo[3,4-d]pyrimidin-4(5H)-one,
6-((3-fluorobenzyl)oxy)-1-methyl-5-(o-tolyl)-1H-pyrazolo[3,4-d]pyrimidin-4(5H)-one,
6-((3-fluorophenoxy)methyl)-1-methyl-5-phenyl-1H-pyrazolo[3,4-d]pyrimidin-4(5H)-one,
6-(((3-fluorobenzyl)amino)methyl)-1-methyl-5-phenyl-1H-pyrazolo[3,4-d]pyrimidin-4(5H)-one,
5-benzyl-6-((3-fluorobenzyl)thio)-1-methyl-1H-pyrazolo[3,4-d]pyrimidin-4(5H)-one,
6-((3-fluorobenzyl)thio)-1,5-dimethyl-1H-pyrazolo[3,4-d]pyrimidin-4(5H)-one,
6-(isopentylthio)-1-methyl-5-phenyl-1H-pyrazolo[3,4-d]pyrimidin-4(5H)-one,
6-(benzo[b]thiophen-2-ylmethoxy)-1-methyl-5-(o-tolyl)-1H-pyrazolo[3,4-d]pyrimidin-4(5H)-one,
5-cyclohexyl-6-((3-fluorobenzyl)thio)-1-methyl-1H-pyrazolo[3,4-d]pyrimidin-4(5H)-one,
5-cyclopentyl-6-((3-fluorobenzyl)thio)-1-methyl-1H-pyrazolo[3,4-d]pyrimidin-4(5H)-one,
5-cyclobutyl-6-((3-fluorobenzyl)thio)-1-methyl-1H-pyrazolo[3,4-d]pyrimidin-4(5H)-one,
(E)-6-(3-fluorostyryl)-1-methyl-5-phenyl-1H-pyrazolo[3,4-d]pyrimidin-4(5H)-one,
6-(3-fluorophenethyl)-1-methyl-5-phenyl-1H-pyrazolo[3,4-d]pyrimidin-4(5H)-one,
6-(((3-fluorobenzyl)oxy)methyl)-1-methyl-5-phenyl-1H-pyrazolo[3,4-d]pyrimidin-4(5H)-one,
1-methyl-6-((2-oxo-2-phenylethyl)thio)-5-phenyl-1H-pyrazolo[3,4-d]pyrimidin-4(5H)-one,
6-((3-fluorobenzyl)oxy)-1-methyl-5-phenyl-1H-pyrazolo[3,4-d]pyrimidin-4(5H)-one,
1-methyl-5-phenyl-6-((1-phenylethyl)thio)-1H-pyrazolo[3,4-d]pyrimidin-4(5H)-one,
6-((3-fluorobenzyl)oxy)-2-(oxetan-3-ylmethyl)-5-phenyl-2H-pyrazolo[3,4-d]pyrimidin-4(5H)-one,
2-(oxetan-3-ylmethyl)-5-phenyl-6-((1-phenylethyl)thio)-2H-pyrazolo[3,4-d]pyrimidin-4(5H)-one,
(R)-1-methyl-5-phenyl-6-((1-phenylethyl)thio)-1H-pyrazolo[3,4-d]pyrimidin-4(5H)-one,
(S)-1-methyl-5-phenyl-6-((1-phenylethyl)thio)-1H-pyrazolo[3,4-d]pyrimidin-4(5H)-one,
1-methyl-5-phenyl-6-(1-phenylethoxy)-1H-pyrazolo[3,4-d]pyrimidin-4(5H)-one,
6-((3-fluorobenzyl)thio)-2-((3-methyloxetan-3-yl)methyl)-5-phenyl-2H-pyrazolo[3,4-d]pyrimidin-4(5H)-one,
3-((6-((3-fluorobenzyl)thio)-4-oxo-5-phenyl-4,5-dihydro-2H-pyrazolo[3,4-d]pyrimidin-2-yl)methyl)azetidin-1-ium sulfate,
1-methyl-5-phenyl-6-((1-phenylpropyl)thio)-1H-pyrazolo[3,4-d]pyrimidin-4(5H)-one,
6-((1-(3-fluorophenyl)ethyl)thio)-1-methyl-5-phenyl-1H-pyrazolo[3,4-d]pyrimidin-4(5H)-one,
6-(cyclohexylthio)-1-methyl-5-phenyl-1H-pyrazolo[3,4-d]pyrimidin-4(5H)-one,
1-(oxetan-3-yl)-5-phenyl-6-((1-phenylethyl)thio)-1H-pyrazolo[3,4-d]pyrimidin-4(5H)-one,
2-(oxetan-3-yl)-5-phenyl-6-((1-phenylethyl)thio)-2H-pyrazolo[3,4-d]pyrimidin-4(5H)-one,
1-methyl-6-((2-oxocyclopentyl)thio)-5-phenyl-1H-pyrazolo[3,4-d]pyrimidin-4(5H)-one,
1-methyl-6-((2-oxocyclohexyl)thio)-5-phenyl-1H-pyrazolo[3,4-d]pyrimidin-4(5H)-one,
1-methyl-5-phenyl-6-((2-phenylpropan-2-yl)thio)-1H-pyrazolo[3,4-d]pyrimidin-4(5H)-one,
6-((1-(3-hydroxyphenyl)ethyl)thio)-1-methyl-5-phenyl-1H-pyrazolo[3,4-d]pyrimidin-4(5H)-one,
1-methyl-5-phenyl-6-((1-(pyridin-2-yl)ethyl)thio)-1H-pyrazolo[3,4-d]pyrimidin-4(5H)-one, and
1-methyl-5-phenyl-6-((1-(pyridin-3-yl)ethyl)thio)-1H-pyrazolo[3,4-d]pyrimidin-4(5H)-one.

* * * * *